(12) United States Patent
Gisler et al.

(10) Patent No.: US 9,678,092 B2
(45) Date of Patent: *Jun. 13, 2017

(54) WORKFLOW TIMING BETWEEN MODULES

(71) Applicant: Roche Molecular Systems, Inc., Pleasanton, CA (US)

(72) Inventors: Andreas Gisler, Thalwil (CH); Robert Huesler, Root (CH); Rolf Knobel, Rotkreuz (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/856,412

(22) Filed: Sep. 16, 2015

(65) Prior Publication Data

US 2016/0054340 A1    Feb. 25, 2016

Related U.S. Application Data

(60) Continuation of application No. 14/614,217, filed on Feb. 4, 2015, which is a division of application No. 13/039,002, filed on Mar. 2, 2011, now Pat. No. 9,034,575.

(30) Foreign Application Priority Data

Mar. 4, 2010 (EP) .................................... 10155420

(51) Int. Cl.
*G01N 35/00* (2006.01)
*G01N 35/02* (2006.01)
*G01N 35/10* (2006.01)

(52) U.S. Cl.
CPC ... *G01N 35/00732* (2013.01); *G01N 35/0092* (2013.01); *G01N 35/0098* (2013.01); *G01N 35/026* (2013.01); *G01N 35/10* (2013.01); *G01N 2035/00326* (2013.01); *G01N 2035/00356* (2013.01); *G01N 2035/00465* (2013.01); *Y10T 436/11* (2015.01)

(58) Field of Classification Search
CPC .......... G01N 2035/00326; G01N 2035/00356; G01N 2035/00465; G01N 35/00732; G01N 35/0092; G01N 35/0098; G01N 35/026; G01N 35/10
See application file for complete search history.

(56) References Cited

U.S. PATENT DOCUMENTS

| 6,096,561 | A | * | 8/2000 | Tayi | ................... | B01F 11/0022 |
| | | | | | | 422/50 |
| 7,597,848 | B1 | | 10/2009 | Ameling et al. | | |
| 2002/0090320 | A1 | | 7/2002 | Burow et al. | | |
| 2010/0129789 | A1 | * | 5/2010 | Self | .......................... | B01L 9/06 |
| | | | | | | 435/5 |

FOREIGN PATENT DOCUMENTS

| EP | 1582874 B1 | 7/2008 |
| EP | 2363712 | 9/2011 |
| WO | 2006002960 A1 | 1/2006 |
| WO | 2008012104 A2 | 1/2008 |
| WO | 2008012104 A3 | 1/2008 |

* cited by examiner

*Primary Examiner* — Cynthia B Wilder
(74) *Attorney, Agent, or Firm* — Pamela C. Ancona; David J. Chang

(57) ABSTRACT

The invention relates to a method of isolating and analyzing an analyte using an analytical apparatus which comprises modules of different types, wherein any one module of one type has a specific, pre-defined timing for carrying out its workflow.

10 Claims, 33 Drawing Sheets

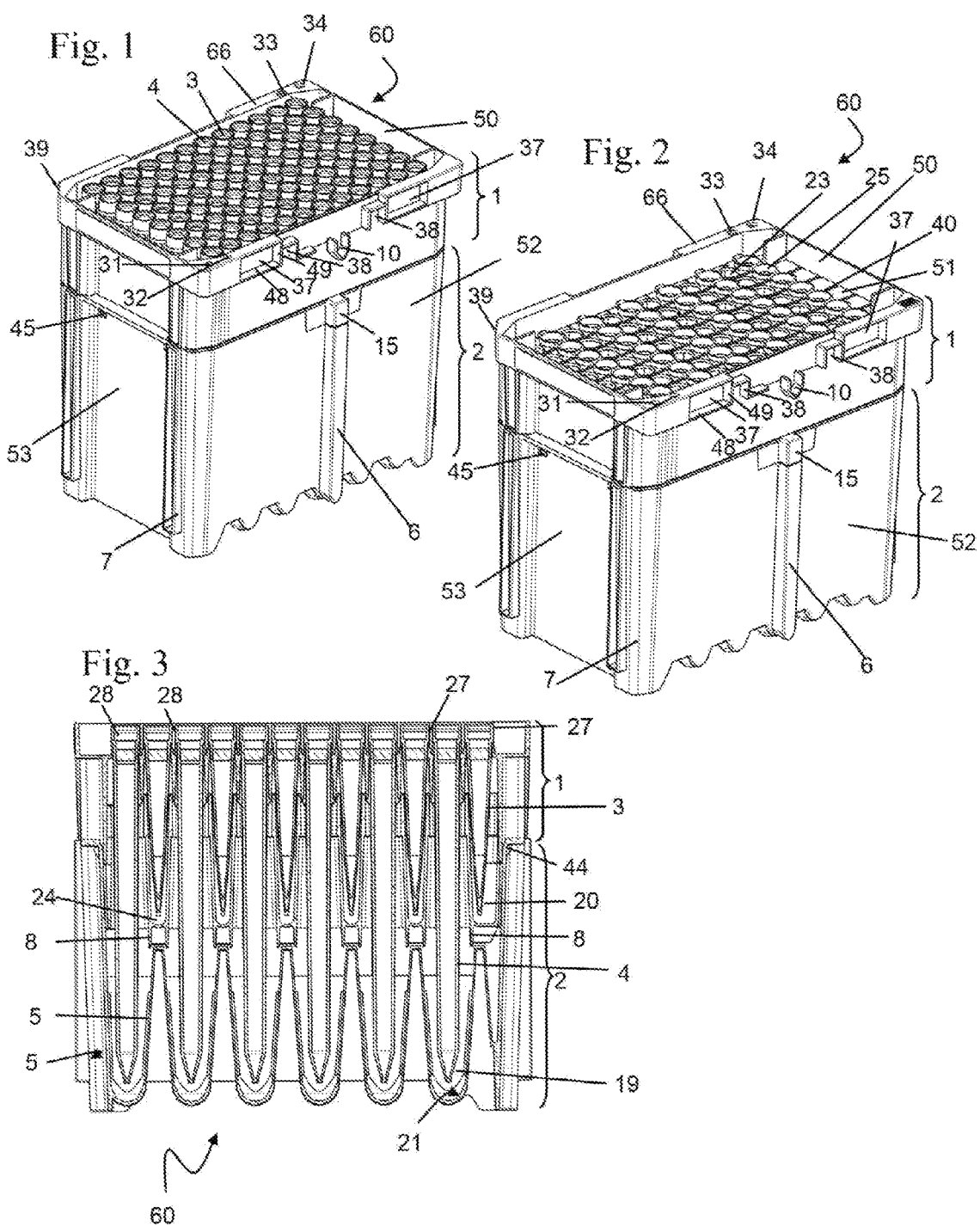

Fig. 11
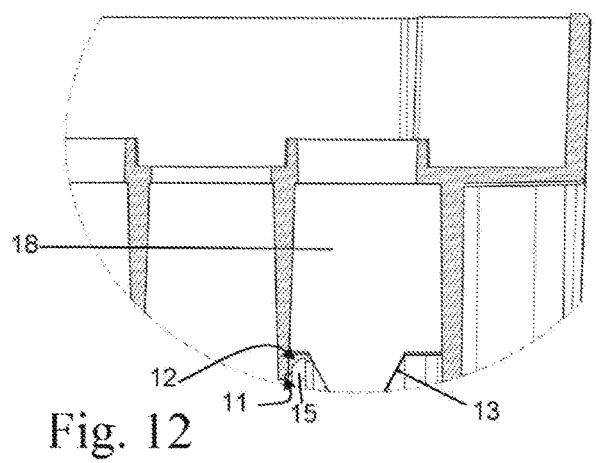
Fig. 14 a)
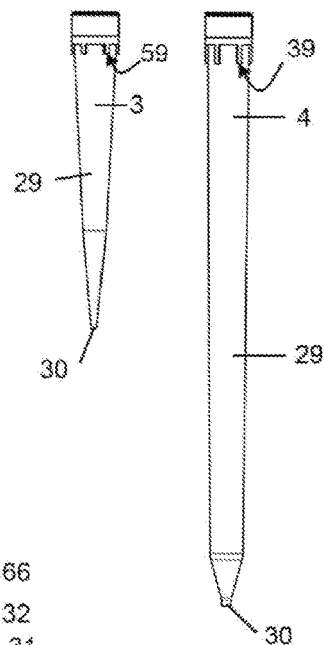
Fig. 12
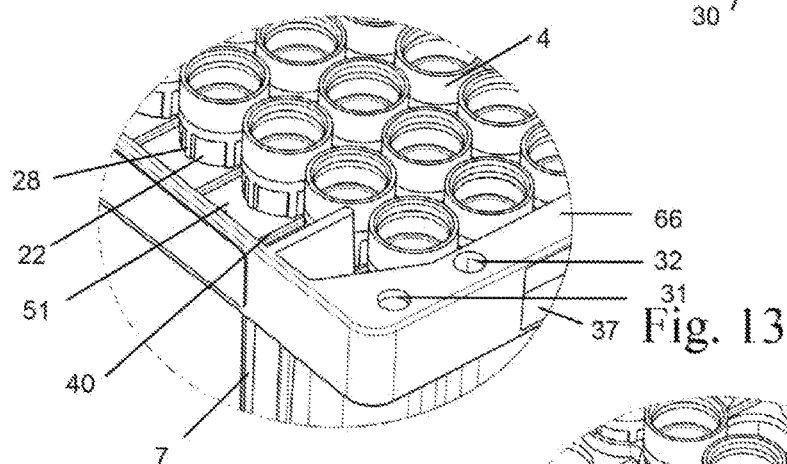
Fig. 14 b)
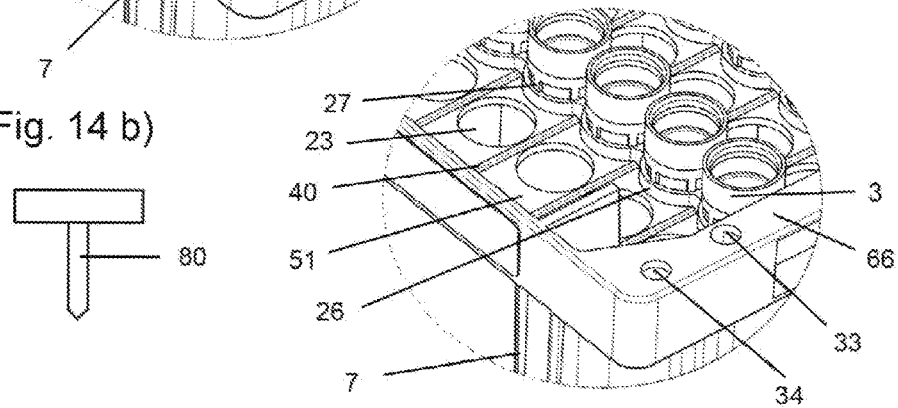
Fig. 13

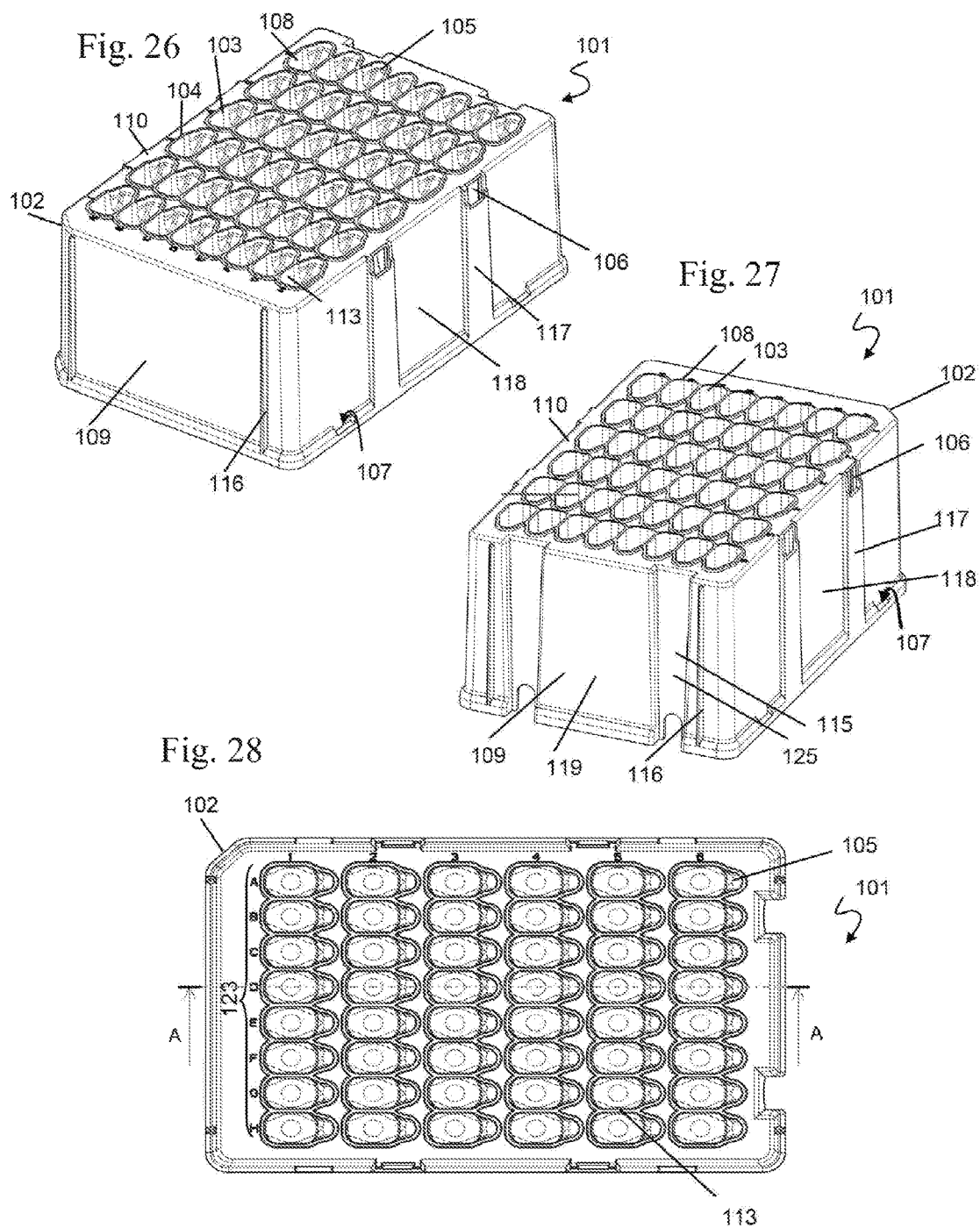

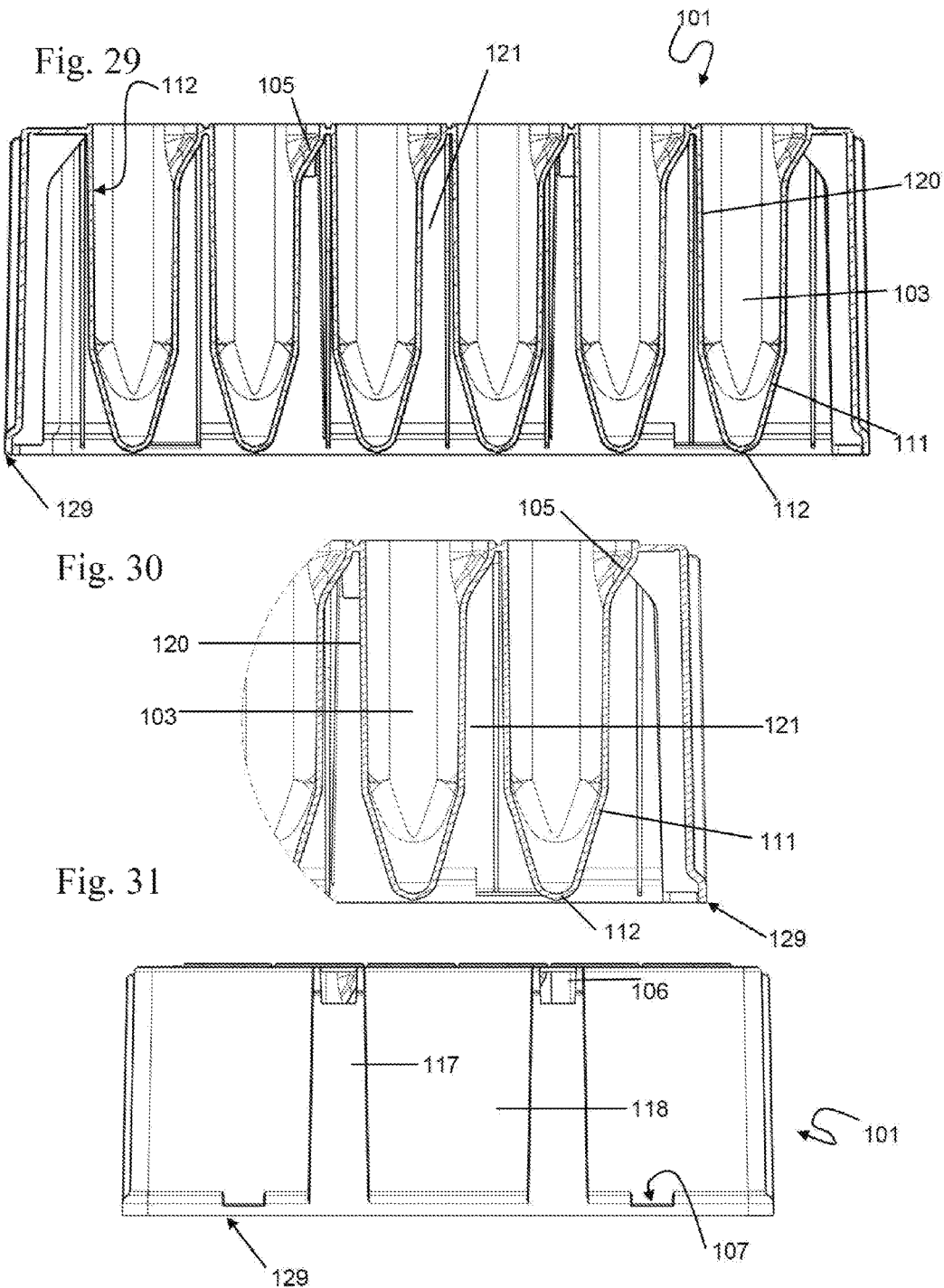

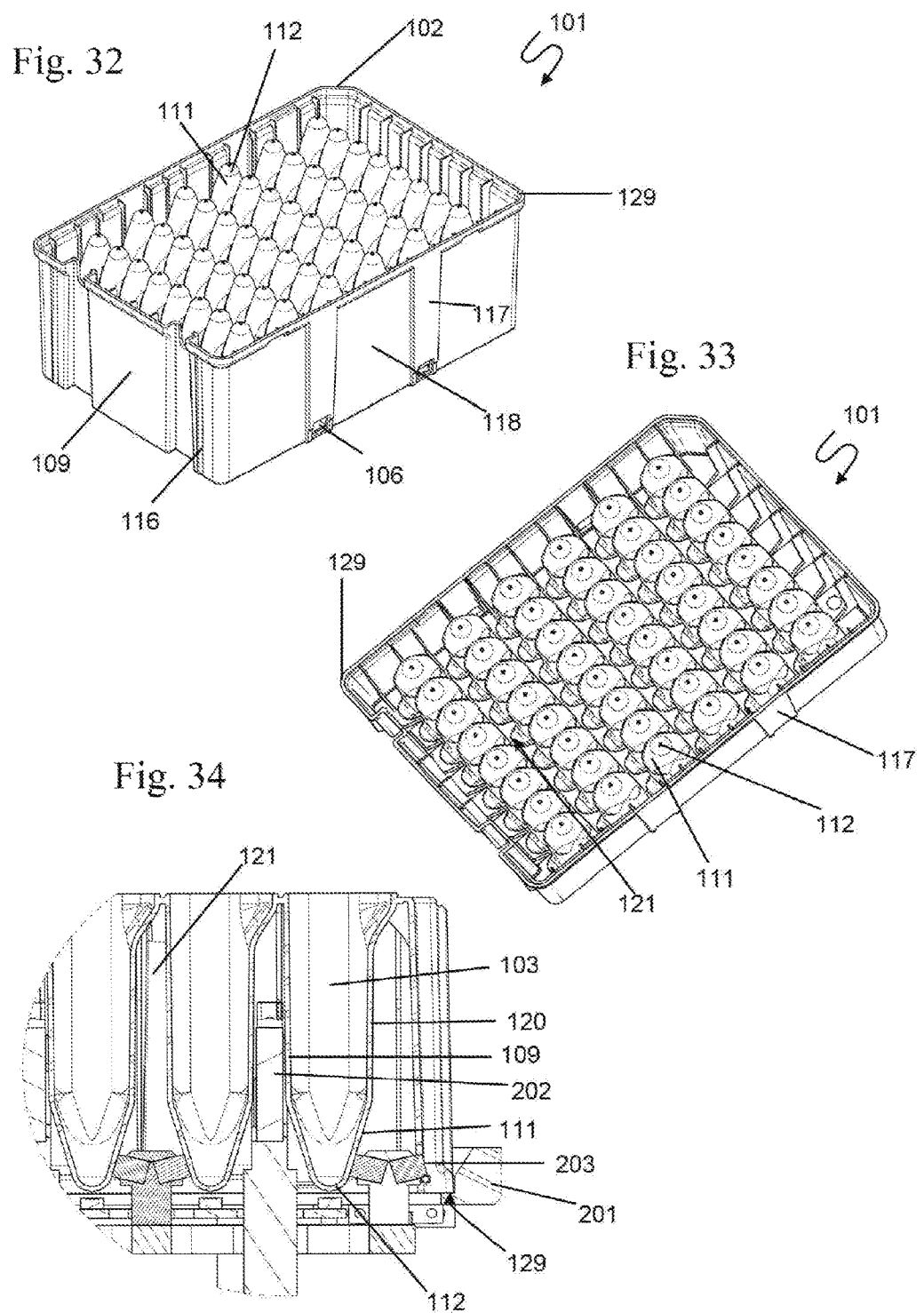

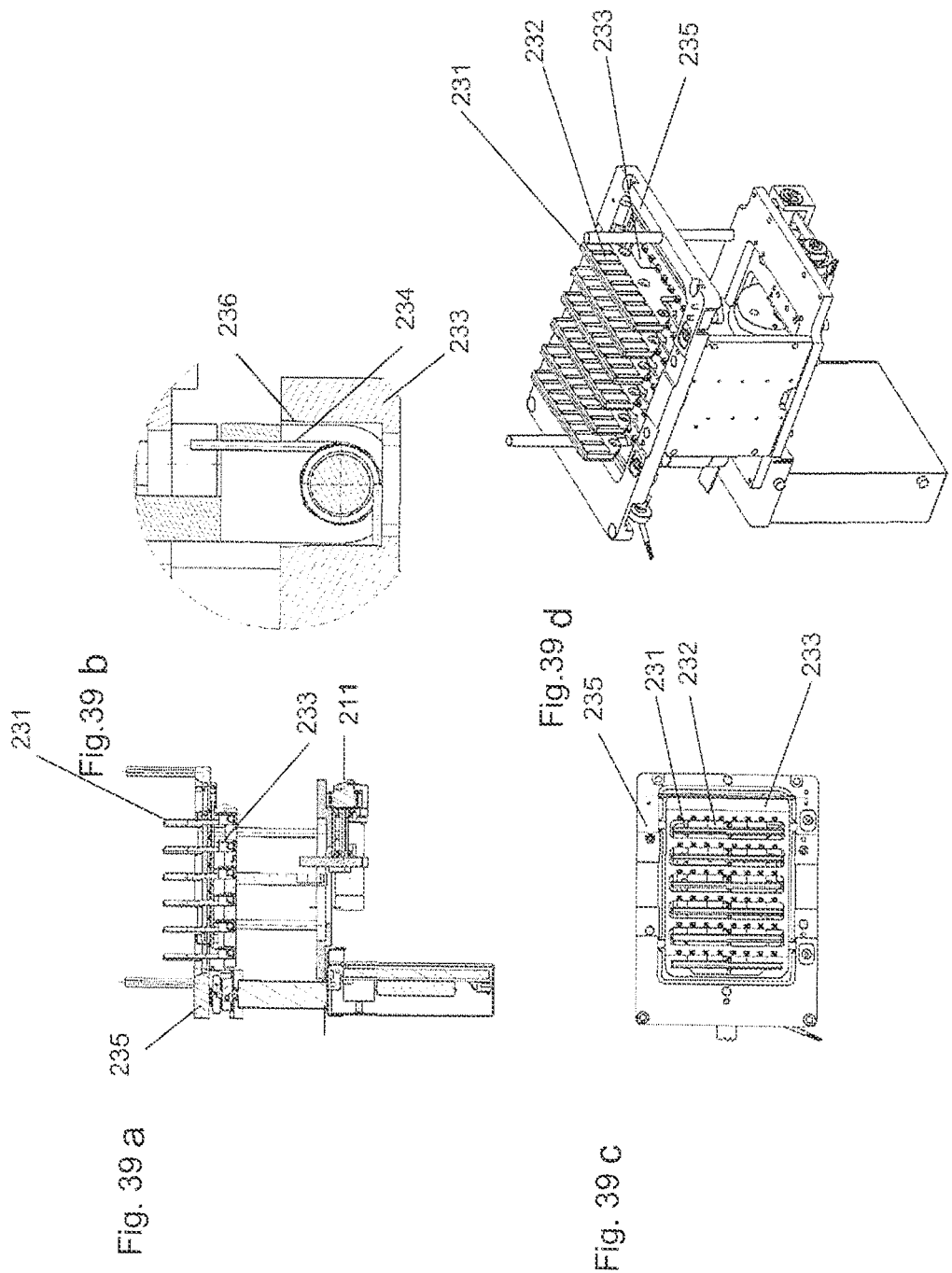

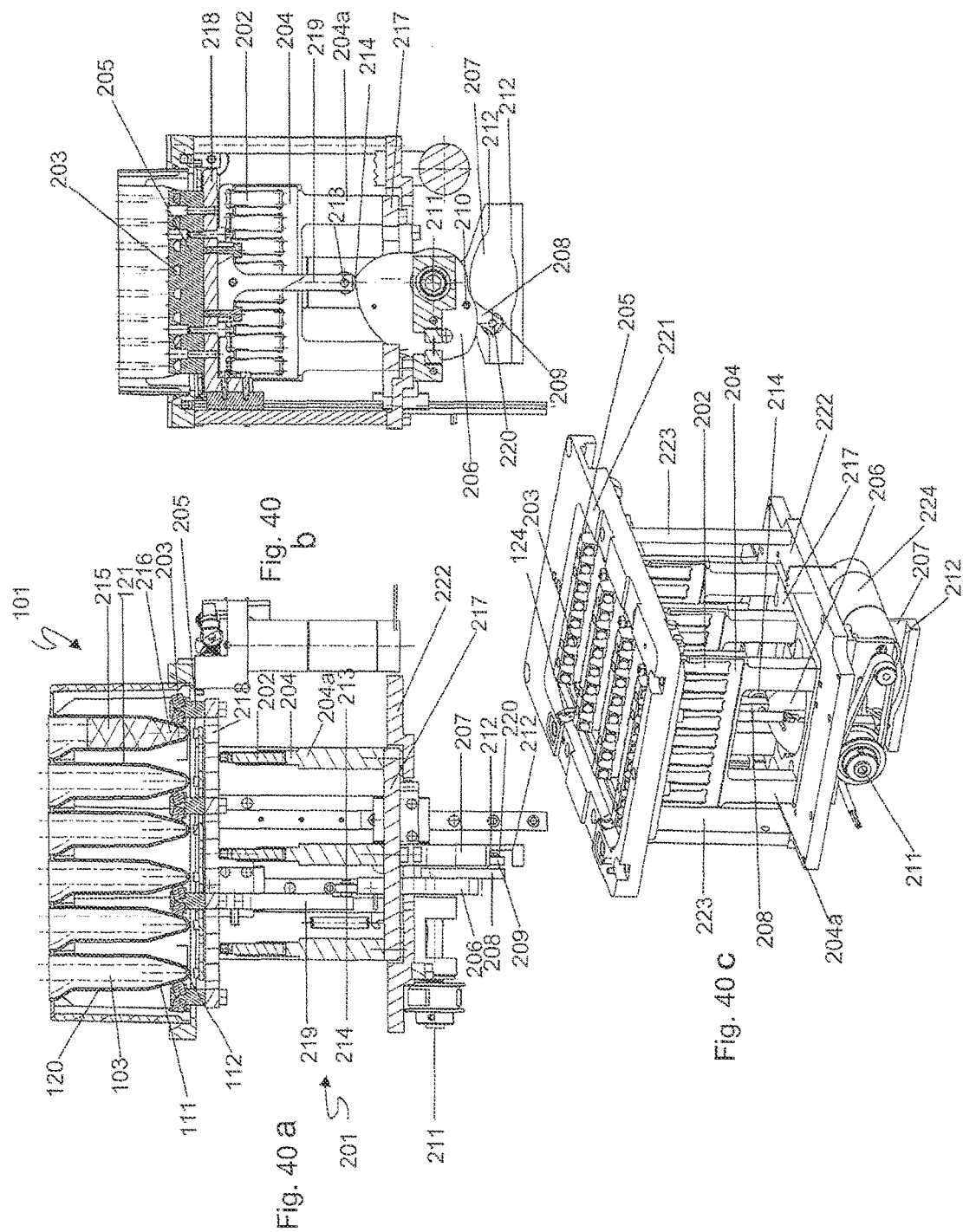

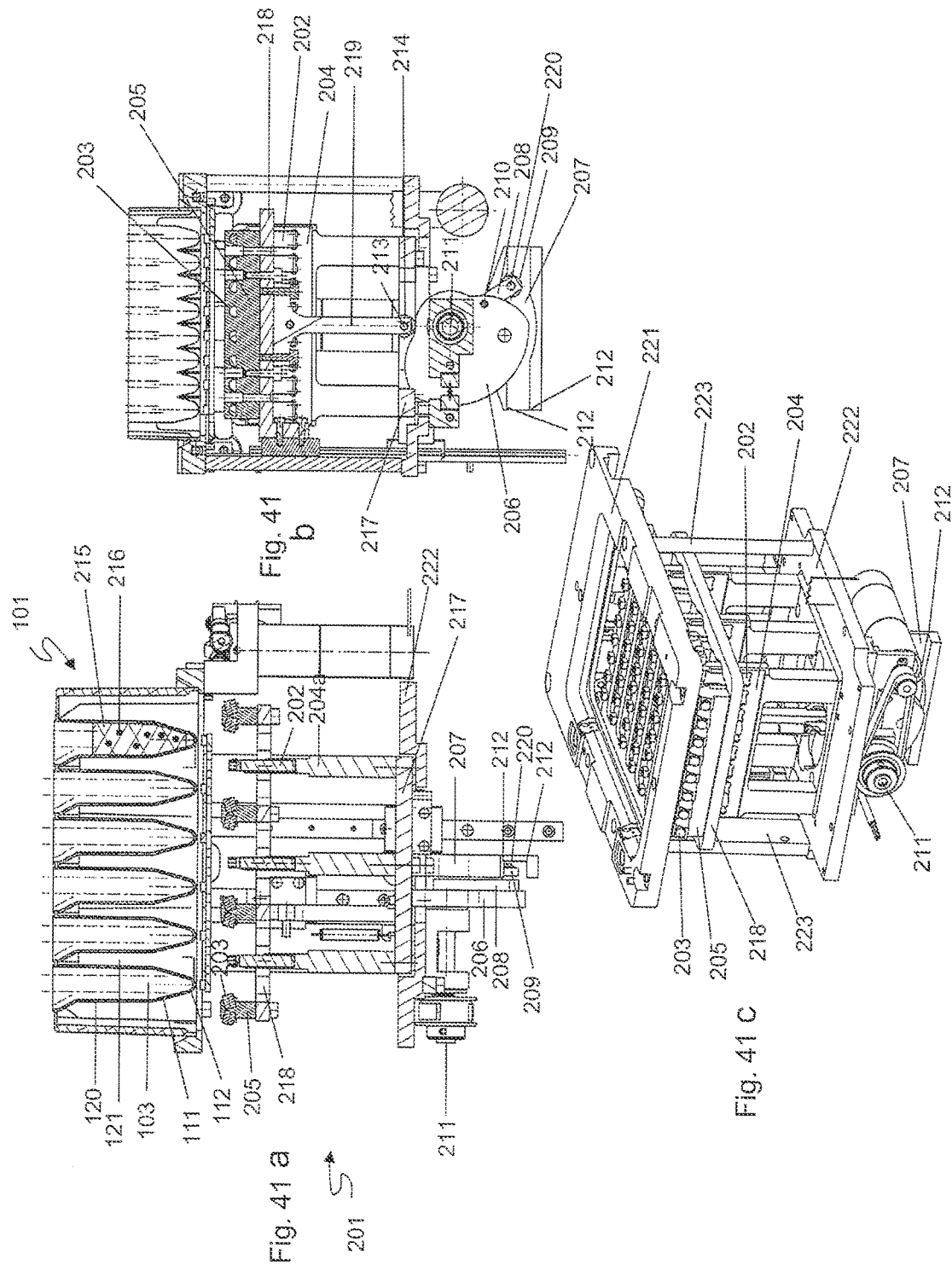

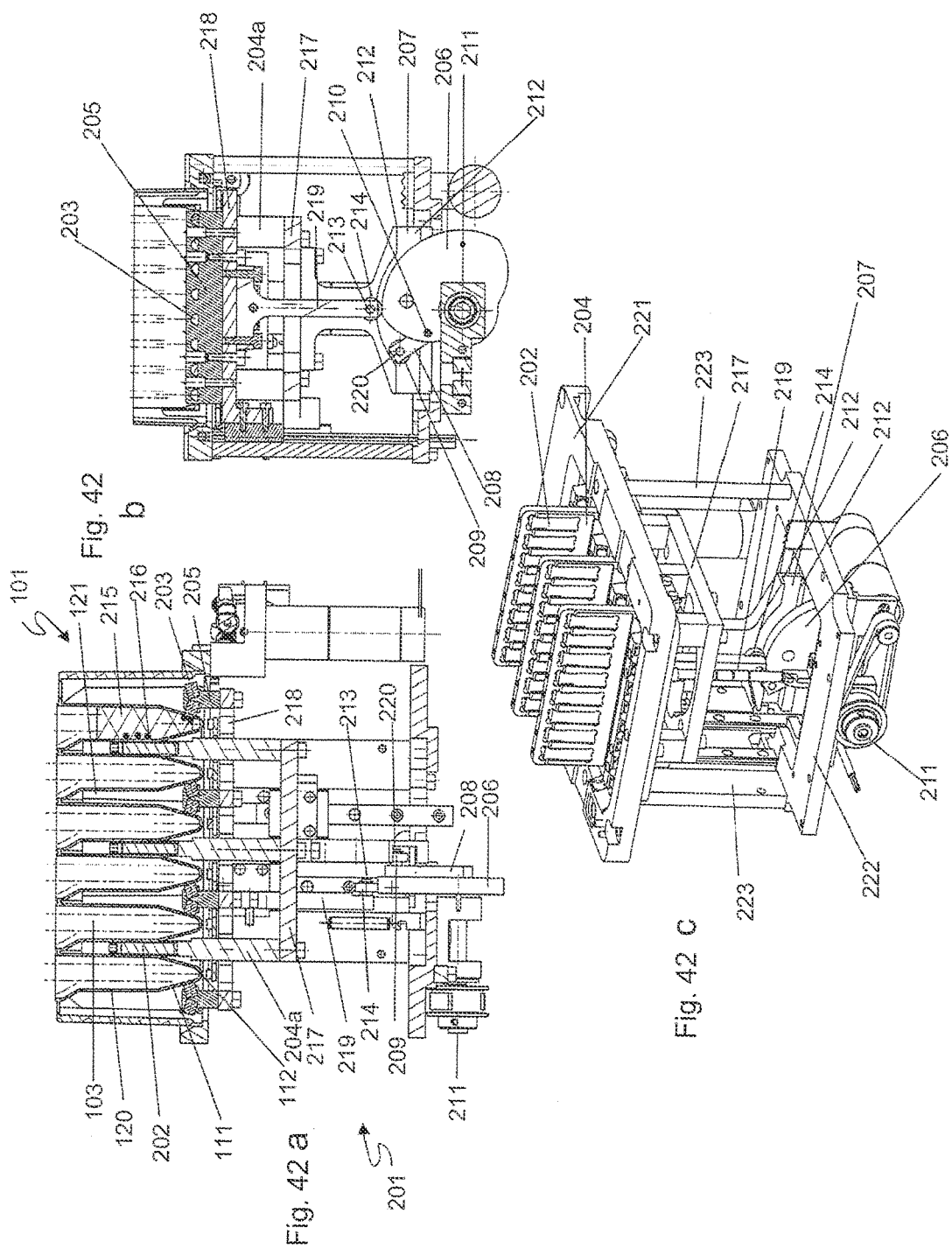

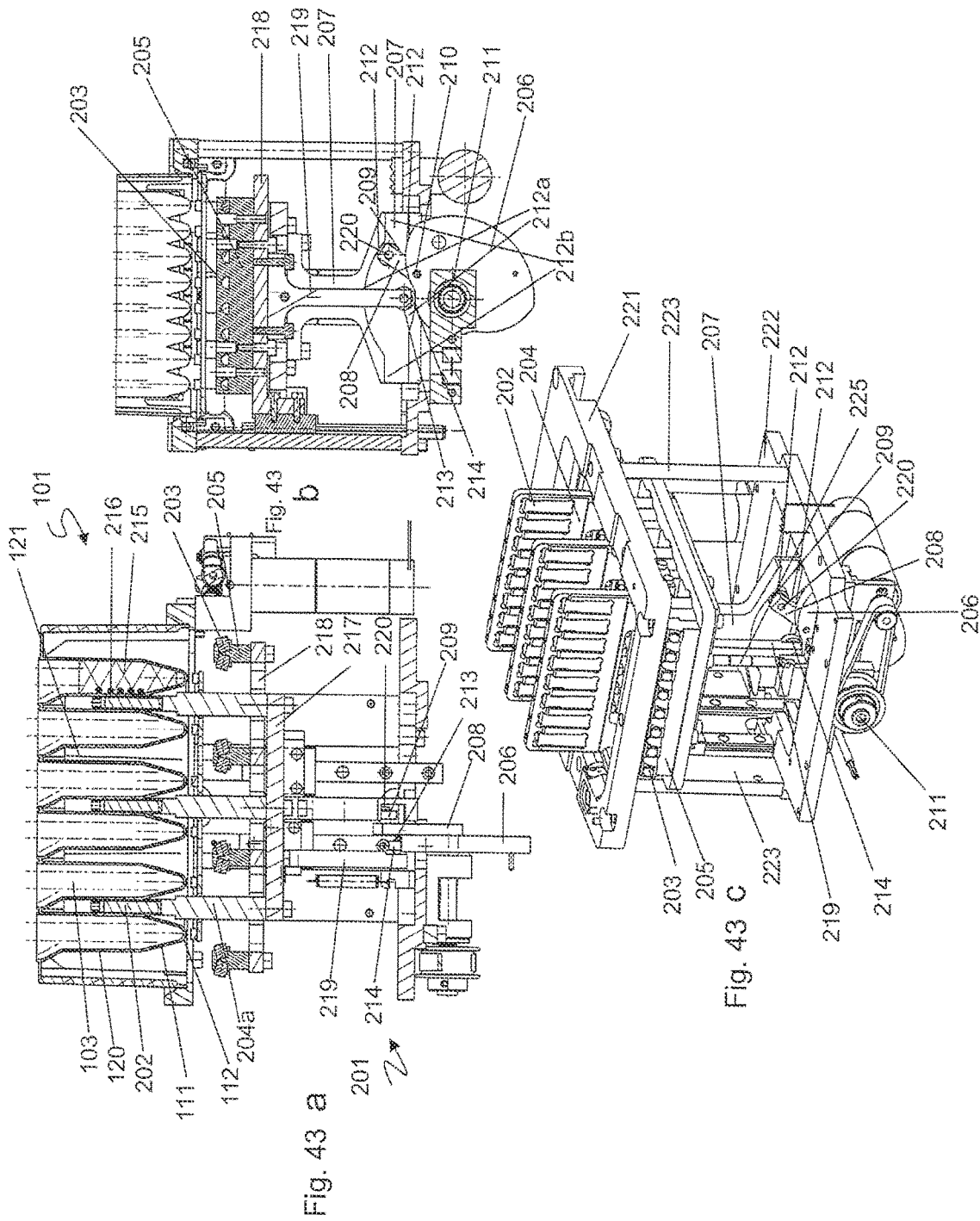

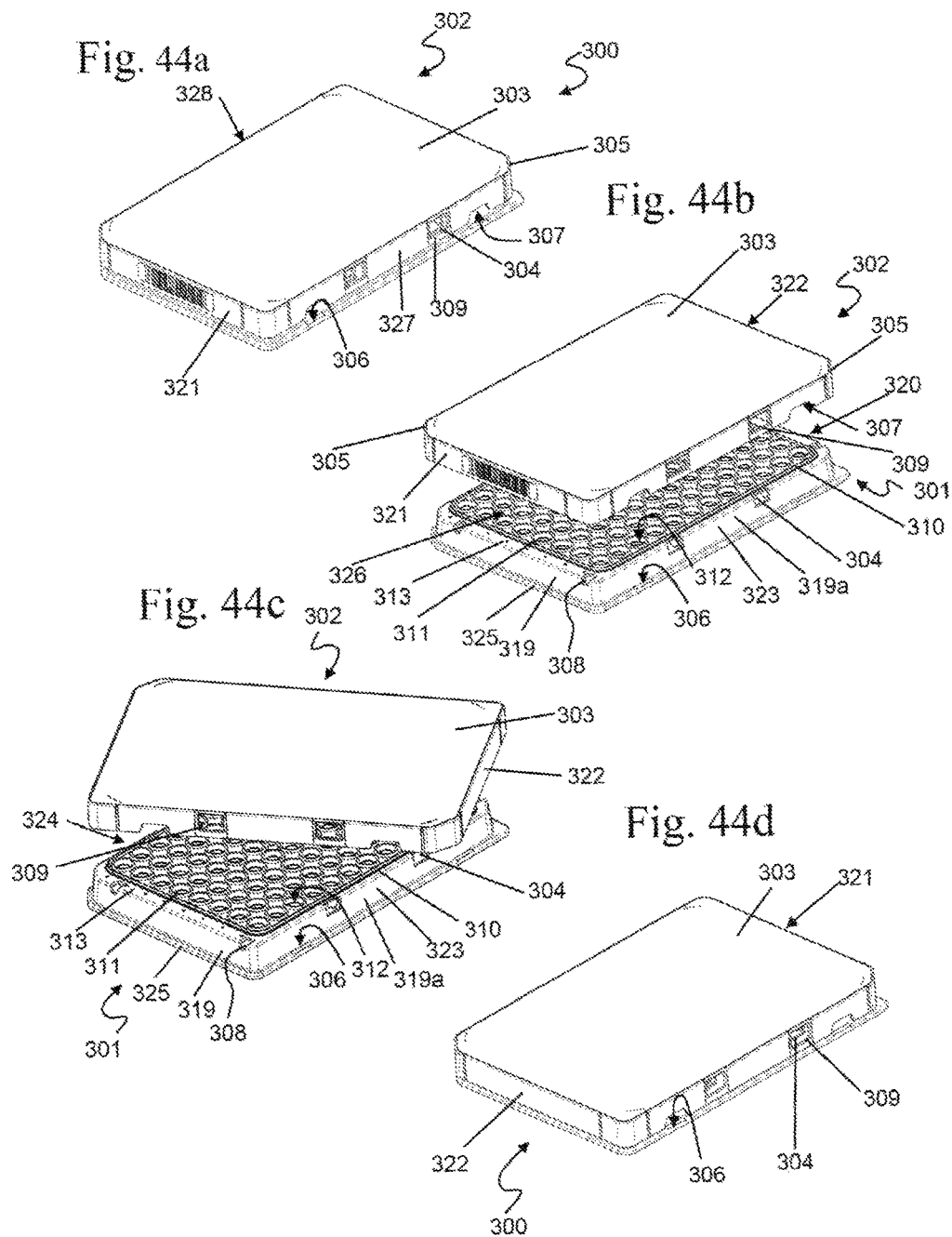

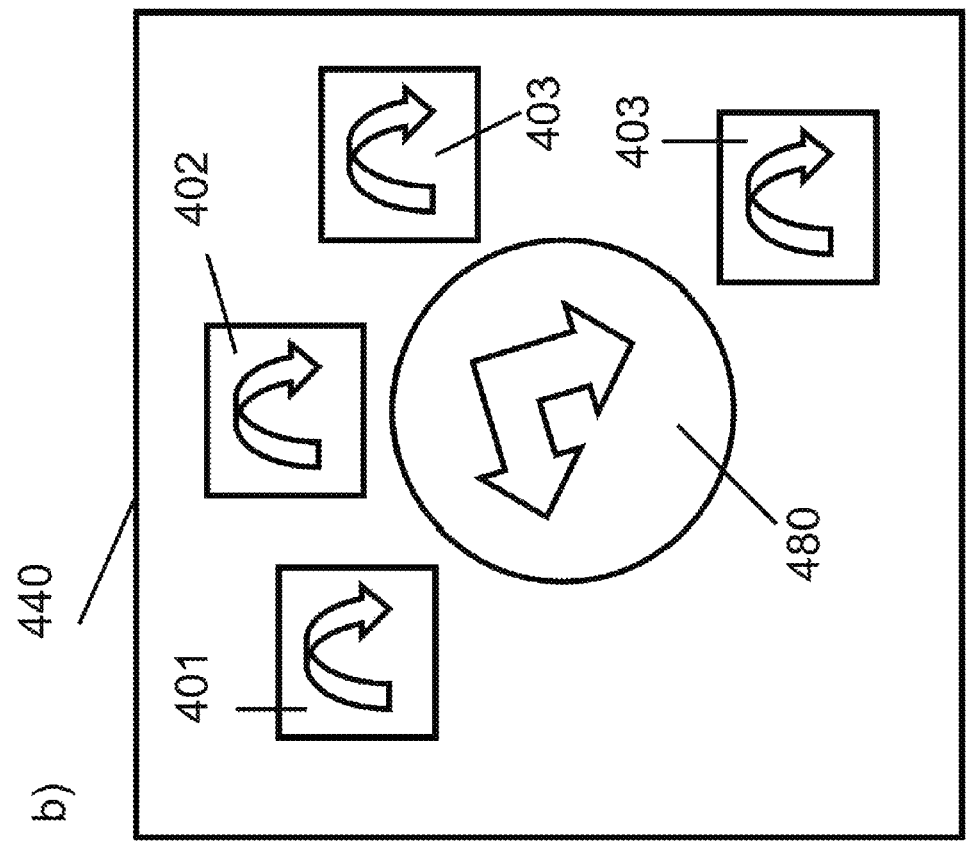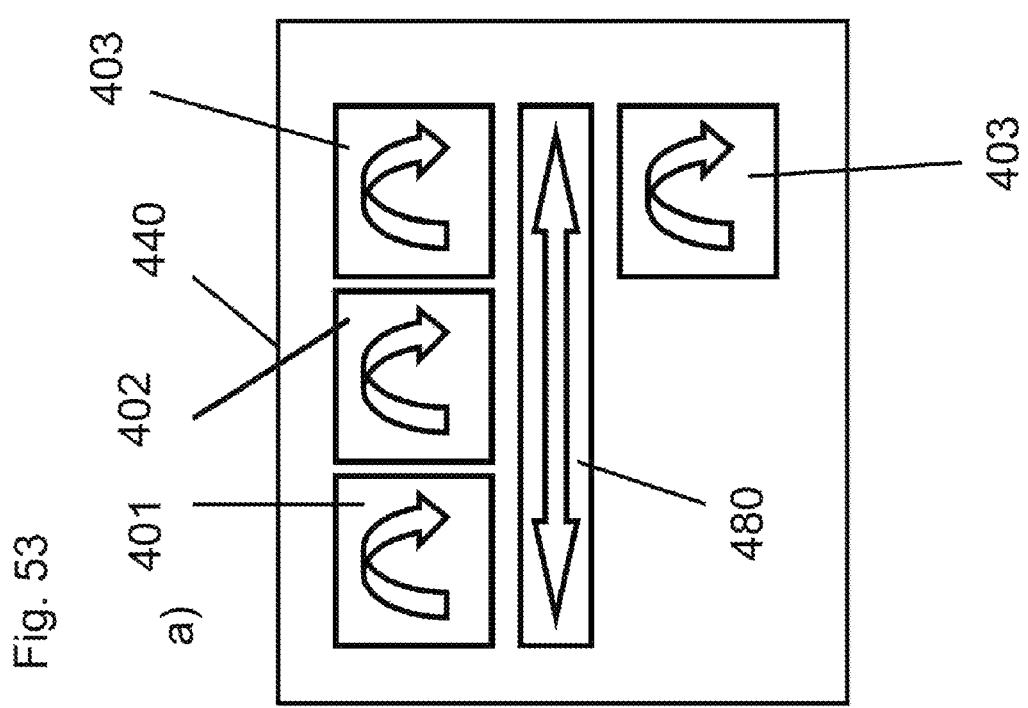
Fig. 53

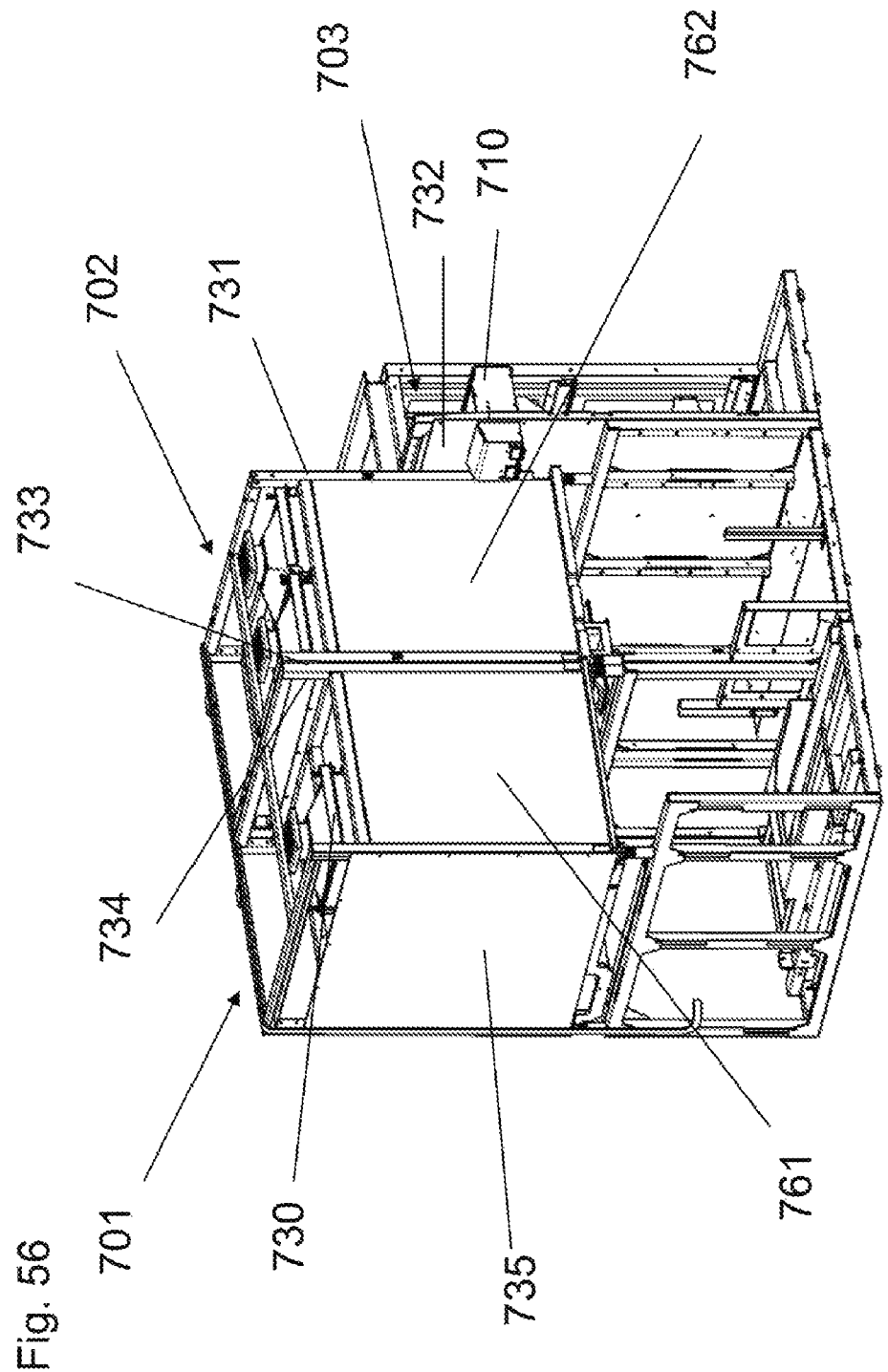

WORKFLOW TIMING BETWEEN MODULES

CROSS-REFERENCES TO RELATED APPLICATIONS

The present application is a continuation of U.S. application Ser. No. 14/614,217, filed on Feb. 4, 2015, which is a divisional of U.S. application Ser. No. 13/039,002 filed on Mar. 2, 2011, which claims the benefit of priority under 35 U.S.C. §119 of EP10155420.2, filed Mar. 4, 2010, the contents of each are all incorporated by reference herein in their entirety.

FIELD OF THE INVENTION

The present invention relates to an automated method for isolating and analyzing an analyte in an automated analyzer.

BACKGROUND OF THE INVENTION

Analytical systems used in the field of diagnostics require preparation of samples, processing of samples comprising analytes to be analysed, followed by analysis of an analyte. WO 99/057561 discloses an automated nucleic acid analyzer in which every receptacle comprising a sample with a target nucleic acid analyte moved through all of the different stations of the analyzer for target-capture isolation of the target nucleic acid and subsequent isothermal amplification. The analyzer only comprises one separation station, one amplification station and one detection station.

WO 2008/012104 discloses an analyzer with different modules. A sample preparation module, a module for preparing an amplification reaction mixture, and an optional module for amplification of a nucleic acid analyte can be combined.

The present invention provides for an improved multi-modular analytical system optimized workflow timing of the modules.

SUMMARY OF THE INVENTION

The present invention relates to a method and system of isolating and analyzing an analyte in an automated analyzer, comprising the step of providing a liquid sample comprising said analyte to a processing vessel in a module of a first type. From the first module, in a next step of the method of the present invention, the liquid sample comprising said analyte is transferred to a module of a second type. The analyte is then isolated and purified in the processing vessel in the module of a second type. Following isolation and purification, the purified analyte is transferred to a module of a third type. In this module of a third type, the analyte is analyzed by reacting said analyte with reagents necessary to obtain a detectable signal. The timing for transfer and processing within any one module of one type is pre-defined. The timing of any one module is identical for any one analyte which is being isolated and analyzed.

The advantage of the invention is that the pre-defined timing of any one module one type allows for optimization of the overall workflow timing, and makes it possible to achieve an optimized high throughput for analytical tests.

BRIEF DESCRIPTION OF THE FIGURES

FIG. 1 shows a view of an assembled rack loaded with pipette tips.

FIG. 2 shows a view of a rack without loaded tips.

FIG. 3 shows a cross section through the longer side walls of the rack loaded with two types of pipette tips.

FIG. 11 shows a partial cross-sectional view through the assembled rack without pipette tips loaded.

FIG. 12 shows a perspective view of the upper rack loaded with pipette tips, with details of the first type of tips sitting on the through bore-holes.

FIG. 13 shows a perspective view of the upper rack loaded with pipette tips, with details of the second type of tips sitting on the rim of through bore-holes.

FIG. 14 (a) shows a perspective view of the first and second types of pipette tips; FIG. 14 (b) shows a pipette needle.

FIG. 26 shows a perspective view of the Processing Plate.

FIG. 27 shows a perspective view of the Processing Plate from the opposite angle.

FIG. 28 shows a top view of the processing plate.

FIG. 29 shows a cross-sectional view along the longer side of the processing plate.

FIG. 30 shows a partial view of the cross-sectional view.

FIG. 31 shows a perspective view of the longer side of the Processing plate.

FIG. 32 shows a perspective view of the bottom of the Processing plate.

FIG. 33 shows a more vertical perspective view of the bottom of the Processing plate.

FIG. 34 shows the fitting of the smaller magnets of the first preferred embodiment of the separation station with the vessels of the Processing plate.

FIGS. 39 (a) to (d) show different views of the second embodiment of the magnetic separation station wherein the side view (FIG. 39a), detailed view of the base (233) (FIG. 39b), top view (FIG. 39c) and lateral view (FIG. 39d) of the station are shown.

FIGS. 40 (a) to (c) show a view of the first embodiment of the magnetic separation station holding the Processing plate (FIG. 40a), with the first type of magnets in the uppermost Z-position (FIG. 40b), and the second type of magnets in the lowermost Z-position (FIG. 40c).

FIGS. 41 (a) to (c) show a view of the first embodiment of the magnetic separation station holding the Processing plate (FIG. 41a), with the first type of magnets in the uppermost Z-position (FIG. 41b), and the second type of magnets in the uppermost Z-position (FIG. 41c).

FIGS. 42 (a) to (c) show a view of the first embodiment of the magnetic separation station holding the Processing plate (FIG. 42a), with the first type of magnets in the lowermost Z-position (FIG. 42b), and the second type of magnets in the uppermost Z-position (FIG. 42c).

FIGS. 43 (a) to (c) show a view of the first embodiment of the magnetic separation station holding the Processing plate (FIG. 43a), with the first type of magnets in the lowermost Z-position (FIG. 43b), and the second type of magnets in the lowermost Z-position (FIG. 43c).

FIGS. 44 (a) to (d) shows the AD plate and frame with sealing foil in storage position (FIG. 44a), with lifted lid (FIG. 44b), during rotation of lid (FIG. 44c) and in sealing position (FIG. 44d).

FIG. 45 (b) shows a sealing foil with two layers and the top of the lid comprising a frame.

FIGS. 46 (c) and (d) show side (FIG. 46c) and top (FIG. 46d) sectional views of a corner of the AD plate and frame in sealing position.

FIG. 50 (c) shows that the handler interacts with different consumable with the same interface.

FIG. 53 (c) shows a preferred system with one module of a first type, two modules of a second type and four modules of a third type.

FIG. 56 shows a perspective view of an analytical apparatus of the present invention with front walls.

DETAILED DESCRIPTION OF THE INVENTION

Figure 4:
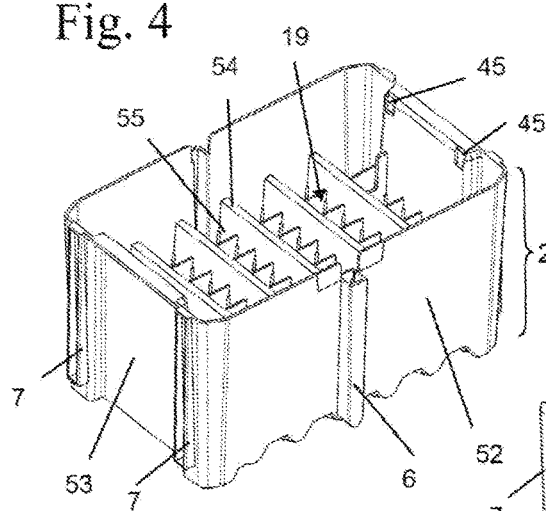
FIG. 4 shows a perspective view of the top-side of the lower rack.

Analytical Apparatus and Method for Isolating and Analyzing an Analyte

A method for isolating and analyzing an analyte that may be present in a fluid sample is disclosed. Said method comprises the automated steps of:
  a) transferring said fluid sample from a sample vessel to a processing vessel with a pipette tip;
  b) combining together a solid support material and said fluid sample in a well of said processing vessel for a period of time and under conditions sufficient to permit said analyte to be immobilized on the solid support material;
  c) isolating the solid support material from other material present in the fluid sample in a separation station; and
  d) purifying the analyte in the separation station by separating the fluid sample from the solid support material and washing the materials one or more times with a wash buffer.

Preferably, said pipette tip used in step (a) is re-used after step (a).

In a preferred embodiment, said pipette tip is a pipette tip of a first type, and said pipette tip of a first type is stored in a rack comprising pipette tips of a first type and pipette tips of a second type. Preferably, said pipette tips of a first and second type are stored in said rack at least and between being used for pipetting.

In a preferred embodiment of the method hereinbefore described, step a) comprises:
  a1) engaging pipette tips of a first type which are held in a rack in a first position with a first process head;

a2) transferring said fluid sample from a sample vessel to a processing vessel with pipette tips of a first type engaged to a first process head;
a3) placing said pipette tips in said rack and disengaging said pipette tips from said process head;
a4) transporting said rack comprising said pipette tips and said processing vessel to second positions;
a5) engaging said pipette tips of a first type which are held in said rack with a second process head in said second position.

Preferably, the processing vessel comprises more than one receptacle. More preferably, the processing vessel is a multiwell plate. The method preferably additionally comprises the step of:
e) reacting said purified analyte with reagents necessary to obtain a detectable signal.

Re-use of pipette tips leads to a reduction of disposable consumables used in the analytical method and to cost reductions. In a preferred embodiment, the washing in step d) comprises aspirating and dispensing the washing buffer with a process head engaged to pipette tips.

The term "receptacle" as used herein relates to a single vessel (or tube) or to a tube comprised in a multi-tube unit, or to a well (or vessel) of a multiwell plate.

The term "vessel" is understood to mean a single vessel or a single vessel in a multi-tube unit, a multiwell plate or a multi-tube unit or a well of a multiwell plate.

In a preferred embodiment, the reacting comprises generating a detectable signal. More preferably, the method additionally comprises the step of detecting a detectable signal.

The term "analyte" as used herein may be any type of biomolecule which is of interest for detection, and the detection thereof is indicative of a diagnostic status of an organism. The organism can be animal or, more preferably, human. Preferred analytes are proteins, polypeptides, antibodies or nucleic acids. More preferably, the analyte is a nucleic acid.

The term "reacting" as used herein relates to any type of chemical reaction of the analyte with reagents that is necessary to obtain a detectable signal. Preferably, said reacting comprises amplification. Amplification may be understood as any type of enhancement of a signal. Thus, amplification can be a conversion of a molecule by an enzyme, wherein said enzyme is coupled or bound to the analyte, leading to a detectable signal, wherein more signal molecules are formed than analyte molecules are present. One such non-limiting example is a formation of a chemiluminescent dye, e.g. using ECL. The term amplification further relates to nucleic acid amplification, if the analyte is a nucleic acid. This includes both linear, isothermal and exponential amplifications. Non-limiting examples of nucleic acid amplification methods are TMA, SDA, NASBA, PCR, including real-time PCR. Such methods are well known to the skilled person.

The term "solid support" as used herein relates to any type of solid support to which the analyte is capable of binding, either directly by adsorption, or indirectly and specifically. Indirect binding may be binding of an analyte to an antibody immobilized on the solid support, or binding of a tag to a tag binding compound, e.g. binding of 6×His tags to Ni-chelate. When the analyte is a nucleic acid, such indirect binding is preferably by binding to a capture nucleic acid probe which is homologous to a target sequence of the nucleic acid of interest. Thus, using capture probes attached on a solid support, a target analyte, preferably a target nucleic acid, can be separated from non-target material, preferably non-target nucleic acid. Such capture probe is immobilized on the solid support. Solid support material may be a polymer, or a composition of polymers. Other types of solid support material include magnetic silica particles, metal particles etc.

Preferred direct binding of nucleic acid to silica particles occurs in the presence of chaotropic compounds. Such binding may also be referred to as direct binding, as opposed to the indirect binding described above. Preferably, the solid supports silica particles which comprise a magnetic or magnetizable material.

A "separation station" is understood to be a station where an analyte is separated from a solid support.

In a preferred embodiment of the method hereinbefore described, the transporting of said rack comprising said pipette tips and said processing vessel to a second positions occurs between a separate first cell of an analytical instrument and a separate second cell, preferably a processing cell, of said analytical system. Preferably, the rack comprises independent chambers to accommodate pipette tips.

In a preferred embodiment, the first type of pipette tips is re-used for the washing in step d).

In a preferred embodiment, the rack additionally comprises a second type of pipette tips. Further preferred is a method as hereinbefore described, wherein between step d) and e), the analyte is eluted from the magnetic particles. A preferred embodiment comprises the transfer of the analyte from said processing vessel, which is preferably a multiwell plate, to a reaction vessel, which is preferably a multiwell plate, with said second type of pipette tips.

An analytical system for isolating an analyte is disclosed, said system comprising:
a) a first position comprising a first receptacle holding a liquid sample comprising an analyte, a second receptacle for holding a liquid sample, a rack holding pipette tips, and a first process head for transferring a liquid sample from the first receptacle to a second receptacle,
b) a second position comprising a station for receiving said second receptacle, and a rack holding station for receiving said rack,
c) a transfer system for transferring the second receptacle and the rack holding pipette tips between the first position and the second position.

Preferably, the positions are separate cells. The rack transferred by said transfer system preferably comprises pipette tips which were used in the first position. In a preferred embodiment, the first receptacle is a sample vessel and the second receptacle is a processing vessel. Further preferred is a processing vessel which is a multiwell vessel. Preferred embodiments of said stations are described hereinafter.

In the analytical system herein described, the transport system preferably transfers the receptacle and the rack from the first position to the second separate position. Preferably, the second separate position comprises a magnetic separation station. The analytical system additionally preferably comprises an amplification station.

The transport system of the preferred system comprises a handler constructed and arranged to grip and transport said rack and said processing vessel from a first to a second location within the system. Further preferred handlers are disclosed herein.

The system is preferably fully automated.

An automated analyzer for isolating and analyzing an analyte comprising a plurality of stations disposed within said analyzer is also disclosed. The plurality of stations comprises a sample dispensing station disposed in a first location. Preferably, said sample dispensing station is constructed and arranged to dispense liquid sample comprising an analyte from a sample vessel to a processing vessel with pipette tips held in a rack. Further preferred sample dispensing stations are stations comprising a sample vessel, a processing vessel and a liquid dispensing unit. Said liquid dispensing unit is preferably a process device.

The automated analyzer further comprises a separation station disposed in a second location. Preferably, said separation station is constructed and arranged to receive said processing vessel holding said liquid sample and said rack holding pipette tips used in the sample dispensing station and to separate an analyte from other material present in the liquid sample. Another preferred embodiment of a separation station is a separation station comprising movable magnets.

The automated analyzer further comprises a reaction station disposed in a third location, wherein said reaction station is constructed and arranged to analyze said analyte to obtain a detectable signal. Another preferred embodiment of a reaction station is a station comprising an incubator. Preferably, said incubator is a temperature-controlled incubator. More preferably, said incubator is held at one constant temperature. Another preferred embodiment of an incubator is a thermocycler block. Preferably, a detector for detecting the detectable signal is integrally connected to the reaction station, more preferably to the incubator as hereinbefore described. A preferred detector comprises a nucleic acid quantification system for periodic measurement and quantification. More preferably, the detector additionally comprises a nucleic acid detection system which detects the signal and ascertains the presence or absence of the nucleic acid in the reaction receptacle based upon whether or not a signal above a threshold level is detected.

Alternatively, the automated analyzer additionally comprises a detecting station. The automated analyzer further comprises a transport mechanism. Said transport mechanism comprises a handler for handling consumables. Said handler preferably transports a consumable between stations. In one embodiment, said transport mechanism is constructed and arranged to transport said sample vessel and said rack from said sample dispensing station to said separation station. Further preferred embodiments of the automated analyzer herein described are individual or combined features disclosed herein.

In a preferred embodiment, the analytical apparatus (400) comprises at least one module (401) for processing an analyte, said processing comprising pipetting of a liquid. The processing module (401) comprises:
a) a process head (35) for engaging with pipette tips (3, 4), said process head (35) comprising positioning elements (36) arranged in the lower surface (61) of said process head (35),
b) a tip rack (60, 70) holding pipette tips (3, 4), wherein said tip rack (60, 70) comprises positioning elements (31, 32, 33, 34) capable of engaging mechanically with the positioning elements (36) on the process head (35).

In a preferred embodiment of the analytical apparatus (400) hereinbefore described, said processing module (401) is a module for isolation and purification of an analyte. Therefore, the term "processing" as used herein is understood to relate to isolation and/or separation and/or capture and/or purification of an analyte. Preferably, said apparatus (400) comprises a module for preparing samples for processing (402). Preferably, said apparatus (400) comprises a module for amplification of said analyte (403). In one preferred embodiment, said apparatus additionally comprises a module (404) for transferring amplification reagents from a storage receptacle to a receptacle comprising a purified analyte. Further preferred embodiments of said apparatus are as hereinbefore and hereinafter described.

An automated analyzer (400) for use in performing a nucleic acid based amplification reaction is also disclosed. Said analyzer comprises a plurality of modules (401, 402, 403). One module is a processing module disposed at a first location within the analyzer constructed and arranged to separate a nucleic acid from other material in a sample. Said processing module comprises a separation device as herein described. The analyzer further comprises an amplification module disposed and arranged at a second location within the analyzer. The amplification module comprises a temperature-controlled incubator for incubating the contents of at least one receptacle, preferably of a multiwell plate comprising the separated nucleic acid and one or more amplification reagents for producing an amplification product indicative of the target nucleic acid in the sample.

Figure 47A:
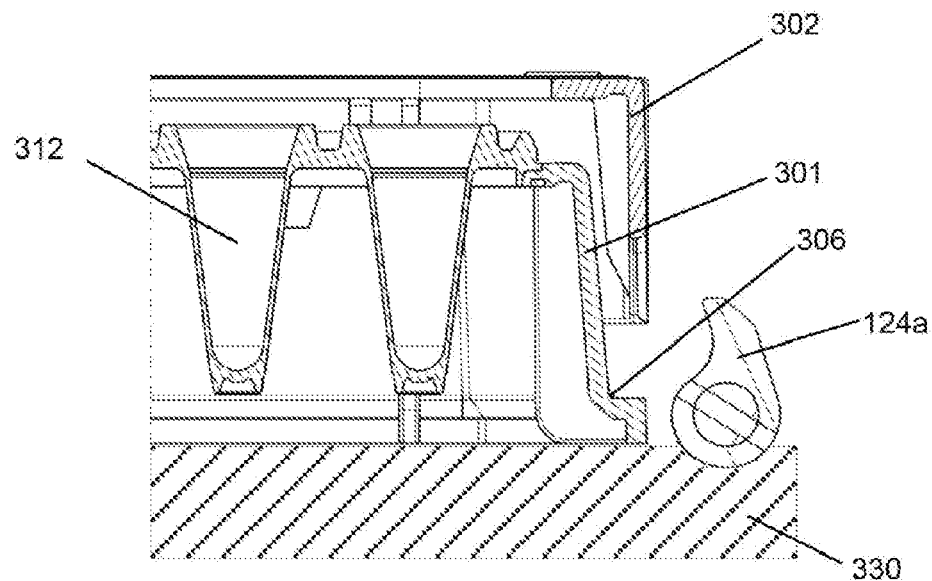
FIGS. 47 (a) and (b) show the fitting of the AD plate in a station for receiving the AD plate with the locking mechanism disengaged (FIG. 47a) or engaged (FIG. 47b).
Figure 47B:
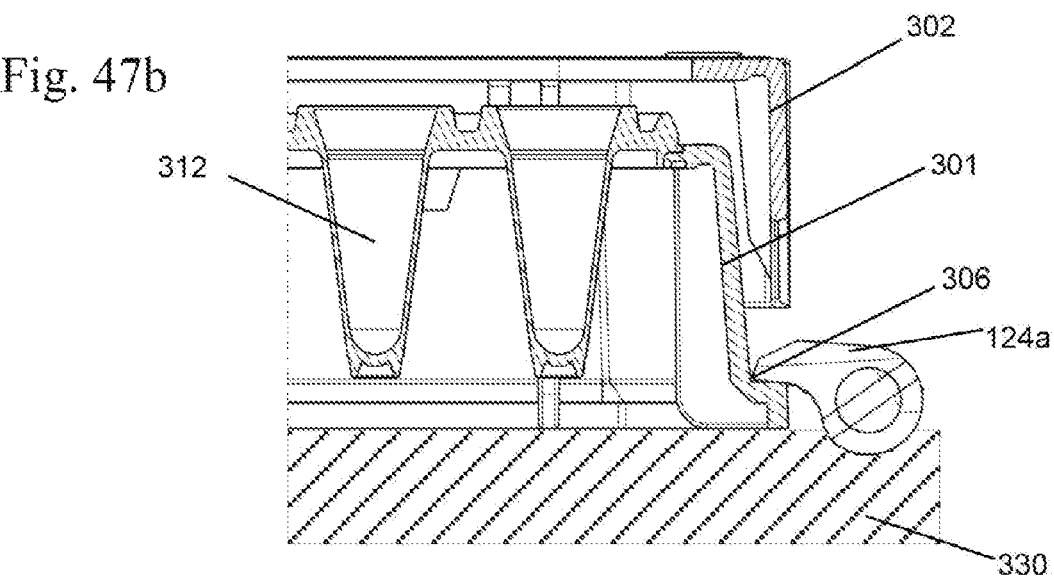

An analytical system comprising a holding station and a multiwell plate set as described herein is a further preferred embodiment of the analytical system disclosed herein. Preferably, said multiwell plate set is fixed in said holding station. Preferably, the multiwell plate comprises a base with a rim which comprises recesses, wherein a positioning and fixing element, preferably a latch-clip (FIGS. 47 (*a*) and (*b*)), on said holding station contacts said recesses, wherein said contact exerts a downwards pressure on the base of the multiwell plate, thereby fixing the multiwell plate in the holding station. Further preferred embodiments of the analytical system comprise individual or combined features described herein.

Furthermore, an analytical instrument is disclosed comprising:
a processing module for isolating and purifying an analyte comprising a holding station (470) for holding a rack comprising pipette tips, said rack comprising at least one recess located on one side wall of the rack, and at least one recess located on an opposite second side wall of said rack, wherein said holding station comprises a fixing element, preferably a latch-clip and wherein said fixing element, preferably a latch-clip interacts with said recess by exerting a force against the bottom of said recess; and
a module (403) for analyzing said purified analyte by reacting said analyte with reagents necessary to obtain a detectable signal.

Figure 38:
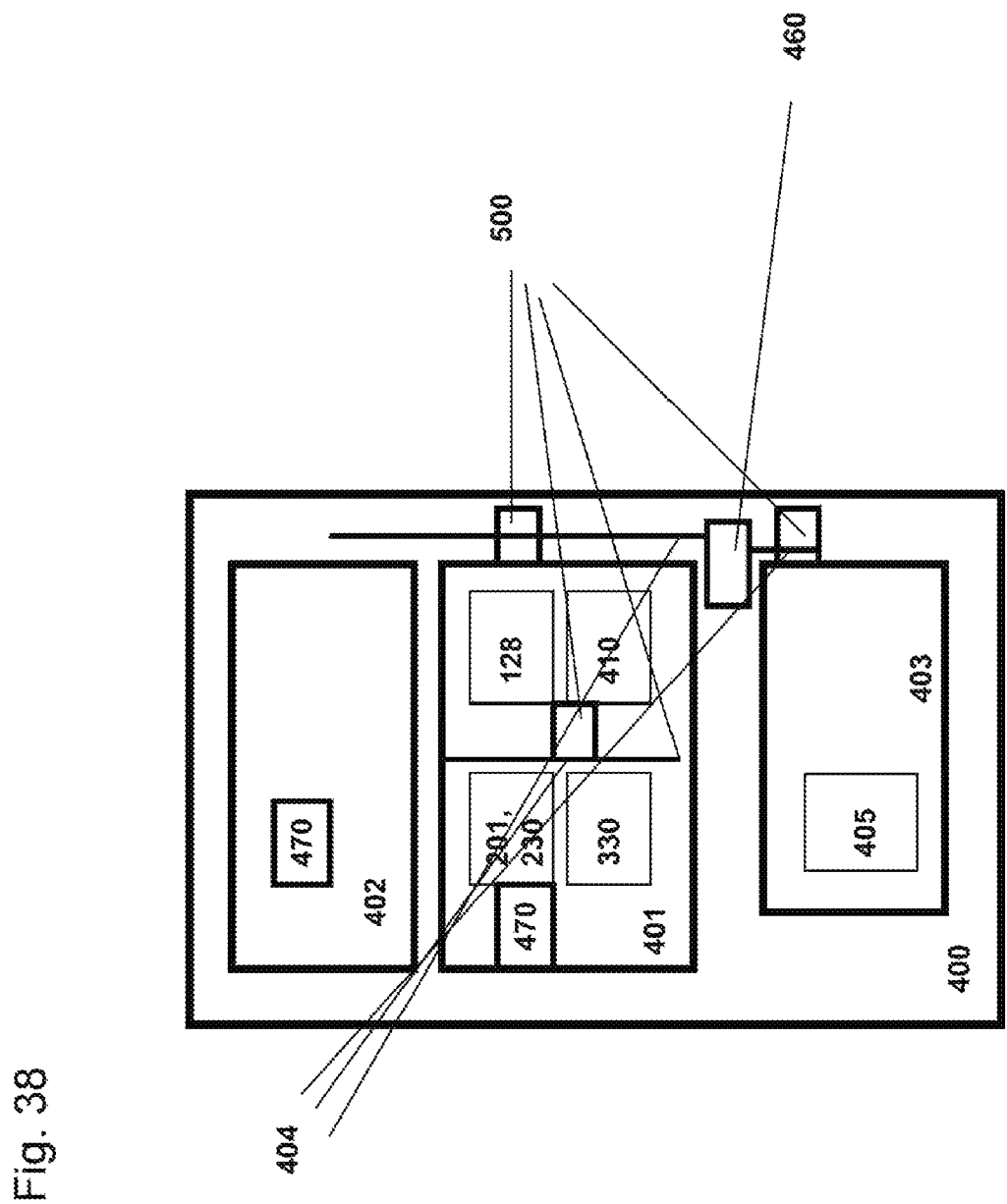
FIG. 38 shows schematic drawings of an analyzer comprising different stations, modules or cells.
Figure 51:
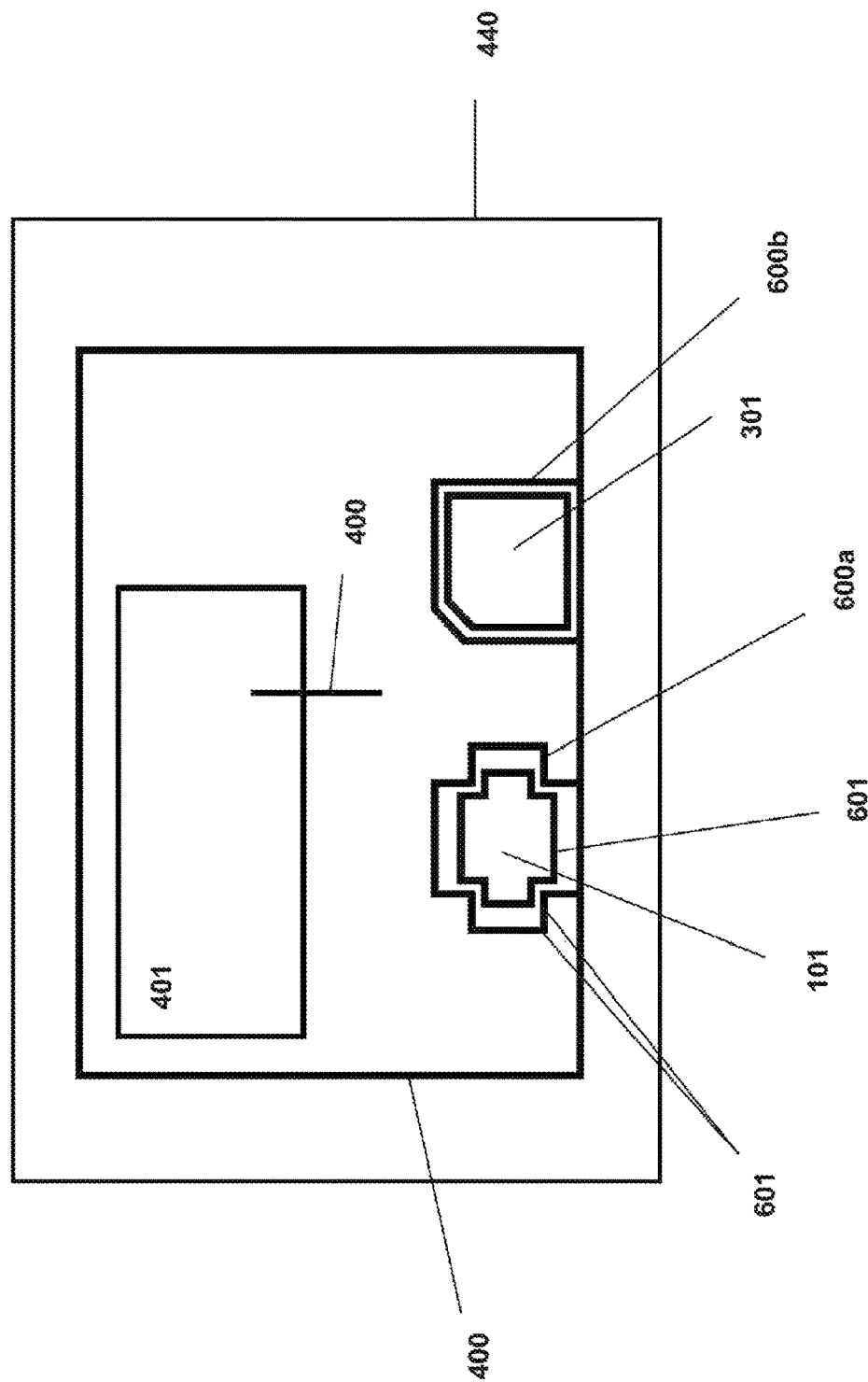
FIG. 51 is a schematic drawing of an analyzer embodiment with stackers which specifically recognize certain consumables.

The analytical instrument preferably additionally comprises a liquid handling module (404, 500). Further embodiments and preferred embodiments of the analytical instrument are described herein, either separately or as combinations of embodiments. Preferred embodiments of analyzers are shown in FIGS. 38 and 51.

The analytical instrument disclosed herein preferably additionally comprises a sealing station (410). The sealing station (410) is preferably located in the process module (401).

The term "module" and "cell" are used interchangeably herein.

Tip Rack

A tip rack is disclosed. Such tip racks comprise pipette tips. Tip racks are commonly used in analytical systems for providing pipette tips for pipetting liquids to the system. Such tips are disposable, but can be re-used at least once. Said tip rack comprises independent chambers for accommodating pipette tips.

A preferred rack is disclosed for holding pipette tips. Said rack comprises independent chambers for accommodating at least a first type of pipette tips and a second type of pipette tips. In one embodiment, said rack comprises more than one part. In another embodiment, said rack is an integral one part rack. Preferably, the volume of the first type of pipette tips is at least 1 ml and the volume of the second type of pipette tips is below 1 ml. More preferably, the volume of the first type of pipette tips is between 1 ml and 1.5 ml, and the volume of the second type of pipette tip is between 10 ul and 600 ul.

Preferably, the first type of pipette tips and the second type of pipette tips are stored in said rack in alternate rows. In one embodiment, the rack comprises 48 pipette tips of a first type and 48 pipette tips of a second type. Other numbers of tips are, however, also encompassed. The rack may also comprise more pipette tips of one type than of the other type.

In one embodiment, the independent chambers are vessels.

A three part rack is disclosed for holding pipette tips. Said rack comprises features which make it particularly suited for automated systems. Said rack comprises three parts. An upper rack comprises a surface plate, said surface plate comprises through bore-holes with a seating area for inserting pipette tips in said rack. The rack also comprises a lower rack. Said lower rack comprises independent chambers for accommodating pipette tips of a first type. The third part of said rack is an insert rack. The insert rack is inserted into said lower rack. The insert rack comprises chambers for accommodating pipette tips of a second type. The upper rack is assembled on top of said lower rack and said insert rack.

The rack is, thus, suited for holding more than one type of pipette tips. This is useful in systems in which different volumes of liquid are pipetted with pipette tips.

The rack disclosed herein comprises contamination protection for protecting individual tips from contaminating each other. Such contamination may occur due to droplets or aerosols. Such protection is of particular importance if pipette tips are place in the rack after a first use, before being re-used again. Thus, the rack preferably comprises rows of open chambers for holding a second type of pipette tips. More preferably, said open chambers have a bottom. This bottom separates the chamber holding the second type of pipette tips from the chambers holding the first type of pipette tips. This reduces the risk of contaminations between the first and second types of tips.

In a preferred embodiment, said rows of open chambers for holding pipette tips of a second type alternate with rows of independent chambers for accommodating said pipette tips of a first type. Preferably, the inner area of the independent chambers in the lower rack for accommodating said pipette tips of a first type is larger than the inner area of the through bore holes for inserting pipette tips.

In a preferred embodiment, a wall located on the inside of the side walls of the independent chambers of the lower rack for holding pipette tips of a first type extend from the bottom of the lower rack to below the top of the side wall of the independent chambers of the lower rack. Preferred embodiments described hereinbefore and hereinafter relate to a rack comprising pipette tips of a first type, more preferably additionally comprising a second type of pipette tips.

Further preferred embodiments of any one tip rack disclosed herein comprise features described above and below without limitation to one specific embodiment by combination with any one of the embodiments disclosed herein.

A first embodiment of an exemplary rack (60) (FIGS. 1 and 2) comprises multiple parts. An upper rack (1), a lower rack (2) and an insert rack (14) are assembled to one rack for holding and re-using tips (4). In a preferred embodiment, a first type of tips (4) and a second type of tips (3) are held in said rack (60). In a more preferred embodiment, tips (4) for sampling, isolating and purifying an analyte and tips (3) for transferring the eluted analyte are held in one rack according to the invention. Most preferably, the rack (60) elongated tips with a large volume (4) and short tips with a small volume (3). Preferred embodiments of the three parts of racks are described hereinafter.

Upper Rack (1)

Figure 9:
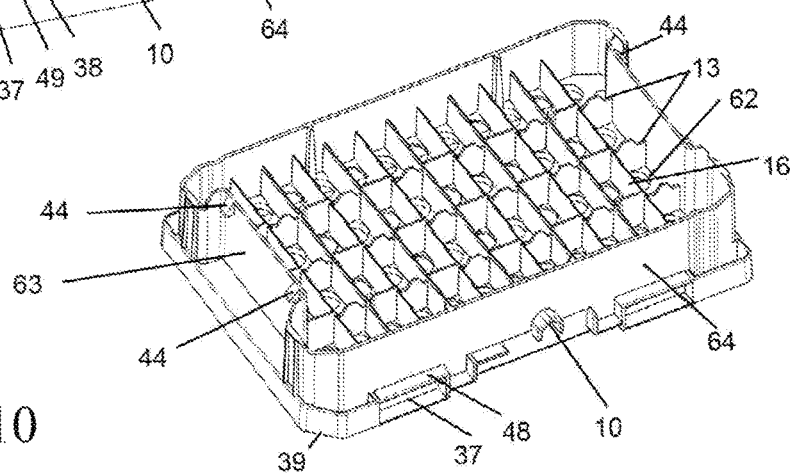
FIG. 9 shows a perspective view of the bottom part of the upper rack.
Figure 10:
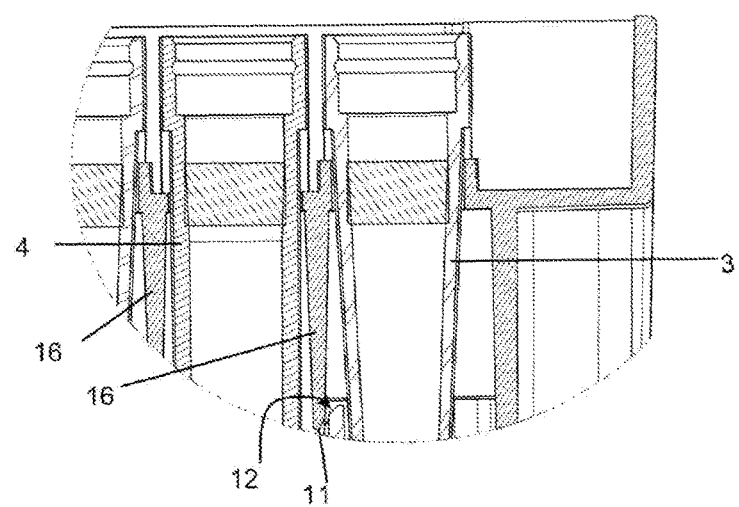
FIG. 10 shows a partial cross-sectional view through the assembled rack with pipette tips loaded.

Upper rack (1) comprises a frame (50) and a surface plate (51) located inside said frame (50) (FIG. 9, FIG. 10). Said surface plate (51) comprises through bore-holes (23, 25) (FIG. 4). On the bottom side (62) of said plate (51), separation walls (16) and separation lamellae (18) are located between through bore-holes (23, 25). They provide additional protection against contamination between tips (3, 4) and confer additional stability on the upper rack (1). Certain separation walls (16) also comprise a recess (13). Said recess (13) allows the separation walls (15) of the insert rack (14) to engage with separation walls (16) of the upper rack (1) in an overlapping way for sealing against horizontal flying drops in case of exploded bubbles during tip handling with tip (4). Preferably, separation lamellae (18) with recess (13) alternate with separation lamellae (18) without recess.

Lower Rack (2)

Figure 5:
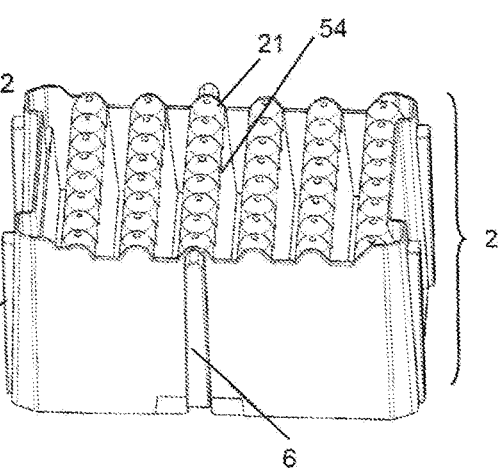
FIG. 5 shows a perspective view of the bottom part of the lower rack.
Figure 6:
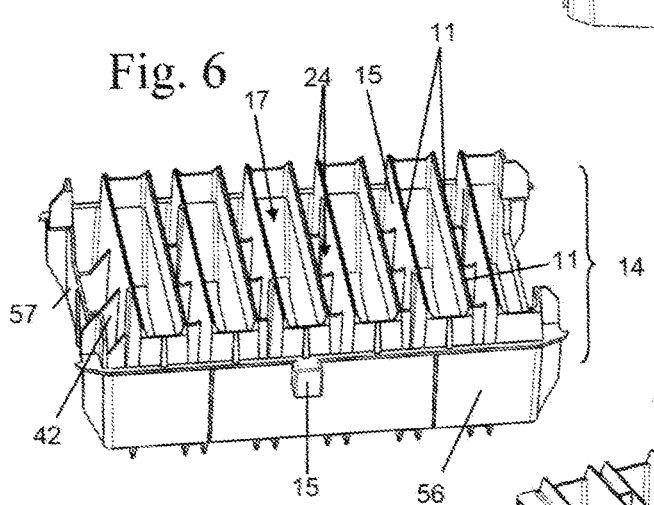
FIG. 6 shows a perspective view of the top-side of the insert rack.

Lower rack (2) comprises two long side walls (52) located opposite each other, and two short side walls (53) located opposite each other (FIGS. 5 and 6). Each short side wall (53) contacts both long side walls (52) to form a frame. The inside space defined by said side walls (52) and (53) comprises chambers (19) which are formed by interior dividing walls (54) with ridge (9) and perpendicular to said walls (54) second walls (55). The chambers (19) comprise bottoms (21) which are preferably rounded.

Lower rack (2) comprises, on the outside of walls (52) and (53), stacker-guiding elements (6) and (7) which, preferably, are also hardware identifiers.

Insert Rack (14)

Figure 7:
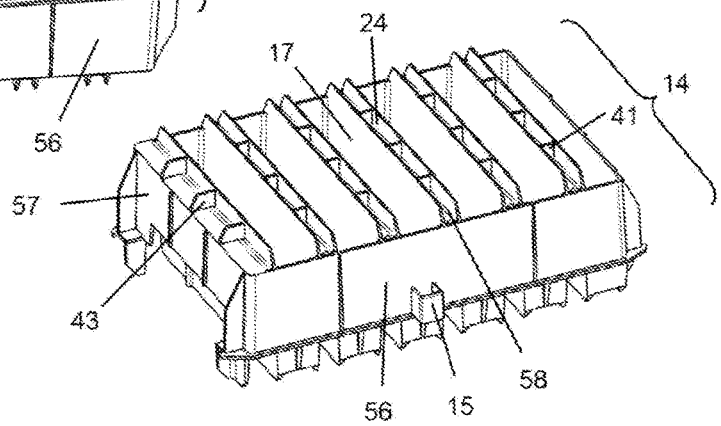
FIG. 7 shows a perspective view of the bottom part of the insert rack.
Figure 8:
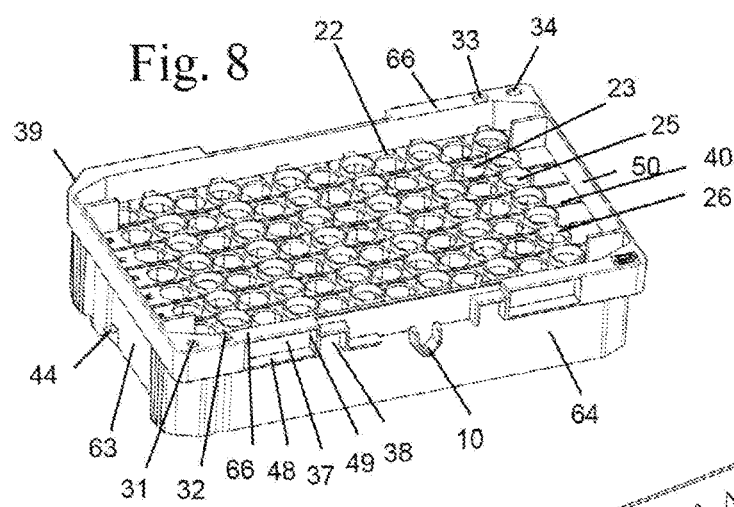
FIG. 8 shows a perspective view of the top-side of the upper rack.

Insert rack (14) comprises two long front walls (56) and two short side walls (57). Chambers (24) are formed by separation walls (15) which are arranged parallel to the short side walls (57) (FIG. 7, FIG. 8). These chambers (24) have bottoms (58) and can accommodate the second type of tips (3). Between each chamber (24) is a passage way (17) for a first type of tip (4) which extends into the chambers (19) of the lower rack (2). Chambers (24) preferably comprise stabilizing ribs (41). The insert rack (14) preferably comprises additional stabilizing ribs (42, 43)

Combo-Tip Rack

The multiple part construction of the rack (60) has several advantages. One advantage is that tips (4) with an elongated shape for pipetting large volumes can be stored in independent, closely packed chambers (19). The tips (4), thus, require only a limited space in a horizontal plane for storage, while being able to hold large volumes of liquid. Views of a preferred embodiment are shown in FIGS. 1 to 24.

As a further advantage, the inside horizontal cross section area of the chambers (19) for tips (4) is larger than the cross section of the through bore holes of the seating area (22) (FIG. 3). This results in a prevention of capillary forces which may lead to transport of liquid between the chambers (19).

Figure 24:
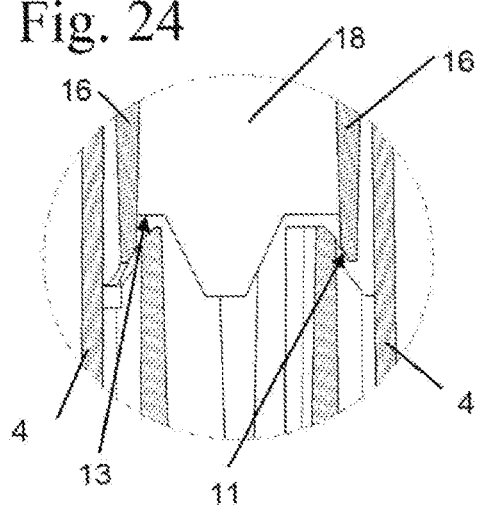
FIG. 24 shows a sectional view of the site of interaction between the upper rack and the insert rack without a second type of pipette tip inserted into a through bore-hole.

Yet another advantage of the construction of the tip rack (60) is that the inner walls (54) of the chambers (19) are not continuous from the bottom (21) of the chamber (21) to the seat area (22) (FIG. 3). Thus, the transport of liquid from the bottom (21) of the chamber (21) to the seat area (22), and, thus, contamination is prevented. This makes re-use of the pipette tips (4) possible. In addition, chambers (19) comprise a wall (5) located on the inside surface (65) (FIG. 24). Said wall (5) preferably covers only part of the height of chamber (19). More preferably, said wall (5) extends from above the bottom (21) of chamber (19) to below ridge (9) of the inside surface (65) of walls (54) of the lower rack (2). Said wall (5) further prevents capillary effects in chamber (19).

Yet another advantage of the construction of the tip rack (60) is that two different types of tips can be stored in it (FIG. 3). In the present preferred embodiment, a second type of tip (3) is stored in the tip rack (60). The second type of tip is shorter than the first type of tip, and is used to pipette smaller amounts of liquid than is pipetted by the first type of pipette tip. In the present preferred example, the second type of tips is stored in chambers (24) within the insert rack (14) which are located on a higher level than chambers (19) and are hermetically separated from chambers (19), but are open within one row of chambers (24). One advantage of this construction is that it is space saving. In addition, with the chambers (24) located in the insert rack, there is more space available for preventing contamination, e.g. by capillary force, between the chambers (19) of the first type of tips (4). In a preferred embodiment, only the first type of tips (4) is re-used, while the second type of tips (3) is used only once.

Figure 23:
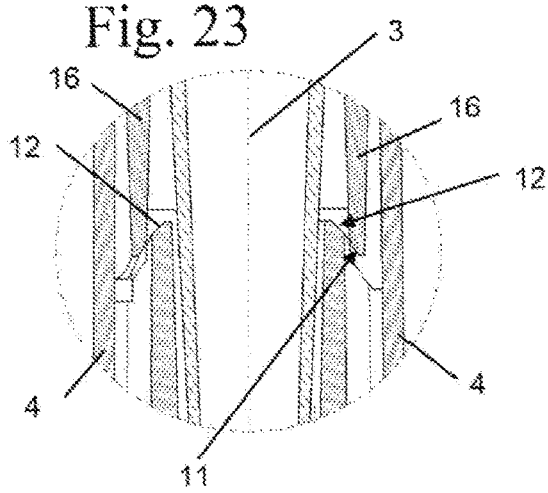
FIG. 23 shows a sectional view of the site of interaction between the upper rack and the insert rack with a second type of pipette tip inserted into a through bore-hole.

Insert rack further comprises ridges (8) on the bottom of chambers (24) (FIG. 3). These ridges (8) prevent splashes of liquid which may be caused by blisters of liquid forming on the tip-end of pipette tip (4) and bursting at the height of ridges (8) from passing into the neighboring chambers (19). The lower rack (2) comprises, at the top of the walls (54) between chambers (19), a ridge (9). Ridge (9) has the same function as ridge (8). Ridge (9) and ridge (8) do not contact each other (FIG. 23). This prevents capillary effects.

When stored in the rack (60), the tips (3, 4) sit on the seating area (22, 26) of a through bore-hole (25, 23) (FIG. 13, FIG. 14). The through bore-holes (25, 23) are located on a seat area (22, 26). Preferably, the seating area (22) of the through bore-holes (25), is elevated compared to the seating area (26) of the through bore-holes (23) of the first type of tips (4). This has the advantage that when the first type of tips (4) is either replaced in the rack or re-engaged for re-use, in case liquid from the first type of tips (4) contacts the seating area (22) of through bore-hole (25), the liquid can not ascend from the lower seat area (22) to the higher seat area (26), thus preventing contamination of the second type of tips (3).

Preferably, additional capillary channels (40) separate neighboring through bore-holes (23) at the level of the lower seat area (22) and drain off any liquid contacting the lower seat area (22) or the through bore-holes (23) (FIG. 4, 9, 13, 14). This prevents contamination of neighboring through bore-holes (23, 25). An additional advantage of the capillary channels (40) is that the liquid is distributed over a larger area and can evaporate more quickly.

Figure 15:
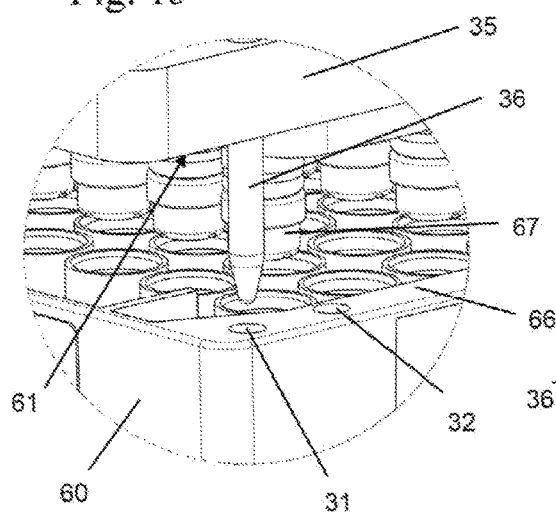
FIG. 15 shows a detailed perspective view of the alignment of the positioning elements on the bottom of the process head and the positioning elements on the top of the upper rack for alignment of the process head with the first type of pipette tips.
Figure 16:
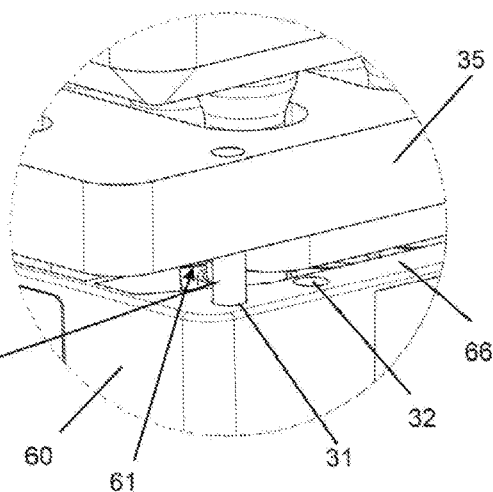
FIG. 16 shows a detailed perspective view of the engagement of the positioning elements on the bottom of the process head and the positioning elements on the top of the upper rack.

In a preferred embodiment, the pipette tips comprise a receiving ridge (27, 28) which contacts the seating areas (22, 26) of the through bore-hole (23, 25) when the pipette tip (3, 4) is seated in the rack (60) (FIG. 15, FIG. 16). More preferably the second type of tips (3) has a shorter receiving ridge (27) than the first type of tips (4). The difference in height between receiving ridge (27) and (28) is equal to the difference in height of the rim of through bore holes (23) and (25). This has the advantage that all pipette tips (3, 4) are on the same level for engagement with the process head (35), but at the same time, the second type of pipette tips (3) can be seated on a higher level on the rack to prevent contamination by liquid from the first type of tips (4). In addition, it provides a visual control for the correct assembly of first and second types of pipette tips (3, 4) in the rack (60) since the top surface of tips (3, 4) seated in the wrong position would be at a lower or higher level than the correctly seated tips (3, 4).

The receiving ridges (27, 28) on the tip (3, 4) do not comprise a continuous circumferential seating base (59) for contacting the rim of through bore-hole (23, 25). The seating base (59) only has punctual sites of contact with the seating areas (22, 26). One advantage is that less material is used for the tip (3, 4) and that the tip (3, 4) can be produced with higher precision and with less strain. The reduced area of contact between the tip (3, 4) and the seating area (22, 26) has the additional advantage that electrostatic charge of the tips (3, 4) is reduced.

Tips (3, 4) are matted in the area of shaft (29) with a surface roughness of 0.8 to 1.6 urn, and polished in the area of the tip-end (30). The matted surface of the shaft (29) allows droplets of liquid to lie flat on the surface and to evaporate more quickly. Thus, when tip (4) is inserted into the through bore-hole (23, 25) no or less liquid can be wiped off if the tip (4) contacts seating area (22, 26), and, thus, the risk of contamination is reduced. The polished tip-end (30) causes droplets of liquid to stay on the tip-end (30) in a pearl-type manner and to be wiped off the tip-end (30) when the tip (4) submerges from a liquid. The tip-end (30), thus, remains without liquid attached.

Figure 17:
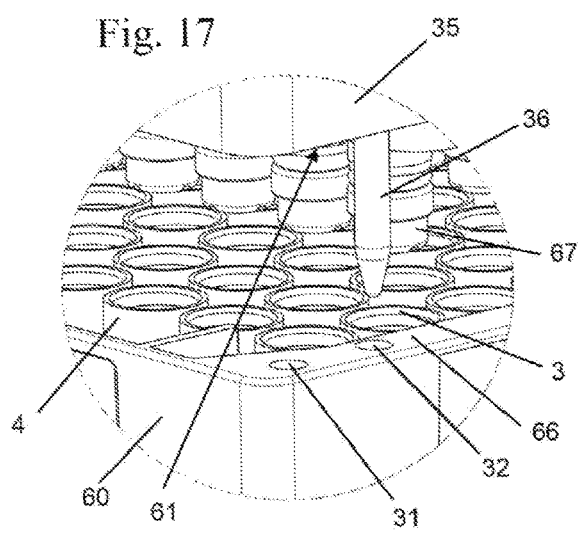
FIG. 17 shows a detailed perspective view of the alignment of the positioning elements on the bottom of the process head and the positioning elements on the top of the upper rack for alignment of the process head with the second type of pipette tips.
Figure 18:
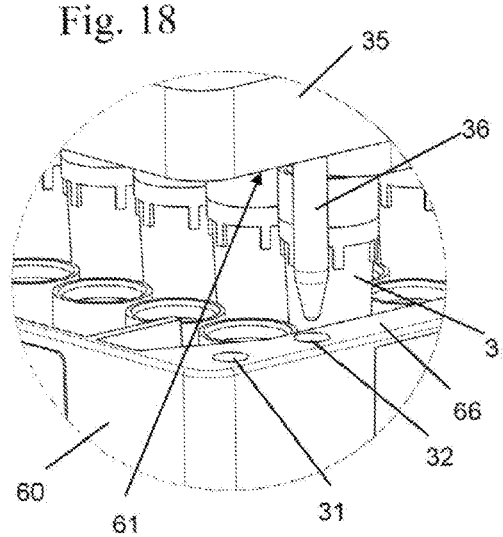
FIG. 18 shows a detailed perspective view of the process head following engagement of the second type of pipette tips.

The upper rack (1) preferably comprises a first type of positioning elements (10) (FIG. 21, FIG. 22) and a second type of positioning elements (31, 32, 33, 34) (FIG. 17, FIG. 18). The first type of positioning elements (10) allows an approximate positioning of the rack (60) relative to a process head (35), while the second type of positioning elements (31, 32, 33, 34) allows a precise positioning of said rack (60) relative to the process head (35). The approximate positioning by the first type of positioning elements (10) ensures that the second type of positioning elements (31, 33) or (32, 34) are aligned with counter-positioning elements (36) on the process head (35). The advantage of the two types of positioning elements is that the positioning of rack (60) and process head (35) for tip engagement is fast and precise.

The second type of positioning elements (31, 33) or (32, 34) are preferably located on the top surface (also referred to as surface plate) (51) of the rack (60) (FIGS. 17 to 20). The counter-positioning elements (36) are preferably located on the bottom surface (61) of the process head (35).

Figure 19:
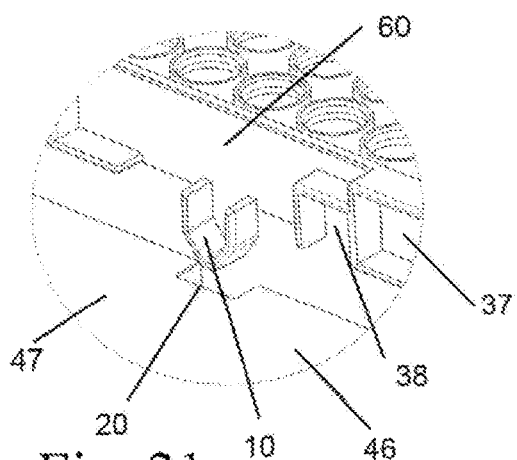
FIG. 19 shows a perspective view of the positioning elements on a side wall of the rack and on the process deck for initial positioning of the rack within the analyzer.
Figure 20:
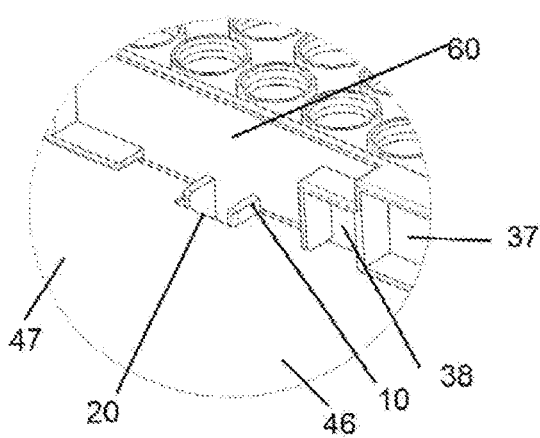
FIG. 20 shows a perspective view of the engagement of positioning elements on a side wall of the rack and on the process deck for initial positioning of the rack within the analyzer.
Figure 21:
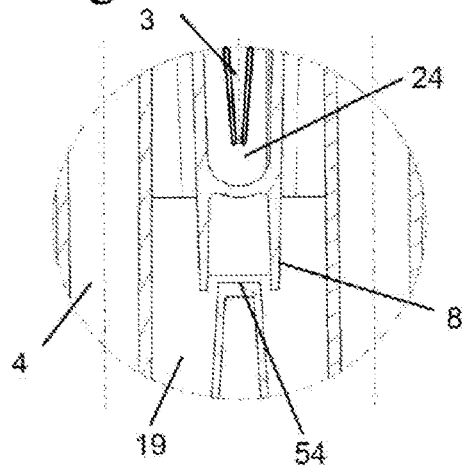
FIG. 21 shows a detailed sectional view of the bottom of a chamber for accommodating the second type of pipette tips in the insert rack and the ridge between two chambers of the lower rack.
Figure 22:
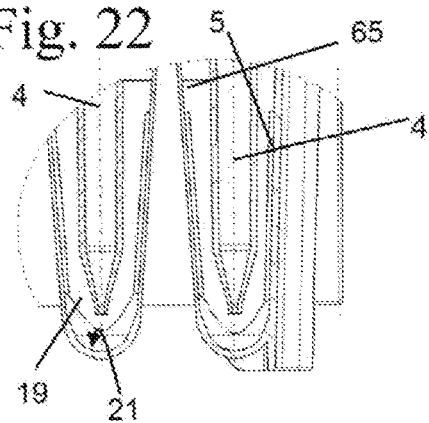
FIG. 22 shows a detailed sectional view of the bottom of chambers of the lower rack.

In a preferred embodiment, the positioning elements (31, 33) engage with counter-positioning elements (36) on the process head (35) to align the first type of pipette tips (4) with the interface on the process head (35) (FIG. 17, FIG. 18). Alternatively, positioning elements (32, 34) engage with counter-elements (36) on the process head (35) to align the second type of pipette tips (3) with the interface (67) of the process head (35) (FIG. 19, FIG. 20).

In a preferred embodiment, the positioning elements are openings (31, 32, 33, 34) in the top surface (51) of the rack (60), preferably located in opposite corners of the top surface (51) of the rack (FIG. 1). The counter-positioning elements, in this preferred embodiment, on the bottom surface (61) of the process head (35) are rods (36) located in the corresponding corners of the process head (35). Openings (31, 32, 33, 34) and rods (36) are constructed such that rods (36) can engage with openings (31, 32 or 33, 34) for precise alignment of rack (60) and process head (35). Thus, the tip (3, 4) and the interface (67) on the process head (35) for engagement of the tips (3, 4) are precisely aligned, and the interface of the process head (35) can engage the tip (3, 4). In a more preferred embodiment, two of the openings (31, 32) have a circular cross-section for precise positioning, in a horizontal plane. Openings (33, 34) have an elongated shape for compensation of manufacturing tolerances. This is advantageous because the rack (60) can be precisely positioned without canting with the process head (35).

The footprint of the rack preferably comprises a length and width of the base comprises a length and width of the base essentially corresponding to ANSI SBS footprint format. More preferably, the length is 127.76 mm+/−0.25 mm, and the width is 85.48 mm+/−0.25 mm. The rack (60) comprises form locking elements (38) for interacting with a handler (500). The rack (60) can be gripped, transported and positioned quickly and safely at high speed while maintaining the correct orientation and position.

The term "essentially corresponding to ANSI SBS footprint format" means that the base of any one consumable may have cut our sections, e.g. cut corners. Thus, the surface geometry of different types of consumables with ANSI SBS footprint format can be different. However, the base of any one consumable fits into a station which has a corresponding receiving part in ANSI SBS footprint format.

The rack (60) comprises one or more hardware-identifiers (39), wherein said hardware identifiers (39) are an integral part of the consumable. The rack (60) further comprises stacker guiding elements (6, 7). Said hardware identifiers (39) and stacker guiding elements (6, 7) comprise ridges and/or recesses on the side walls of the consumables, wherein said pattern of ridges and/or recesses is unique for a specific type of consumable, preferably the rack (60). The stacker guiding elements (6, 7) and hardware-identifiers (39) ensure that the user can only load the rack (60) into the appropriate stacker position of an analytical instrument (46).

The rack (60) also comprises recesses (37) in the side wall of the upper rack (1). The recesses (37) comprise a bottom wall (48) and side walls (49). The rack (60) is positioned inside an opening in an analytical instrument (46). When the rack (60) is positioned, the bottom wall (48) of recess (37) contacts the surface of the process deck (47) of the analytical instrument (46). Said recesses (37) engage with counter elements on an analytical instrument (46) to hold down the rack (60) in the instrument. This allows for additional stabilization of the rack (60) inside the analytical instrument (46).

Figure 25:
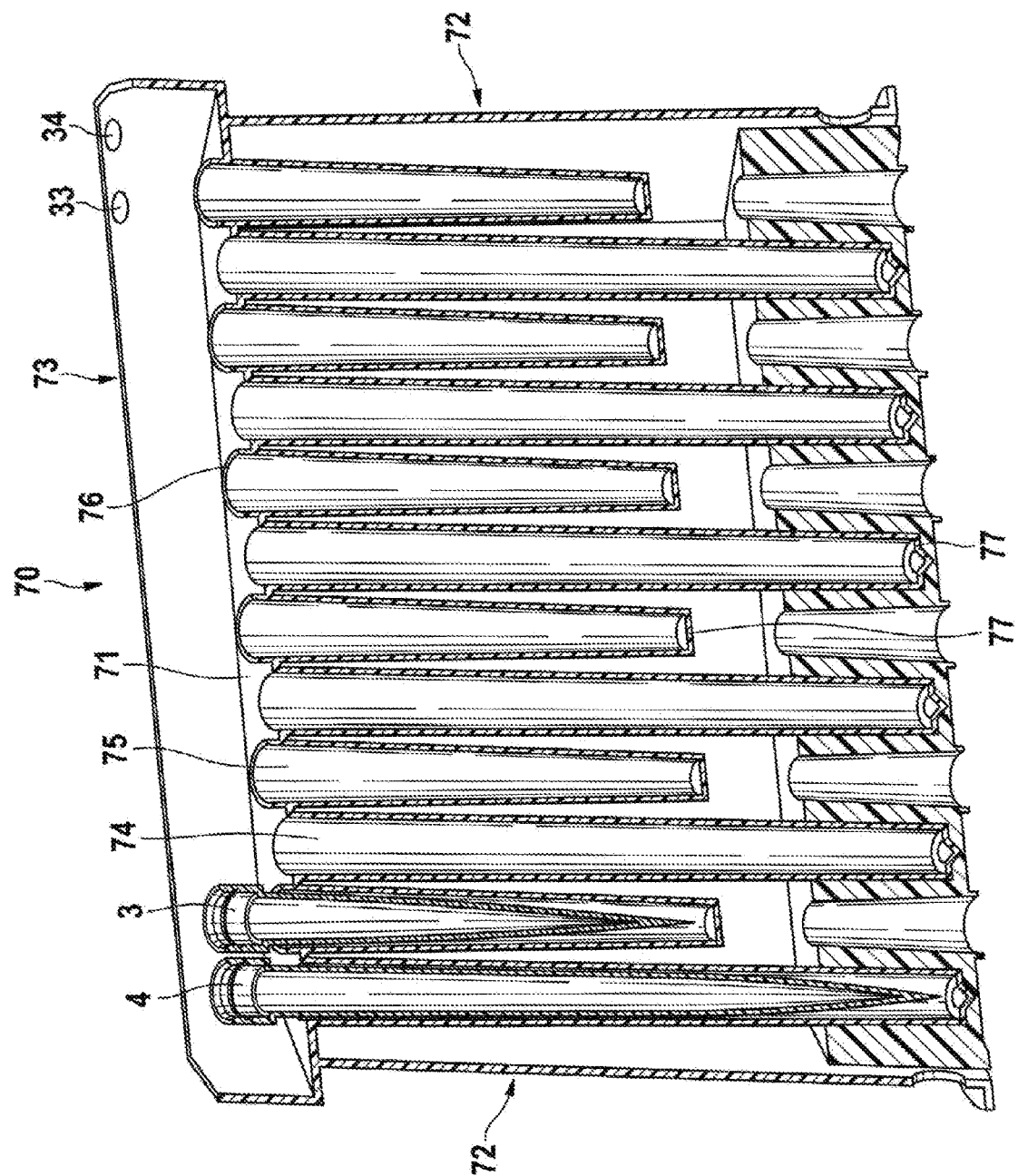
FIG. 25 Partial view of a second embodiment of tip rack.

The insert rack (14) comprises an external centering surface (11) which interacts with internal centering surface (12) on the upper rack (1) to allow centering during assembly of the rack (60) (FIG. 11, 12; FIGS. 25 to 26).

Upper rack (1) and lower rack (2) are fixed during assembly, preferably by a snap-fit (44) located on either one of two opposite side walls (63, 64) of the frame of the upper rack (1) and a snap groove (45) located on either one of two corresponding opposite side walls of the lower rack (2).

A second embodiment of an exemplary rack is an integral one part tip rack (70) comprising a top surface (71), two opposing short (72) and two opposing long (73) side walls (FIG. 25). The tip rack comprises vessels (74, 75) for holding pipette tips (3, 4). Said vessels (74, 75) comprise an open top (76) and a closed bottom (77). Any one vessel (74, 75) can hold one tip (3, 4). The footprint of the rack (70) preferably comprises a length and width of the base essentially corresponding to ANSI SBS footprint format. More preferably, the length is 127.76 mm+/−0.25 mm, and the width is 85.48 mm+/−0.25 mm. Preferred embodiments of said second embodiment comprise hardware identifiers (6, 7, 39), recesses (37) to engage with counter elements on an analytical instrument to hold down the rack in the instrument as described for the first embodiment of said rack. Preferred embodiments also comprise positioning elements (31, 32, 33, 34, 10) as described for the first embodiment of the rack (60).

Positioning of Process Head and Tip Rack

Analytical systems used in the field of diagnostics require processing of samples to be analyzed. Such processing involves transfer of vessels, or of liquid samples and reagents from one vessel to another. For higher throughput, simultaneous processing is often performed with processing devices which can handle multiple consumables simultaneously. Engagement of process device and consumables requires proper alignment.

U.S. Pat. No. 6,846,456 discloses an assay work station. Process head (400) is aligned with pipette tips (362) or receptacles (262) which are held by racks (302) or (202) by engagement of rods (408), (410) located on the process head (400) with guide holes (510), (512) located on guide supports (500). Guide supports and racks are separately mounted on a base structure (100).

The disadvantage of the prior art is that a multitude of positionings influence the alignment of process device and consumable. Imprecisions of positionings caused by imprecise manufacturing or mounting of the positioning elements or guide supports with the positioning elements or the racks (302), (202) can impair the precision of the alignment of process device and consumable.

A positioning method for aligning a rack and a process device is also disclosed. The positioning method comprises aligning at least two positioning elements located on the bottom surface of said process device with at least two positioning elements located on the top surface of said rack, and mechanically engaging said positioning elements on the process device with the positioning elements of the rack. Process devices preferably relate to pipettor for engaging with pipette tips to pipette liquids. Such process heads are well known in the art.

Preferably, said consumable is a tip rack comprising pipette tips, and said process device is a process head comprising an interface for engaging with pipette tips. The pipette tips are preferably arranged in a 2-dimensional array in said pipette rack.

The engagement of the positioning elements on the process device and the positioning elements on the consumable cause the interface of the process device to interact and engage with the pipette tips.

A "rack" is understood to be any type of device used in an analytical system which holds a sample, a device which holds a consumable which is constructed and arranged to hold a sample. The rack has a top surface and four sidewalls, wherein two side walls are parallel and opposing each other. Optionally, the rack also has a bottom surface. A consumable is understood to be a device which is introduced recurrently to the analytical system for use in an analytical test. A consumable may be used a single time before being replaced, or it may be use multiple times. In one preferred embodiment, said rack holds vessels. Said vessels can hold a sample for use in an analytical system. Said sample is understood to relate to a sample to be processed in an analytical system, or a reagent to be used in an analytical system. Alternatively, said vessels are pipette tips for aspirating and dispensing liquids. Said liquids may be samples or reagents as defined hereinbefore. Thus, said rack may be a pipette tip rack. Preferred embodiments of said pipette tip rack include integrally formed racks or racks comprising more than one part, as shown in FIG. 25 or 1. A multiple part rack is described herein as a preferred, but not limiting example. In another preferred embodiment, the rack is a multiwell plate comprising vessels integrally attached to said rack.

A process device is any type of device used in an analytical system which is involved in the processing of a sample during an analytical test, and which requires alignment with a sample device. A preferred embodiment of a process device is a process head. A process head is understood to be a device which engages with pipette tips. Said device comprises an interface which can engage with said pipette tips. Preferably, said interface comprises cones. However, other interfaces known in the art are also included. In other embodiments, said process device may also include devices for gripping consumables. Preferred embodiments of interfaces are cones, cylindrical interfaces or interfaces with O-rings.

Positioning elements are understood to be elements located on the process device and on the rack. Said elements are constructed and arranged such that positioning elements on the process device can interact with positioning elements on the rack, thereby mechanically engaging the process device and the rack.

The process head preferably comprises a number of interfaces equal to the number of pipette tips of a first type. The process head can selectively engage with pipette tips of a first type or pipette tips of a second type. To achieve this, at least two positioning elements on the tip rack engage with at least two positioning elements on the process head such that the process head only engages with pipette tips of a first or with pipette tips of a second type. The selective engagement with pipette tips of different types can also be accomplished with a tip rack which comprises more than two types of pipette tips simply by choosing the appropriate number of positioning elements on the tip rack.

Preferably, one positioning element on the rack located in one corner has a first shape and the second positioning element on the rack which is mounted on the diagonally opposite corner of said top surface of said tip rack has a second shape. More preferably, the first shape is a circular cross-section and the second shape is an elongated shape. The advantages of this embodiment are further described below. In order to achieve a more reliable positioning, the method may also include a first positioning step, wherein the positioning elements located on the bottom surface of said process device and the positioning elements located on the top surface of said rack are aligned. Preferably, the first positioning is mediated by engagement of said positioning element with a notch.

Further preferred embodiments of the method disclosed herein are described hereinbefore and hereinafter.

In a preferred embodiment of the positioning method hereinbefore described, said tip rack (60, 70) comprises alternating rows of pipette tips of a first type (4) and pipette tips of a second type (3).

Preferably, said process head (35) comprises a number of interfaces (67) equal to the number of pipette tips of a first type (4). Said interfaces (67) may be conical or cylindrical, and may preferably comprise an O-ring. More preferably, at least two positioning elements (31, 32, 33, 34) on the tip rack (60, 70) engage with at least two positioning elements (36) on the process head (35) such that the process head (35) only engages with pipette tips of a first (4) or with pipette tips of a second (3) type. Further more preferably, said method additionally comprises a first positioning step, wherein the positioning elements (36) located on the bottom surface (61) of said process device (35) and the positioning elements (31, 32, 33, 34) located on a top surface (66) of said rack (60, 70) are aligned. Further preferred, said first positioning is mediated by engagement of a positioning element (10) with a notch (20). In a more preferred embodiment, said positioning elements (36) on the process device are pins, and said positioning elements (31, 32, 33, 34) on the top surface (66) of said rack are openings which are sized to engage with the pins. In a most preferred embodiment, the tip rack (60, 70) comprises four positioning elements (31, 32, 33, 34) and the process head (35) comprises two positioning elements (36).

In a preferred embodiment of the method hereinbefore described, said positioning elements (31, 32, 33, 34, 36) are located in diagonally opposite corners of said process device (35) or said rack (60, 70). However, other locations may be envisioned which lead to a similar result. Preferably, the tip rack (60, 70) comprises an equal number of first pipette tips (4) and second pipette tips (3). Most preferably, one positioning element (31, 32) on the rack (60, 70) located in one corner is a circular opening, and the corresponding second positioning element (33, 34) on the rack which is mounted on the diagonally opposite corner of the top surface of said tip rack (60, 70) is an oval opening.

Handler

A method for isolating and processing an analyte that may be present in a fluid sample is disclosed. The method comprises the automated steps of:

a) providing a fluid sample in a multiwell vessel in a first station;

b) combining together a solid support material and said fluid sample in a well of said multiwell vessel for a period of time and under conditions sufficient to permit said analyte to be immobilized on the solid support material;

c) isolating the solid support material from other material present in the fluid sample in a separation station;

d) and purifying the analyte in the separation station by separating the fluid sample from the solid support material and washing the materials one or more times with a wash buffer;

wherein said multiwell vessel is contacted by a handler and wherein said multiwell vessel is transported between stations by said handler, wherein said contact between said handler and said multiwell vessel is a form-locking contact.

Preferably, said multiwell vessel is a multiwell plate. Preferably, the method additionally comprises the step of analyzing the purified analyte in a analyzing station. More preferably, the analyzing is performed in a second multiwell plate.

Even more preferably, said second multiwell plate is contacted by at least one handler, preferably a handler, and transported between stations, wherein said contact between said handler and said multiwell vessel is a form-locking contact. Furthermore, the handler preferably transports the multiwell vessel between two stations, or between three stations. Said stations are preferably a storage station and/or a sample station and/or a separation station and/or a holding station and/or a sealing station and/or an analyzing station, and/or a detection station.

In a preferred embodiment, the method additionally comprises the step of providing pipette tips in a tip rack, wherein said tip rack is contacted by at least one handler and transported between stations, wherein said contact between said at least one handler and said tip rack vessel is a form-locking contact. One of the stations is preferably a storage station. Other preferred stations are the stations described herein.

In a preferred embodiment, said analyzing station is an amplification station. Preferably, the amplification station is an amplification and detection station. Preferably, the method additionally comprises the step of combining said purified nucleic acid with reagents sufficient for amplifying said analyte in a vessel of a multiwell plate, wherein said multiwell plate is held in a holding station. In a more preferred embodiment, one handler transports a multiwell vessel from a holding station to an air-lock (460), and a second handler transports said multiwell plate from said air-lock to said amplification station, wherein both handlers interact with said multiwell plate by a form-locking interaction.

Figure 48:
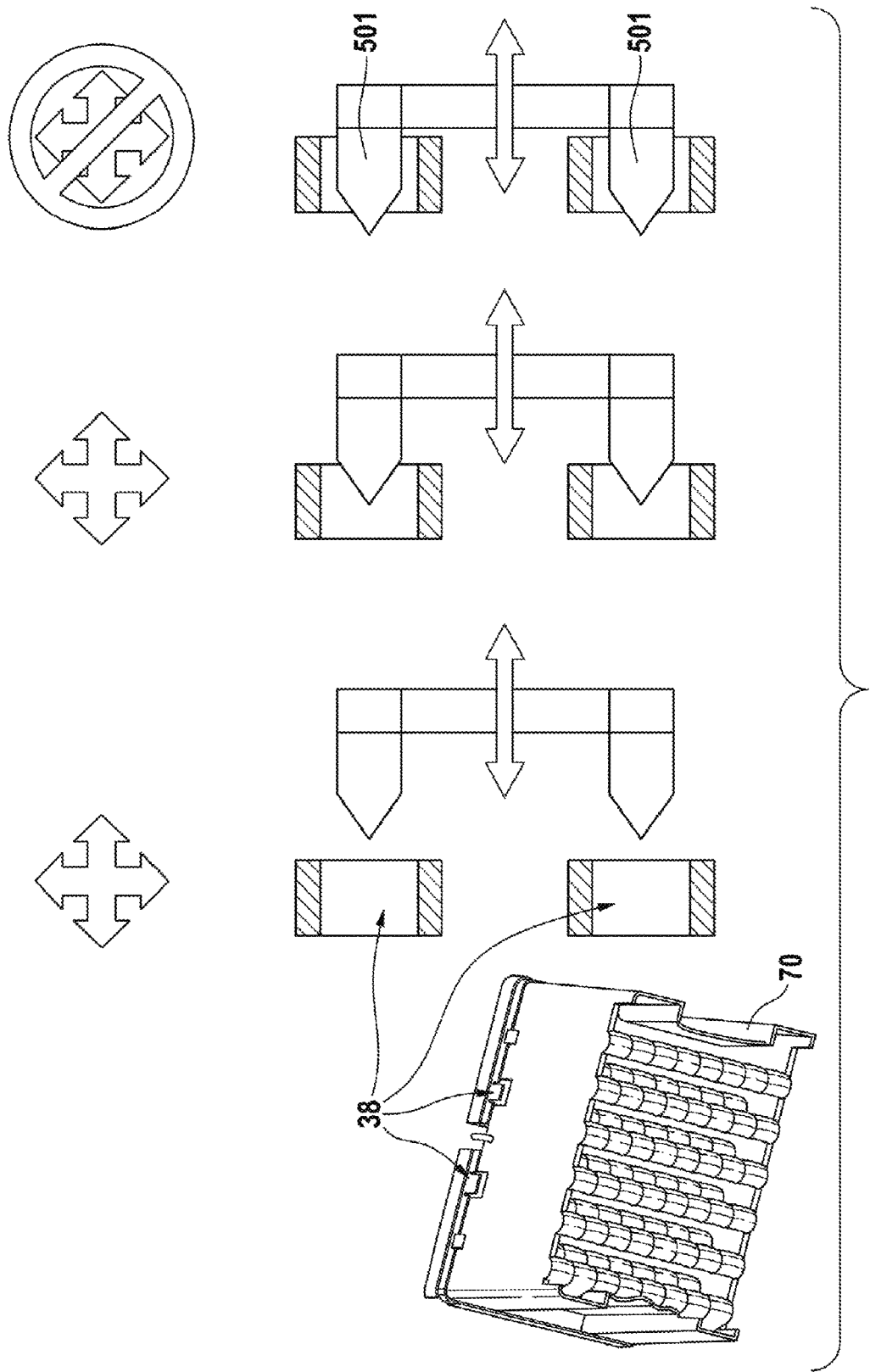
FIG. 48 shows the interaction of a tip rack with the gripper fingers. The form-lock of the gripping prevents movement in X and Y direction (see right hand panel).
Figure 49:
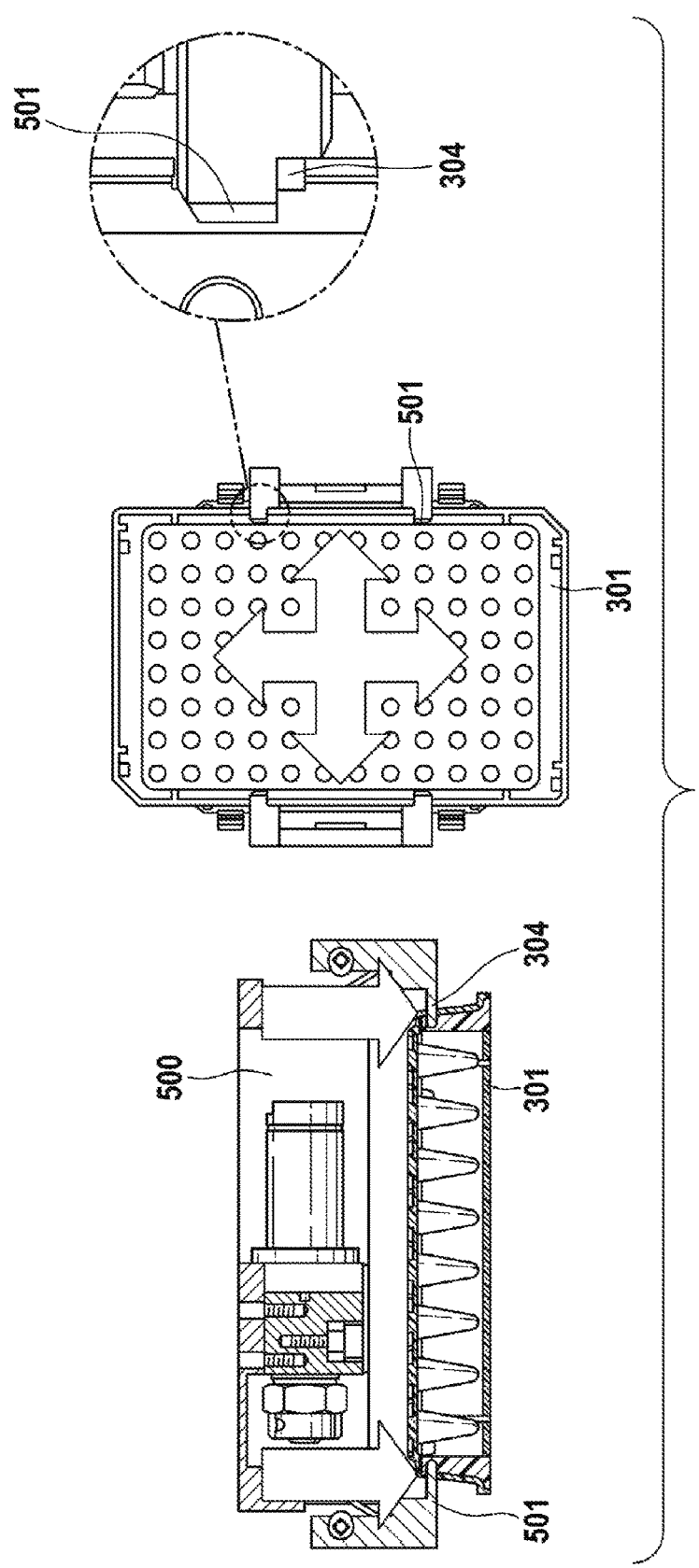
FIG. 49 shows the interaction between the handler and a multiwell plate. The gripper fingers interlock with openings on the multiwell plate, resulting in a form-lock gripping.

In a preferred embodiment, said handler comprises gripper fingers, wherein said gripper fingers fit with a recess of the multiwell plate, wherein said fit is form-locking. (FIG. 48, 49).

A system for purifying and analyzing an analyte is, furthermore, disclosed, comprising a processing cell comprising a separation station for separating an analyte comprised in a vessel of a multiwell plate from a solid support material. Preferably, said separation station is constructed and arranged to separate an analyte comprised in a vessel of a multiwell plate from a solid support material. The system further comprises an analyzing cell comprising an analyzing station, wherein said station comprises an incubator to process said analyte to generate a signal indicative of the presence or absence of said analyte. Additionally, the system comprises more than one consumable comprising openings wherein at least one opening is located on one side wall of the consumable and at least one opening is located on the opposing side wall of the consumable. A gripper system comprising at least one handler is also comprised in the system, wherein said at least one handler comprises at least one gripper finger on one side of the handler, and at least one gripper finger on the opposing side of the handler. Said gripper fingers interact with said openings on the consumables and wherein said interaction is a form-locking interaction. Preferably, the system hereinbefore described additionally comprises a sample cell constructed and arranged to transfer a liquid sample from a sample vessel to a multiwell vessel. In a preferred embodiment, the multiwell vessel is transported between cells with said gripper system. In a further preferred embodiment, the multiwell vessel is transported from said sample cell to said analyzing cell. Preferred consumables are described herein. Preferably, said more than one consumables comprise a multiwell plate and a tip rack.

Figure 50A:
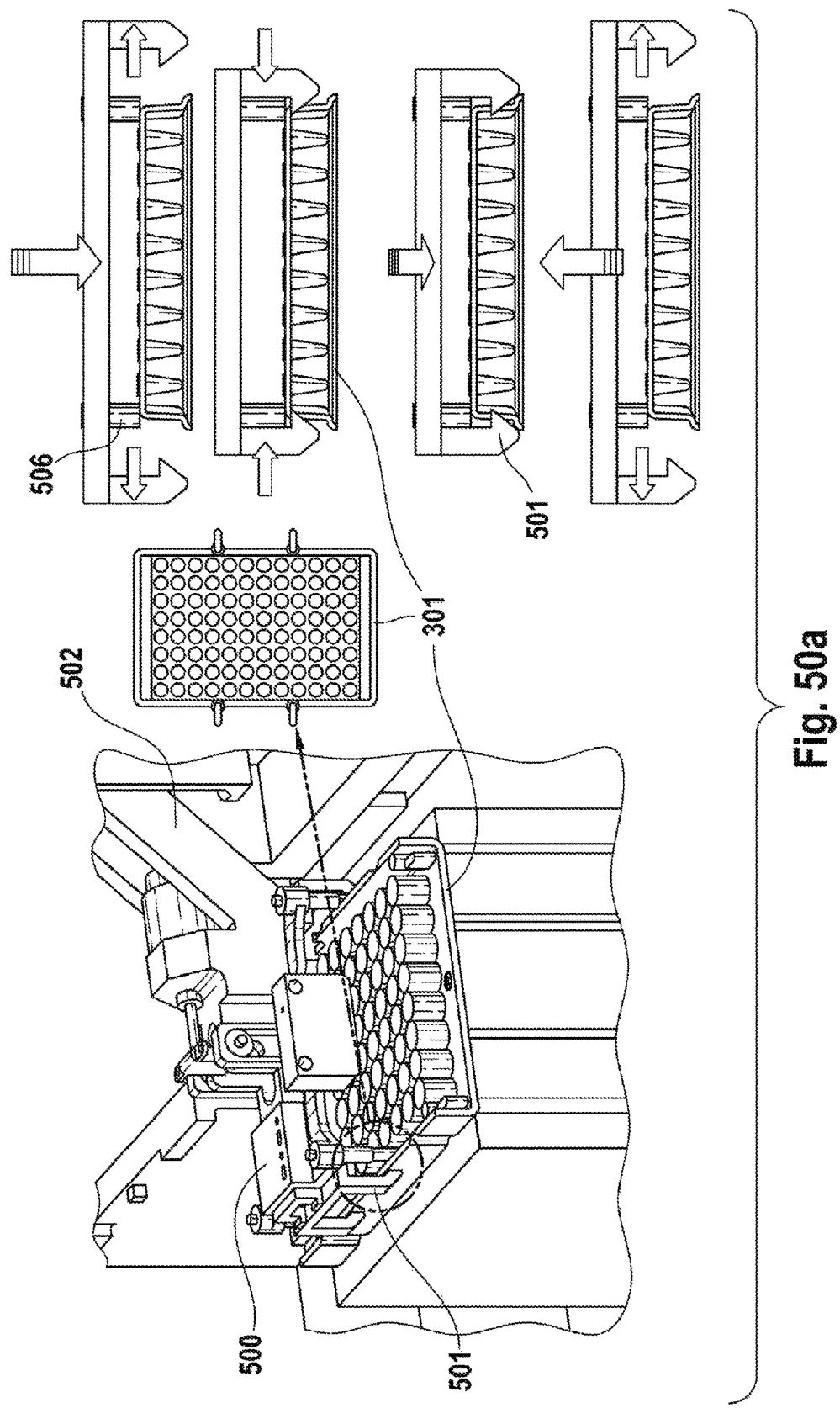
FIGS. 50 (a) and (b) show the handler connected to a robotic arm, and the attachment (FIG. 50a) and release (FIG. 50b) of the consumable by the gripper fingers.
Figure 50B:
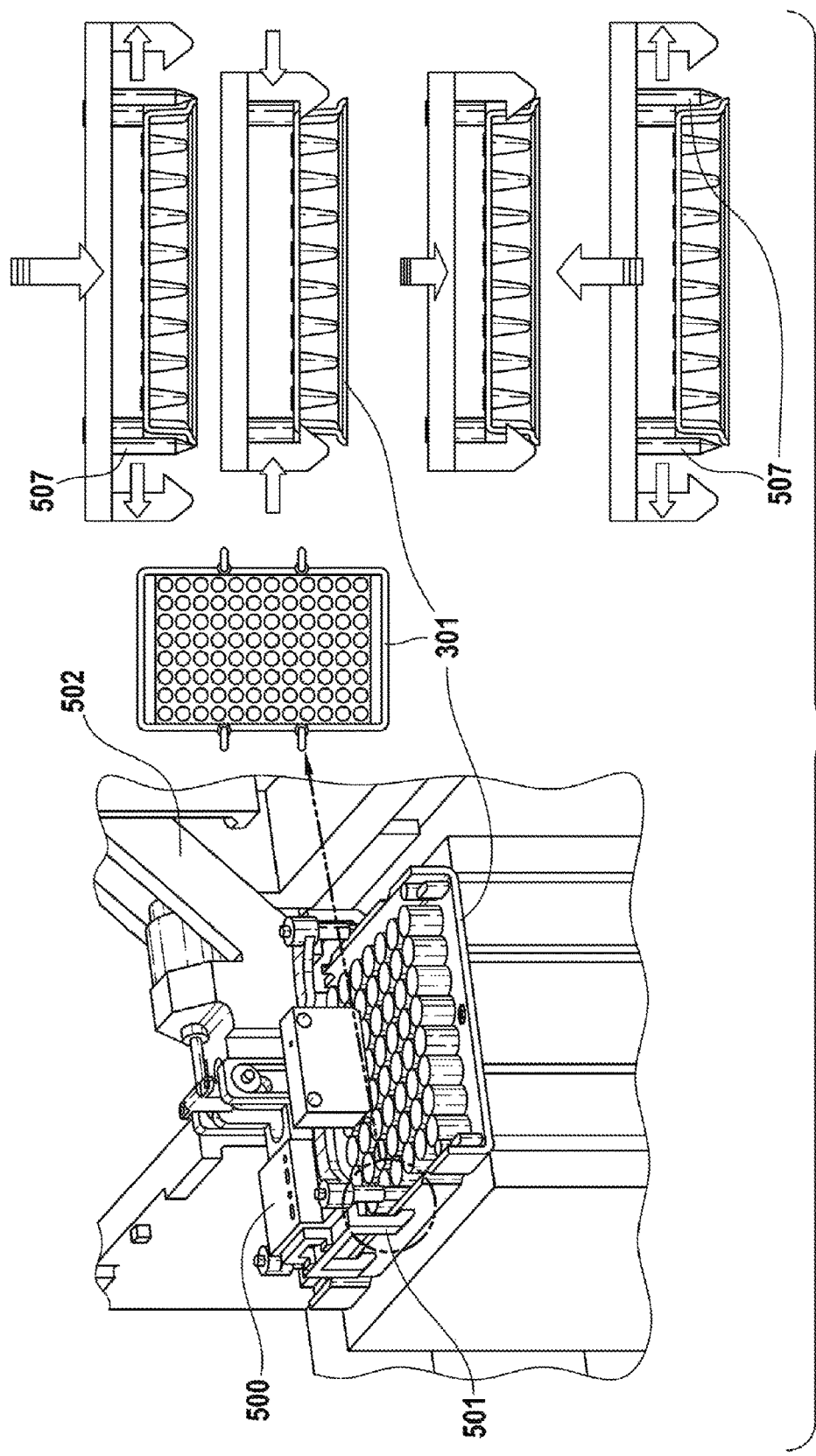
Figure 50C:
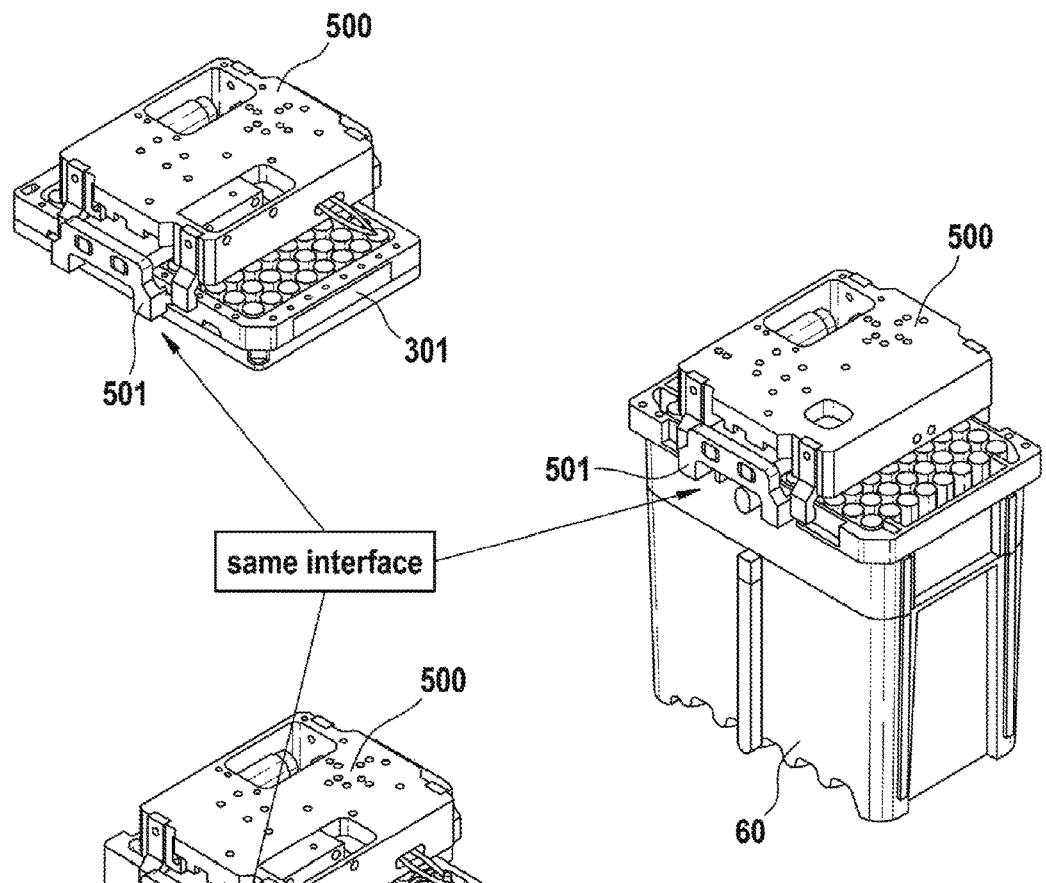

A preferred handler (500) comprises a central part (500a) which is connected to a robotic arm (502). The central part (500a) comprises, on two opposite sides, gripper fingers (501). The gripper fingers (501) are movable. When engaging with a consumable (60, 70, 101, 301, 302) comprising form-locking elements (38, 106, 507, 309), as hereinbefore described, the gripper fingers (501) connect with the consumable (60, 70, 101, 301, 302). The gripper fingers (501) are moved towards the consumable (60, 70, 101, 301, 302), in X-direction, interlock with the form locking elements (38, 106, 507, 309), until the gripper fingers (501) reach a stop. In this position, a form-locked position between handler (500) and consumable (60, 70, 101, 301, 302) exists. The handler (500) connected to the robotic arm (502) can move the consumable (60, 70, 101, 301, 302) from one position to a second position. To release the consumable (60, 70, 101, 301, 302), the gripper fingers (501) move away from the consumable (60, 70, 101, 301, 302). Preferably, the handler comprises spring-mounted pins (506). Said pins (506) are forced away from the consumable (60, 70, 101, 301, 302) when the handler (500) is pushed on the consumable (60, 70, 101, 301, 302). In this position, the gripper fingers (501) can interact with the form locking elements (38, 106, 507, 309) of the consumable (60, 70, 101, 301, 302). When pressing the handler (500) down on the consumable (60, 70, 101, 301, 302), the gripper fingers (501) can move away from the form locking elements (38, 106, 507, 309) of the consumable (60, 70, 101, 301, 302) (FIG. 50 (a)).

The handler (500) also comprises pins (507) which are located sideways of the multiwell plate when the handler (500) is moved downwards on the consumable (60, 70, 101, 301, 302) prior to gripping. These pins (507) guide the consumable (60, 70, 101, 301, 302) into the correct position for gripping. Furthermore, said pins (507) prevent the consumable (60, 70, 101, 301, 302) from getting stuck to the handler (500) when the gripper fingers (501) move away from the consumable (60, 70, 101, 301, 302) (FIG. 50 (b)).

Preferably said form-locking elements (38, 106, 507, 309) are openings (38, 106, 507, 309) in the side walls of the consumable, more preferably the long side of the consumable (60, 70, 101, 301, 302). Preferably, two openings (38, 106, 507, 309) are located on one side wall, and two openings (38, 106, 507, 309) are located on the opposite side wall.

Multiwell Plate/Processing Plate

A multiwell plate for incubating or separating an analyte is disclosed. Multiwell plates are preferably used in analytical systems. They allow parallel separation and analyzing or storage of multiple samples. Multiwell plates may be optimized for maximal liquid uptake, or for maximal heat transfer.

An improved multiwell plate for optimal use in an automated analytical system is provided.

The multiwell plate is optimized for incubating or separating an analyte in an automated analyzer. Preferably, the multiwell plate is constructed and arranged to contact a magnetic device and/or a heating device.

Said multiwell plate comprises:

a top surface comprising multiple vessels with openings at the top arranged in rows. The vessels comprise an upper part, a center part and a bottom part. The upper part is joined to the top surface of the multiwell plate and comprises two longer and two shorter sides. The center part has a substantially rectangular cross-section with two longer sides and two shorter sides;

two opposing shorter and two opposing longer side walls; and a base, wherein said base comprises an opening constructed and arranged to place the multiwell plate in contact with said magnetic device and/or a heating device.

In a preferred embodiment of the multiwell plate, adjacent vessels within one row are joined on the longer side of said almost rectangular shape.

Preferably, the multiwell plate comprises a continuous space which is located between adjacent rows of vessels. Said continuous space is constructed and arranged to accommodate a plate-shaped magnetic device. In a preferred embodiment, the bottom part of the vessels comprises a spherical bottom. In a more preferred embodiment, the bottom part of said vessels comprises a conical part located between said central part and said spherical bottom.

In a preferred embodiment, the top surface comprises ribs, wherein said ribs surround the openings of the vessels.

Preferably, one shorter side of said upper part of the vessels comprises a recess, said recess comprising a bent surface extending from the rib to the inside of the vessel.

Furthermore, in a preferred embodiment, the vessels comprise a rounded inside shape.

For fixation to the processing or incubation stations, the base preferably comprises a rim comprising recesses. Latch clips on a station of an analyzer can engage with said recesses to fix the plate on a station.

In a preferred embodiment, the vessels comprise an essentially constant wall thickness.

The processing plate (101) is preferably a 1-component plate. Its top surface (110) comprises multiple vessels (103) (FIG. 28, FIG. 29). Each vessel has an opening (108) at the top and is closed at the bottom end (112). The top surface (110) comprises ribs (104) which are preferably elevated relative to the top surface (110) and surround the openings (108) of the vessels (103). This prevents contamination of the contents of the vessels (103) with droplets of liquid that may fall onto the top surface (110) of the plate (101). Views of a preferred process plate are shown in FIGS. 26 to 37.

The footprint of the processing plate (101) preferably comprises a length and width of the base corresponding to ANSI SBS footprint format. More preferably, the length is 127.76 mm+/−0.25 mm, and the width is 85.48 mm+/−0.25 mm. Thus, the plate (101) has two opposing shorter side walls (109) and two opposing longer side walls (118). The processing plate (101) comprises form locking elements (106) for interacting with a handler (500). The processing plate (101) can be gripped, transported and positioned quickly and safely at high speed while maintaining the correct orientation and position. Preferably, the form locking elements (106) for gripping are located within the upper central part, preferably the upper central third of the processing plate (101). This has the advantage that a potential distortion of the processing plate (101) has only a minor effect on the form locking elements (106) and that the handling of the plate (101) is more robust.

The processing plate (101) preferably comprises hardware-identifiers (102) and (115). The hardware identifiers (102) and (115) are unique for the processing plate (101) and different from hardware identifiers of other consumables used in the same system. The hardware identifiers (102, 115) preferably comprise ridges (119) and/or recesses (125) on the side walls of the consumables, wherein said pattern of ridges (119) and/or recesses (125) is unique for a specific type of consumable, preferably the processing plate (101). This unique pattern is also referred to herein as a unique "surface geometry". The hardware-identifiers (102, 115) ensure that the user can only load the processing plate (101) into the appropriate stacker position of an analytical instrument (126) in the proper orientation. On the sides of processing plate (101), guiding elements (116) and (117) are comprised (FIG. 33). They prevent canting of the processing plate (101). The guiding elements (116, 117) allow the user to load the processing plates (101) with guiding elements (116, 117) as a stack into an analytical instrument which is then transferred vertically within the instrument in a stacker without canting of the plates.

Figure 37:
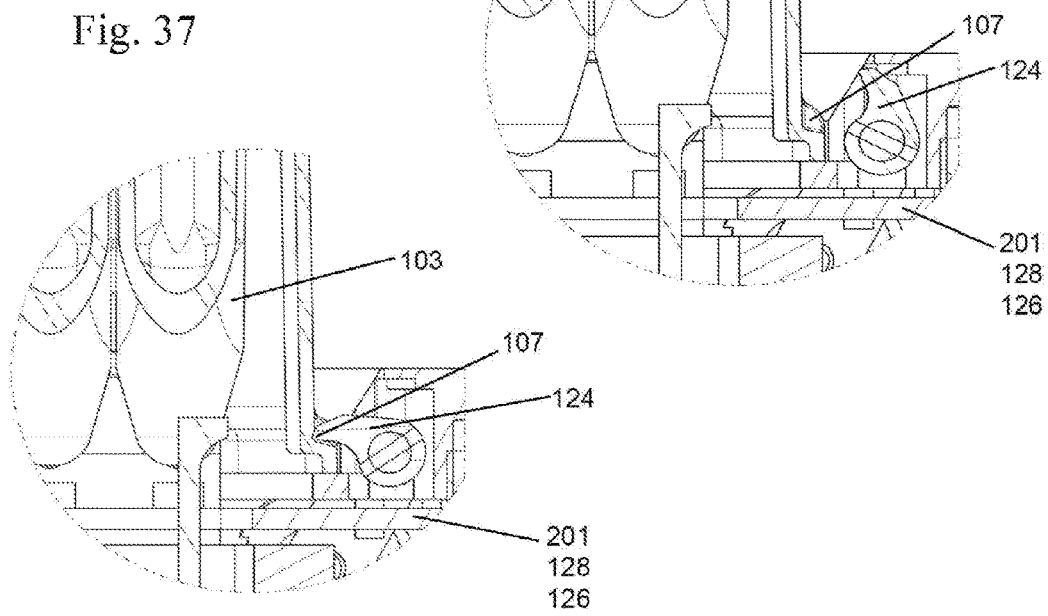
FIG. 37 shows the fitting of the Processing plate in a station for receiving the Processing plate (e.g. the magnetic separation station), with the locking mechanism engaged.

The center part (120) of the vessels (103) has an almost rectangular cross section (FIG. 30, FIG. 31). They are separated along the longer side (118) of the almost rectangular shape by a common wall (113) (FIG. 37). The row of vessels (103) formed thereby has the advantage that despite the limited space available, they have a large volume, preferably of 4 ml. Another advantage is that because of the essentially constant wall thickness, the production is very economical. A further advantage is that the vessels (103) strengthen each other and, thus, a high stability of the shape can be obtained.

Figure 35:
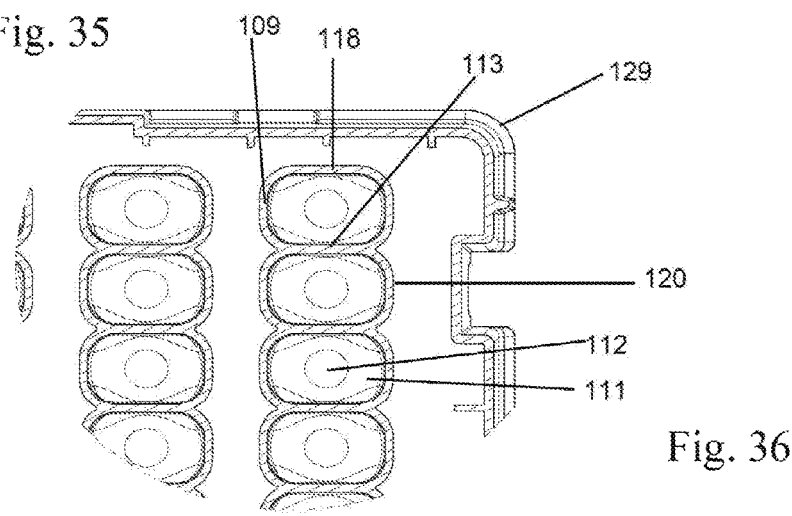
FIG. 35 shows a horizontal cross sectional view of the central region of the Processing plate and vessels.
Figure 36:
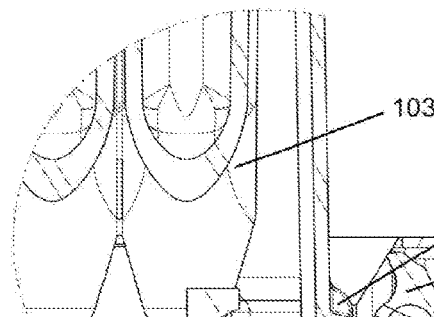
FIG. 36 shows the fitting of the Processing plate in a station for receiving the Processing plate (e.g. the magnetic separation station), with the locking mechanism disengaged.

Between the rows (123) of vessels (103), a continuous space (121) is located (FIG. 31, FIG. 35). The space (121) can accommodate magnets (122) or heating devices (128) (FIG. 36, FIG. 38). These magnets (122, 127) and heating devices (128) are preferably solid devices. Thus, magnetic particles (216) comprised in liquids (215) which can be held in the vessels (103) can be separated from the liquid (215) by exerting a magnetic field on the vessels (103) when the magnets (122, 127) are brought into proximity of the vessels (103). Or the contents of the vessels (103) can be incubated at an elevated, controlled temperature when the processing plate (101) is placed on the heating device (128). Since the magnets (122, 127) or heating devices (128) can be solid, a high energy density can be achieved. The almost rectangular shape of the central part (120) of the vessels (103) (FIG. 36, FIG. 37) also optimizes the contact between the vessel wall (109) and a flat shaped magnet (122) or heating device (128) by optimizing the contact surface between vessel (103) and magnet (122) or heating device (128) and thus enhancing energy transfer into the vessel (103).

In the area of the conical bottom (111) of the vessels, the space (121) is even more pronounced and can accommodate further magnets (127). The combination of the large magnets (122) in the upper area and the smaller magnets (127) in the conical area of the vessels (3) allows separation of magnetic particles (216) in larger or small volumes of liquid (215). The small magnets (127), thus, make it easier to sequester the magnetic particles (216) during eluate pipetting. This makes it possible to pipette the eluate with minimal loss by reducing the dead volume of the magnetic particle (216) pellet. Furthermore, the presence of magnetic particles (216) in the transferred eluate is minimized.

At the upper end of the vessels (103), one of the shorter side walls (109) of the vessel (103) comprises an reagent inlet channel (105) which extends to the circumferential rib (104) (FIG. 32, FIG. 30). The reagents are pipetted onto the reagent inlet channel (105) and drain off the channel (105) into the vessel (103). Thus, contact between the pipette needle (80) or tip (3, 4) and liquid contained in the vessel is prevented. Furthermore, splashes resulting from liquid being directly dispensed into another liquid (215) contained in the vessels (103), which may cause contamination of the pipette needle (80) or tip (3, 4) or neighboring vessels (103) is prevented. Sequential pipetting onto the reagent inlet channel (105) of small volumes of reagents followed by the largest volume of another reagent ensures that the reagents which are only added in small amounts are drained completely into the vessel (103). Thus, pipetting of small volumes of reagents is possible without loss of accuracy of the test to be performed.

On the inside, on the bottom of the vessels (111, 112), the shape becomes conical (111) and ends with a spherical bottom (112) (FIG. 34). The inside shape of the vessel (114), including the rectangular center part (120), is rounded. The combination of spherical bottom (112), rounded inside shape (114), conical part (111) and refined surface of the vessels (103) leads to favorable fluidics which facilitate an effective separation and purification of analytes in the processing plate (101). The spherical bottom (112) allows an essentially complete use of the separated eluate and a reduction of dead-volume which reduces the carryover of reagents or sample cross-contamination.

The rim on the base (129) of the processing plate (101) comprises recesses (107) for engagement with latch clips (124) on the processing station (201) or heating device (128) or analytical instrument (126) (FIG. 28, FIG. 38, FIG. 39). The engagement of the latch clips (124) with the recesses (107) allows positioning and fixation of the processing plate (101) on the processing station (201). The presence of the recesses (107) allows the latch force to act on the processing plate (101) almost vertically to the base (129). Thus, only small forces acting sideways can occur. This reduces the occurrence of strain, and, thus, the deformation of the processing plate (101). The vertical latch forces can also neutralize any deformations of the processing plate (101) leading to a more precise positioning of the spherical bottoms (111) within the processing station (201). In general, the precise interface between the processing plate (101) and the processing station (201) or heating device (128) within an analyzer (126) reduces dead-volumes and also reduces the risk of sample cross-contamination.

Separation Station

A device for separating an analyte bound to magnetic particles in a liquid contained in a vessel is disclosed. The device comprises a multiwell plate comprising vessels with an opening at the top surface of the multiwell plate and a closed bottom. The vessels comprise an upper part, a center part and a bottom part, wherein the upper part is joined to the top surface of the multiwell plate and preferably comprises two longer and two shorter sides. The center part has a substantially rectangular cross-section with two longer sides, wherein said vessels are aligned in rows. A continuous space is located between two adjacent rows for selectively contacting at least one magnet mounted on a fixture with the side walls in at least two Z-positions. The device further comprises a magnetic separation station comprising at least one fixture. The fixture comprises at least one magnet generating a magnetic field. A moving mechanism is present which vertically moves said at least one fixture comprising at least one magnet at least between first and second positions with respect to the vessels of the multiwell plate. Preferably, said at least two Z-positions of the vessels comprise the side walls and the bottom part of said vessels. The magnetic field of said at least one magnet preferably draws the magnetic particles to an inner surface of the vessel adjacent to said at least one magnet when said at least one magnet is in said first position. The effect of said magnetic field is less when said at least one magnet is in said second position than when said at least one magnet is in said first position. Preferably, the fixture comprising said at least one magnet comprises a frame. The vessels have preferred features as described under Multiwell plate/Processing plate. One such preferred feature is that at least a part of said vessels has a substantially rectangular cross-section orthogonal to the axis of said vessels.

In said first position, said at least one magnet is adjacent to said part of said vessels. Adjacent is understood to mean either in close proximity such as to exert a magnetic field on the contents of the vessel, or in physical contact with the vessel.

The separation station comprises a frame to receive the multiwell plate, and latch-clips to attach the multiwell plate. Preferably, the separation station comprises two types of magnets. This preferred embodiment is further described below.

A second preferred embodiment is described below, which comprises a spring which exerts a pressure on the frame comprising the magnets such that the magnets are pressed against the vessels of the multiwell plate.

The first magnets are preferably constructed and arranged to interact with vessels of a multiwell plate for exerting a magnetic field on a large volume of liquid comprising magnetic particles held in said vessels. Said second magnets preferably are constructed and arranged to interact with vessels of a multiwell plate for exerting a magnetic field on a small volume of liquid comprising magnetic particles held in said vessels. Said first and second magnets can be moved to different Z-positions.

A method of isolating and purifying an analyte, preferably a nucleic acid is disclosed. The method comprises the steps of binding an analyte to magnetic particles in a vessel of a multiwell plate. The vessel comprises an upper opening, a central part and a bottom part. The bound material is then separated from unbound material contained in a liquid when the major part of the liquid is located above the section where the conical part of the vessel is replaced by the central part with the rectangular shape, by moving a magnet from a second position to a first position and, in said first position, applying a magnetic field to the central part and, optionally, additionally applying a magnetic field to the bottom part of said vessel. The magnetic particles can optionally be washed with a washing solution. A small volume of liquid, wherein the major part of the liquid is located below the section where the conical part of the vessel is replaced by the central part with the rectangular shape is separated from said magnetic particles by selectively applying a magnetic field to the bottom part of said vessel.

The method hereinbefore described preferably additionally comprises between steps c) and d) the step of eluting said nucleic acid. Preferably, the method comprises the step of transferring said eluate from a said multiwell plate to a second multiwell plate. In a further preferred embodiment, in step b), a first type of magnet is moved from a second position to a first position to apply a magnetic field to a central part of the vessel, and, optionally, a second type of magnet is moved to the bottom part of the vessel to apply a magnetic field. More preferably, a magnet is moved to the central part of the vessel for step b), and the magnet is moved to the bottom part of said vessel into a third position for eluting said nucleic acid.

A magnetic separation station for separating an analyte bound to magnetic particles is disclosed, said separation station comprising first magnets which are constructed and arranged to interact with vessels of a multiwell plate for exerting a magnetic field on a large volume of liquid comprising magnetic particles held in said vessels, and second magnets constructed and arranged to interact with vessels of a multiwell plate for exerting a magnetic field on a small volume of liquid comprising magnetic particles held in said vessels, and wherein said first and second magnets can be moved to different Z-positions. Preferred embodiments of the magnetic separation station are described herein.

A first preferred embodiment of a separation station (201) is described below. The first preferred embodiment of said separation station (201) comprises at least two types of magnets (202, 203). The first, long type of magnet (202) is constructed and arranged to fit into the space (121) of the processing plate (101). Magnet (202), thus, exerts a magnetic field on the liquid (215) in the vessel (103) to sequester magnetic particles (216) on the inside of the vessel wall. This allows separation of the magnetic particles (216) and any material bound thereto and the liquid (215) inside the vessel (103) when a large volume of liquid (215) is present. Magnet (202) has an elongated structure and is constructed and arranged to interact with the essentially rectangular central part (120) of the vessel. Thus, magnet (202) is used when the major part of the liquid (215) is located above the section where the conical part (111) of the vessel (103) is replaced by the central part (120) with the rectangular shape. As shown in FIG. 40, the preferred construction of the magnets (202) comprises fixtures (204, 204a) comprising magnets (202) which fit into the space (121) between the rows of vessels (103) in the processing plate (101). Another preferred embodiment of magnets (202) comprises magnets (202) arranged on fixtures (204, 204a). The magnets (203) of the preferred separation station (201) are smaller, and can interact with the conical part (111) of the vessel (103). This is shown in FIG. 41 (a). Magnets (203) are preferably arranged on a base (205) which can be moved into the space (121) of the processing plate (101). Each magnet (202, 203) is preferably constructed to interact with two vessels (103) in two adjacent rows. In a preferred embodiment, the processing plate (101) has 6 rows of 8 vessels (103). A separation station (201) which can interact with the preferred processing plate (101) has three fixtures (204, 204a) comprising magnets (202) and four bases (205) comprising magnets (203). An embodiment is also included wherein the separation station has four magnetic fixtures (204, 204a) comprising magnets (202) and three magnetic bases (205) comprising magnets (203).

The magnets (202, 203) are movable. The separation station (201) comprises a mechanism to move the fixtures (204, 204a) and the bases (205). All fixtures (204, 204a) are interconnected by a base (217) and are, thus, moved coordinately. All magnets (203) are joined to one base (218) and are, thus, moved coordinately. The mechanism for moving the magnetic plates (202) and (203) is constructed and arranged to move the two types of magnetic plates (202, 203) to a total of four end positions.

In FIG. 40 a-c, the magnets (203) are located in proximity of the conical part of the vessels (103) of the processing plate (101). This is the uppermost position of magnets (203), and is the separation position. In this Figure, the magnets (202) are located in the lowermost position. They are not involved in separation when they are in this position.

In FIG. 41 a-c, the magnets (202) and (203) are in their lowermost position. None of the magnets is in a separation position. Therefore, in this position, no separation of magnetic particles from liquid can occur.

FIG. 42 a-c show a position in which the magnets (202) are located in the space (121) of the processing plate (101). This is the highest Z-position of magnets (202). In this Figure, the magnets (203) are also located in the highest Z-position. They exert a magnetic field on the liquid in the conical area of the vessels (103). Thus, both magnets are in a separation position. The highest Z-position of magnets (202) and (203) are, thus, different.

FIG. 43 a-c show a position in which the magnets (202) are located in the space (121) of the processing plate (101). This is the uppermost position of magnets (202), and is the separation position. In this Figure, the magnets (203) are located in the lowermost position. They are not involved in separation when they are in this position.

In the preferred embodiment shown in FIGS. 40 to 43, the base (217) of magnets (202) is connected to a positioning wheel (206). The base (217) comprises a bottom end (207) which is flexibly in contact with a connecting element (208) by a moving element (209). Said moving element is constructed and arranged to move the connecting element (208) along a rail (212) from one side to the other. Said moving element (209) is fixed to the connecting element (208) with a pin (220). Said connecting element (208) is fixed to the positioning wheel (206) by screw (210). Connecting element (208) is also connected to axis (211). Said connecting element (208) is preferably a rectangular plate. As the positioning wheel (206) moves eccentrically, around an axis (211), such that the screw (210) moves from a point above the eccentric axis to a point below the eccentric axis, moving element (209) and the bottom end (207) of the base (204) with the magnets (202) attached thereto are moved from the uppermost position to the lowermost position. The base (218) is mounted on a bottom part (219) and is connected, at its lower end, with pin (213) to a moving element (214), which is preferably a wheel, which interacts with the positioning wheel (206). When the positioning wheel (206) rotates around the axis (211), wheel (214) moves along positioning wheel (206). If the wheel (214) is located on a section of positioning wheel (206) where the distance from the axis (211) is short, the magnets (203) are in their lowermost position. When wheel (214) is located on a section of positioning wheel (206) where the distance from the axis (211) is at a maximum, the magnets (203) are in their uppermost position. Thus, in the preferred embodiment of the first embodiment of the separation station, the location of the magnets (203) is controlled by the shape of the positioning wheel (206). When moving element (209) moves along the central, rounded upper or lower part (212a) of rail (212), the small type of magnets (203) are moved up and down. When the moving element (209) is located on the side (212b) of bottom end (207) and moves up or down, the magnets (202) are moved up- or downwards. The positioning wheel can be rotated by any motor (224).

In a preferred embodiment, a spring (225) is attached to the base (222) of the separation station and the base (218) of magnets (203) to ensure that magnets (203) are moved into the lowermost position when they are moved downwards.

The term "pin" as used herein relates to any fixation element, including screws or pins.

In a second preferred embodiment, the separation station (230) comprises at least one fixture (231) comprising at least one magnet (232), preferably a number of magnets equal to a number of vessels (103) in a row (123). Preferably, the separation station (230) comprises a number of fixtures (231) equal to the number of rows (123) of the multiwell plate (101) hereinbefore described. More preferably, six fixtures (231) are mounted on the separation station (230). At least one magnet (232) is mounted on one fixture (231). Preferably, the number of magnets (232) equals the number of vessels (103) in one row (123). Most preferably, eight magnets (232) are mounted on one fixture (231). Preferably, one type of magnet (232) is comprised on said fixture (231). More preferably, the magnet (232) is mounted on one side of the which is oriented towards the vessels with which the magnet interacts.

The fixture (231) is mounted on a base (233). Preferably, said mount is flexible. The base (233) comprises springs (234) mounted thereon. The number of springs (234) is at least one spring per fixture (231) mounted on said base (233). The base further comprises a chamfer (236) which limits the movement of the spring and, consequently, the fixture (231) comprising the magnets (232). Preferably, any one of said springs (234) is constructed and arranged to interact with a fixture (231). More preferably, said spring (234) is a yoke spring. Said interaction controls the horizontal movement of the fixtures (231). Furthermore, the separation station (230) comprises a frame (235). The base (233) with fixtures (231) is connected to the frame (235) by a moving mechanism as described hereinbefore for the magnets (232) of the first embodiment.

Preferably, said base (233) and fixture (231) is constructed and arranged to move vertically (in Z-direction).

The multiwell plate (101) hereinbefore described is inserted into the separation station (230). The fixture (231) comprising the magnets (232) is moved vertically. Any one fixture (232) is, thus, moved into a space (121) between two rows (123) of vessels (103). The vertical movement brings the magnets (232) mounted on a fixture (231) into contact with the vessels (103). The Z-position is chosen depending on the volume of liquid (215) inside the vessels (103). For large volumes, the magnets (232) contact the vessels (103) in a center position (120) where the vessels (103) are of an almost rectangular shape. For small volumes of liquid (215) where the major part of the liquid (215) is located below the center part (120) of the vessels (103), the magnets (232) preferably contact the conical part (111) of the vessels (103).

A spring is attached to the base (233) of any one frame (231) (FIG. 39 (a), (b)). The spring presses the magnets (232) against the vessels (103). This ensures a contact between magnets (232) and vessels (103) during magnetic separation. Preferably, the magnet (232) contacts the vessel (103) on the side wall (109) located underneath the inlet (105). This has the advantage that liquid which is added by pipetting flows over the sequestered magnetic particles and ensures that particles are resuspended and that all samples in all vessels are treated identically.

This embodiment is particularly suited to separate a liquid (215) comprised in a multiwell plate (101) as hereinbefore described, from magnetic particles (216) when different levels of liquid (215) are contained in the vessels (103) of said multiwell plate (101).

AD Plate and Frame

For amplification and detection, multiwell plates are commonly used. Such plates are particularly useful in automated analytical systems which comprise an amplification station for amplifying nucleic acid analytes.

In order to prevent contamination between wells prior to, during and after the amplification reaction, reaction vessels in which amplification takes place are sealed. A common way of sealing for amplification multiwell plates comprises placing a sealing foil on the plate and connecting it to the plate, either by gluing or by heat sealing.

An improved automated method for isolating and amplifying a nucleic acid, improved multiwell plate with a sealing foil and improved automated analytical system are disclosed herein.

A method for isolating and amplifying a nucleic acid analyte that may be present in a fluid sample is disclosed. The method comprises separating said nucleic acid analyte from other material present in said fluid sample in a first vessel. Preferably, said first vessel is comprised in a first multiwell plate. A second multiwell plate is provided. This second multiwell plate comprises a lid which comprises a frame and a sealing foil. The lid is lifted and then the separated analyte in the first vessel is transferred to a well of the second multiwell plate. The lid comprising said sealing foil is placed on the second multiwell plate. Then the second multiwell plate is sealed with the sealing foil. Once the second multiwell plate is sealed, the analyte in amplified in the presence of amplification reagents which were added prior to sealing, in said second multiwell plate.

In a preferred embodiment, in step b), the lid is present on the second multiwell plate in a first position, said first position preventing contact between the sealing foil and the multiwell plate; and in step e), the lid is placed on said second multiwell plate in a second position, wherein said second position promotes contact between said sealing foil and said multiwell plate.

In a preferred embodiment of the method hereinbefore described, the lid is rotated by 180°.

Preferably, the frame comprises supporting ribs, more preferably four supporting ribs, and the multiwell plate comprises corresponding recesses, more preferably four corresponding recesses, wherein said recesses are positioned such that the supporting ribs of the frame do not align with the recesses in the first position of the lid on the multiwell plate, and that the supporting ribs do align with the recesses in the second position of the lid on the multiwell plate.

In said second position, the supporting ribs of the frame are preferably placed within the recesses of the multiwell plate.

In one preferred embodiment of the method described herein, the sealing in step f) is heat sealing. Further preferred embodiments of the method are described hereinbefore or hereinafter.

A multiwell plate set comprising a multiwell plate and a lid is disclosed, wherein said lid comprises a frame and a sealing foil affixed to said frame, wherein in a first position of said lid on said multiwell plate, a separation distance is located between said sealing foil and the top surface of said multiwell plate, and in a second position, the sealing foil is in contact with said top surface of the multiwell plate. Preferably, the frame comprises supporting ribs and the multiwell plate comprises openings, wherein, in said first position, the supporting ribs are in a different location than the openings, and in said second position, said supporting ribs and said openings align. In a preferred embodiment of the multiwell plate set herein described, the top surface of said multiwell plate comprises heat rims, and in said second position, the sealing foil contacts the heat rims. Preferably, the sealing foil is affixed to the frame by a heat sealing method. More preferably, the sealing foil is affixed to the top surface of the frame. In a preferred embodiment, the sealing foil comprises a polymer. Preferably, the sealing foil comprises at least two layers with different melting points. More preferably, the sealing foil comprises two layers with different melting points, wherein the layer with the lower melting point is oriented towards the multiwell plate. Further preferred embodiments of the method are described hereinbefore or hereinafter.

An analytical system comprising a holding station and a multiwell plate as described herein is also disclosed, wherein said multiwell plate is fixed in said holding station.

Preferably, the analytical system additionally comprises a sealing station for heat-sealing of the sealing foil comprised in the frame to the multiwell plate.

Preferably, the multiwell plate comprises a base with a rim which comprises recesses, wherein a positioning and fixing element on said holding station contacts said recesses, wherein said contact exerts a downwards pressure on the base of the multiwell plate, thereby fixing the multiwell plate in the holding station.

The exemplary multiwell plate with a frame comprises a multiwell plate (300) which comprises a multitude of vessels (312). Said vessels (312) are integrally formed on the upper surface (326) of the multiwell plate (301). On the upper surface (326) each vessel (312) is surrounded by an elevated heat rim (311). The lid (302) comprises a frame (302b) comprising a polymer (314) and a foil (303) comprising a polymer. The foil (303) is affixed to the frame (302b) by a heat sealing method. Preferably, the foil (303) is sealed onto the top surface (302a), more preferably by heat sealing.

The multiwell plate (300) comprises two long side walls (323, 324) which are opposite each other, and two short side walls (319, 320) which are opposite each other. The frame (302b) comprises two long side walls (328, 327) which are located opposite each other and two short side walls (321, 322) which are located opposite each other.

Figure 45A:
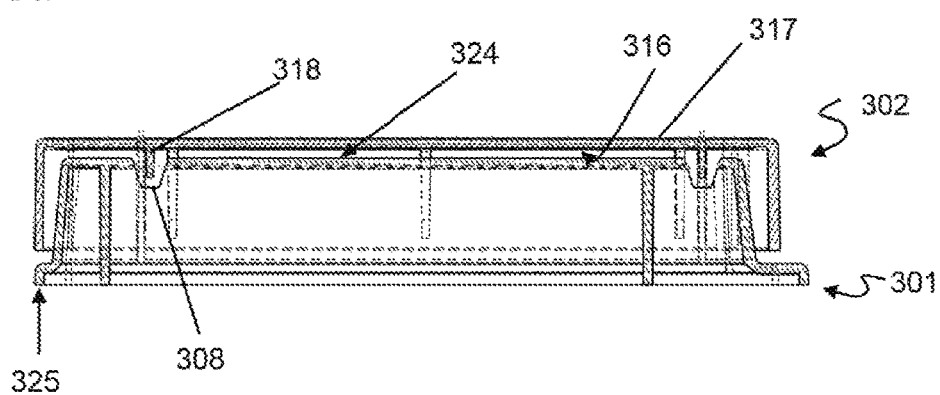
FIG. 45 (a) shows a sectional side view of the AD plate and frame in sealing position.
Figure 45B:
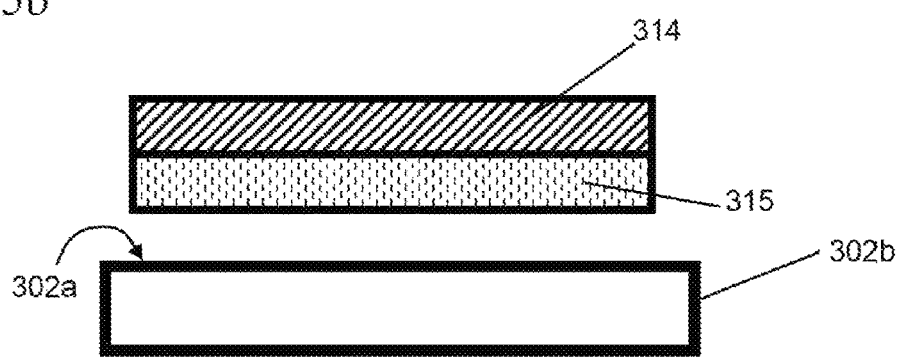
Figure 46A:
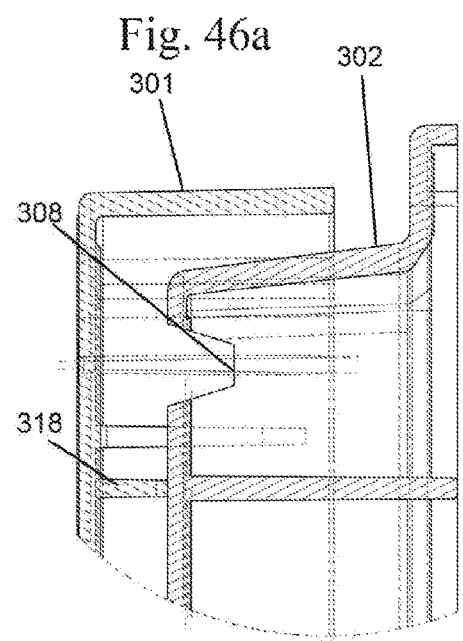
FIGS. 46 (a) and (b) show side (FIG. 46a) and top (FIG. 46b) sectional views of one corner of the AD plate and frame in storage position.
Figure 46B:
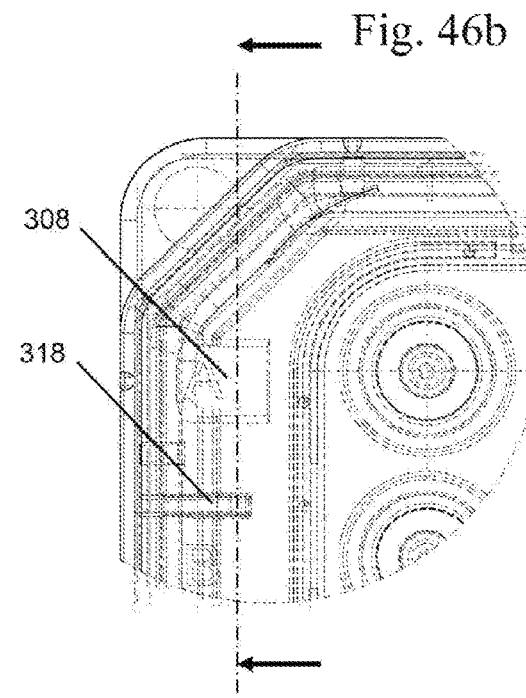
Figure 46C:
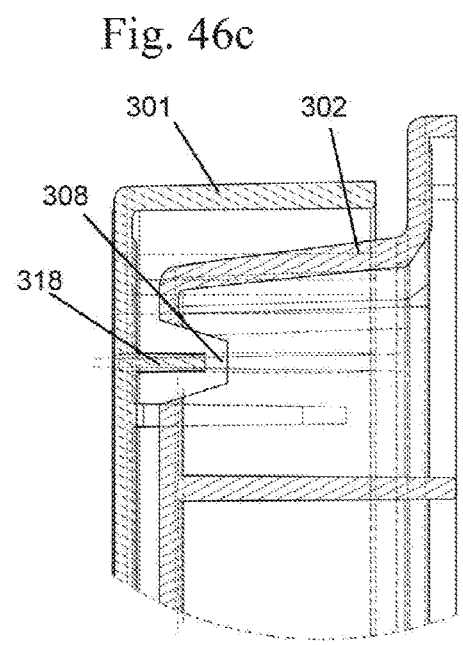
Figure 46D:
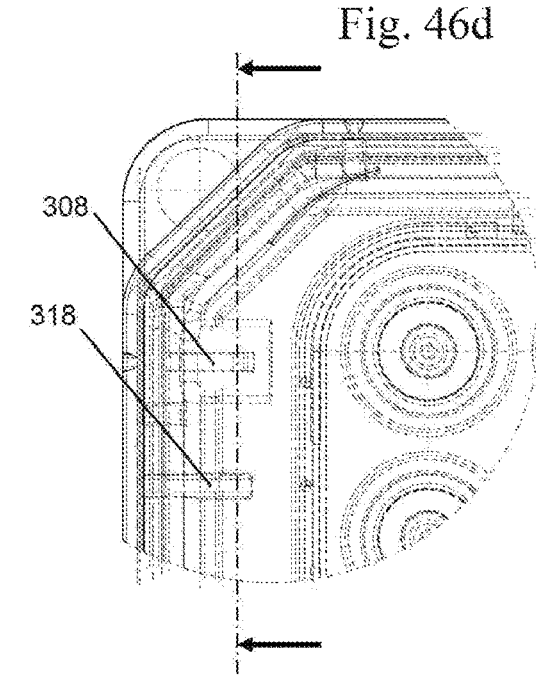

The preferred foil (303) comprises two layers (314, 315) with different melting points. One layer (311) has a lower melting point. This layer (311) is oriented towards the multiwell plate (301) with the heat rims (310, 311) and the surface (302a) of the frame (302b). During heat sealing, heat is transferred through the more stable layer (310) with the higher melting point to layer (311) with the lower melting point. Layer (311) is, thus, heated and melted. The upper layer (310) is not melted during heat sealing. This minimizes the risk of a leaking foil (303) (FIG. 45 (b)).

The multiwell plate (301) and lid (302) are assembled pairwise (300) for supply. On the inside (316) of the top surface (317), the frame (302b) comprises supporting ribs (318). Two supporting ribs (318) are located along a first side wall (321) of the frame (302b), and two supporting ribs (318) are located along a second side wall (322) opposite of the first side wall (319). Preferably, said side walls are the short side walls of the frame (302b). The edge of the top surface (313) of the multiwell plate (301) comprises openings (308). Said openings (308) are located along side walls (319, 320) corresponding to the side walls of the frame (321, 322) where the supporting ribs (318) are located. In the assembly/supply position of the lid (302) relative to the multiwell plate (301) (FIG. 44 (a)), the openings (308) are placed such that they do not align with the supporting ribs (318). Thus, when the lid (302) is placed on the multiwell plate (301), the supporting ribs (318) sit on the top surface (313) of the multiwell plate (301) (FIG. 46 (a)). This prevents the foil (303) from contacting the heat rims (310, 311), and, thus, prevents scratches on the foil (303) that may otherwise be caused by slipping of one multiwell plate (300) over the surface of the foil of a second multiwell plate (300) and which may impair the optical and mechanical properties of the foil (303) during transport, storage and loading.

When the microwell plate (301) with lid (302) is used in an analytical instrument (126), the lid (302) is lifted for addition of purified analyte and reagents. When all reagents are added to the vessels (312), the lid (302) is rotated by 180° and placed on the multiwell plate (301) (FIGS. 44 (b) and (c)). The openings (308) on the top of the multiwell plate (301) and the supporting ribs (318) on the frame (302b) are brought into alignment by the 180° rotation. Thus, when placed on the multiwell plate (301), the foil (303) is brought into contact with the heat rims (311) surrounding the vessels (312) of the multiwell plate (301), and heat can be applied to seal the vessels (312) with the foil (303) (FIG. 44 d), FIG. 45 (a)).

Both microwell plate (301) and lid (302) comprise a length and width of the base corresponding to ANSI SBS footprint format. More preferably, the length is 127.76 mm+/−0.25 mm, and the width is 85.48 mm+/−0.25 mm. They comprise openings (304) on plate (301) and (309) on lid (302) which are constructed and arranged to be gripped by a handler (500), either in pairwise arrangement or individually. Thus, it is possible to grip and transport the assembled plate and frame (300), or only the lid (302) or only the plate (301).

The multiwell plate (301) comprises a base (325) surrounding the bottom of the sidewalls (319 to 322) of the plate (301). Said base (325) comprises recesses (306). These recesses (306) can interact with a positioning and fixing element (124a) on a holding station (330) of the analyzer (126), as described hereinbefore for the Processing Plate. The interaction between the positioning and fixing element (124a) and the recess (306) positions and fixes plate (301). This allows to keep the plate (301) fixed on the holding station (330) when handling the lid (302) independently of the plate (301). It also removes potential torsion or other types of unevenness of the plate (301). The fixing of the plate (301) also leads to a maximal contact surface between plate (301) and holding station (330). This equalizes potential differences in static charge between holding station (330) and plate (301). Finally, the fixing also ensures that the vessels (312) all are located at the same height, allowing for more precise pipetting.

The frame (302b) comprises a recess (307). This recess is located at the lower end of the side of the frame (302b). The recess is preferably located in a different position than openings (304). Preferably, two recesses (307) are located on one side of the frame (302), and two recesses (307) are located on the opposite side of the frame (302b). Most preferably, said recesses (307) are located in the same position as recesses (306) on the multiwell plate (301). The recesses (307) ensure that when the plate (301) is fixed by engagement of fixing elements (124a) and recesses (306) only the multiwell plate (301) is fixed, not the lid (302).

Analytical System with Hardware Coding of Consumables

An analytical system (440) comprising an automated analytical apparatus (400) for isolating and/or analyzing an analyte is disclosed. An "analyte" as used herein relates to any type of analyte of interest. Preferred analytes are polypeptides or nucleic acids. More preferably, the analyte is a nucleic acid. The analytical system (440) further comprises more than one type of consumables (60, 70, 101, 301, 302), wherein said consumables (60, 70, 101, 301, 302) have essentially a same footprint, and wherein any type of consumables (60, 70, 101, 301, 302) comprises a unique surface geometry (601). Furthermore, the system also comprises a system comprising specific recognition elements for distinguishing said different consumables wherein any one of said recognition elements comprises a unique surface geometry complementary to a unique surface geometry of a specific type of consumable. Preferably, said system for distinguishing said different consumables (60, 70, 101, 301, 302) constructed and arranged to recognize specifically said unique surface geometry (601).

The analytical system (440) disclosed herein is preferably a system (440) comprising a module (401) for isolating and/or purifying an analyte. More preferably, the system (440) additionally comprises a module (403) for analyzing said analyte to obtain a detectable signal. The detectable signal can be detected in the same module (401, 402, 403), or, alternatively in a separate module. The term "module" as used herein relates to any spatially defined location within the analyzer (400). Two modules (401, 403) can be separated by walls, or can be in open relationship. Any one module (401, 402, 403) can be either autonomously controlled, or control of the module (401, 402, 403) can be shared with other modules. Preferably, all modules are controlled centrally. Transfer between modules (401, 402, 403) can be manual, but is preferably automated. Thus, a number of different embodiments of automated analyzers (400) are encompassed by the present disclosure.

Consumables (60, 70) with essentially identical footprint are plastic consumables for storing other consumables, such a pipette tips or single tubes, of for holding reagents and samples, or consumables (101, 301, 302) holding reaction mixes in which the processing or analyzing of the analyte are performed. Preferred embodiments of such consumables are racks (60, 70) or multiwell plates (101, 301, 302). Different types of multiwell plates (101, 301, 302) with identical footprint can preferably be used in the system (440). Such preferred types of multiwell plates (101, 301, 302) are multiwell plates for storing samples or reagents, multiwell plates for isolating and analyzing an analyte, and/or multiwell plates for reacting an analyte to obtain a detectable signal. In a preferred embodiment, if the analyte is a nucleic acid, the reacting may be any type of amplification of nucleic acids known to the person skilled in the art. Preferably, said consumables (60, 70, 101, 301, 302) comprise at least one tip rack (60, 70) and one multiwell plate (101, 301). Preferably, said footprint comprises a length and width of the base corresponding to ANSI SBS footprint format. More preferably, the length is 127.76 mm+/−0.25 mm, and the width is 85.48 mm+/−0.25 mm.

The term "surface geometry" relates to the surface structure, preferably of the side walls of the consumables (60, 70, 101, 301, 302). The surface geometry preferably comprises hardware identifiers (39, 7, 6, 117, 118, 116, 102, 119, 115, 125, 305) more preferably recesses and/or ridges integrally formed in the surface of a consumable (60, 70, 101, 301, 302). Preferably, any one of all types of consumables (60, 70, 101, 301, 302) with said footprint comprise a unique surface geometry (601). A "unique surface geometry" is understood to be a surface geometry (601) as hereinbefore described which is unique for a type of consumable (60, 70, 101, 301, 302) and is substantially different from the surface geometries (601) of other consumables (60, 70, 101, 301, 302) such that the consumable (60, 70, 101, 301, 302) is specifically recognized by the recognition system (450) of the analytical system (440).

In a preferred embodiment, the system comprises stackers (600a,b) for stacking multiple consumables (60, 70, 101, 301, 302) of one type, wherein any one of said stackers (600a,b) comprises recognition elements for one type of consumable (60, 70, 101, 301, 302). The term "stacker" as used herein relates to the uptake area in the analytical system for a specific consumable (60, 70, 101, 301, 302). The multiple consumables (60, 70, 101, 301, 302) of a specific type are stacked in the stacker (600a,b). Individual consumables (60, 70, 101, 301, 302) of one type are then retrieved from the stacker (600a,b) within the system (440) and automatically transported to the module (401, 402, 403) in which they are used, either by a conveyor or, preferably by a handler (500) connected to a robotic arm (502). Thus, due to the unique surface geometry (601) of the consumable (60, 70, 101, 301, 302), a specific type of consumable (60, 70, 101, 301, 302) can only be loaded into a specific stacker (600a,b). This prevents the user from loading the wrong consumable (60, 70, 101, 301, 302) into a specific stacker (600a,b), even if the consumables (60, 70, 101, 301, 302) have the same footprint.

In a preferred embodiment, more than two different types of consumables (60, 70, 101, 301, 302) with a same footprint are comprised in the system (440). In a more preferred embodiment, more than three different types of consumables (60, 70, 101, 301, 302) with a same footprint are comprised in the system (440). The consumables (60, 70, 101, 301, 302) are preferably selected from the group consisting of tip rack (60, 70), multiwell plate (101) for sample preparation, multiwell plate (302) for amplification and/or detection, reagent cassette holder, tube holder etc.

A method is also provided for recognizing the identity of a consumable (60, 70, 101,301,302) within an analyzer (400) as described hereinbefore. Said method comprises providing one type of consumable (60, 70, 101, 301, 302), wherein said one type of consumable (60, 70, 101, 301, 302) comprises a unique surface geometry (601). The method further comprises interacting said one type of consumable (60, 70, 101, 301, 302) comprising a unique surface geometry (601) with a stacker (600a,b) comprising recognition elements (602) specific for said unique surface geometry (601). The consumable (60, 70, 101, 301, 302) is then identified when the unique surface geometry (601) is engaged by the recognition elements (602). The term "recognition elements" as used herein relates to elements, such as a guidance (602) mounted on the inside of a stacker (600a,b) which fits specifically with the unique surface geometry (601) of one type of consumable (60, 70, 101, 301, 302). Preferred analyzer (400), consumable (60, 70, 101, 301, 302) and stacker (600a,b) are as defined hereinbefore.

Finally, a consumable (60, 70, 101, 301, 302) is also provided comprising a unique surface geometry (601) constructed and arranged to allow a stacker (600a,b) to specifically identify the type of consumable (60, 70, 101, 301, 302). Preferred embodiments of consumable (60, 70, 101, 301, 302), stacker (600a,b) and surface geometry (601) are as hereinbefore described.

A schematic drawing of an exemplary analytical system (440) is shown in FIG. 51). The recognition of the surface geometry (601) by the stacker (600a,b) is shown in FIG. 51. The inner surface of the stacker (600a,b) comprises recognition elements (602). It is constructed and arranged to engage the surface geometry (601) of the consumable (60, 70, 101, 301, 302) and, thereby, the type of consumable (60, 70, 101, 301, 302) is specifically recognized and loading of the wrong type of consumable (60, 70, 101, 301, 302) is avoided. In a preferred embodiment, more than one type of multiwell plate is used in the analytical system (440), preferably in different steps of the analytical method. Thus, different types of multiwell plates (101, 301, 302) have different surface geometries that are unique for each type of multiwell plate (101, 301, 302). Each type of multiwell plate (101, 301, 302) is specifically recognized by its unique surface geometry (601).

System with Spatial Separation

A new method and system with improved contamination prevention are disclosed. In preferred embodiments, the contamination protection may be further improved by combining the claimed method with any one of the known contamination methods described above.

In one aspect of the method hereinbefore described, said first cell comprises a first air pressure, and said second cell comprises a second air pressure, wherein said first air pressure is higher than said second air pressure.

In a preferred embodiment of the method, outside air which enters said first cell is filtered. Filtering of air allows to reduce the risk of contaminants entering the analytical apparatus. Preferably, the filters are HEPA filters.

Preferably, said first and second cell are separated by a wall. Separation of cells by walls further reduces the risk of potential contaminants from one cell entering another cell.

In one aspect of the present method, the purified analyte is transferred from said first cell to said second cell through an air-lock located between said first and second cell. Preferably, the air lock comprises a door on the side of the first cell and a door on the side of the second cell. In the resting state of the air lock, both doors are on the closed position. The door on the side of the first cell opens when a plate has to pass from the first cell to the second cell. The plate is then placed on a movable plate holder. Said plate holder is then moved into the air lock. The door on the side of the first cell closes. Then, the door on the side of the second cell opens. The plate on the plate holder passes to the end of the air lock, and a handler then removes the plate from the plate holder of the air lock.

In a preferred embodiment of the method hereinbefore described, said purified analyte is comprised in a reaction vessel.

In one aspect of the present method, said reaction vessel is sealed prior to analyzing said analyte. Especially in the preferred field of nucleic acid analytics, analyzing comprises multiplying the target nucleic acid by amplification. Thus, during the analyzing process and following analysis, the reaction vessels comprise large amounts of the target nucleic acid(s) which can be a potential source of contamination. Sealing of the reaction vessels, preferably with a foil, more preferably by thermally sealing said reaction vessels with foil, further reduces the risk of potential contamination of samples and purified nucleic acids prior to analysis. Preferably, the reaction vessel is sealed prior to transport from said first cell to said second cell. The contamination prevention effect of sealing is, then, optimal.

In one aspect of the present method, a additional step comprises transferring a sample from a sample vessel to a multiwell plate in a third cell, wherein said third cell has an air-flow which is separate from said first and second cell and wherein said step precedes the steps carried out in the first cell. Preferably, the first cell is a processing cell as descried herein, the second cell is an analytical cell as described herein and the third cell is a sample cell as described herein.

In a preferred embodiment of the method, a first handler transfers said reaction vessel from said first cell to said air-lock, and a second handler transfers said reaction vessel from said air-lock to said second cell.

Preferred embodiments of cells are described hereinafter.

An automated analytical apparatus for processing an analyte is also disclosed, comprising:

a processing cell comprising a separation device for isolating and purifying said analyte, wherein said processing cell has a first air flow;

an analytical cell for analyzing said analyte contained in a reaction vessel, wherein said analytical cell has a second air flow;

a transfer system for transferring a vessel comprising said purified analyte from the processing cell to the analytical cell;

wherein said first air flow in said processing cell and said second air flow are separate.

In one aspect, said first cell comprises a first air pressure and said second cell comprises a second air pressure, wherein said first air pressure is higher than said second air pressure. The advantages of said aspect are as described hereinbefore.

In a preferred embodiment of the present method, an air-lock is located between said processing cell and said analytical cell. The advantages of said embodiment are as described hereinbefore.

In one aspect of the present method, said automated analytical apparatus additionally comprises a sample cell for transferring samples from a sample vessel to a processing vessel.

In a preferred embodiment, said apparatus comprises separation walls located between said cells. The advantages of said embodiment are as described hereinbefore.

Preferably, said sample cell comprises a filter for filtration of air flowing in said sample cell.

In one aspect of the apparatus, gaskets are comprised in the upper housing of said processing cell.

In a preferred embodiment, said reaction vessel is capped or sealed.

In one aspect of the apparatus, said transfer system comprises a first handler for transferring said reaction vessel from said processing cell to said air-lock, and a second handler for transferring said reaction vessel from said air-lock to said analytical cell.

A preferred embodiments of the apparatus is a automated nucleic acid analyzer comprising a process cell for sample preparation and an amplification cell.

Advantages and effects of said embodiments and aspects are as described hereinbefore.

Figure 54:
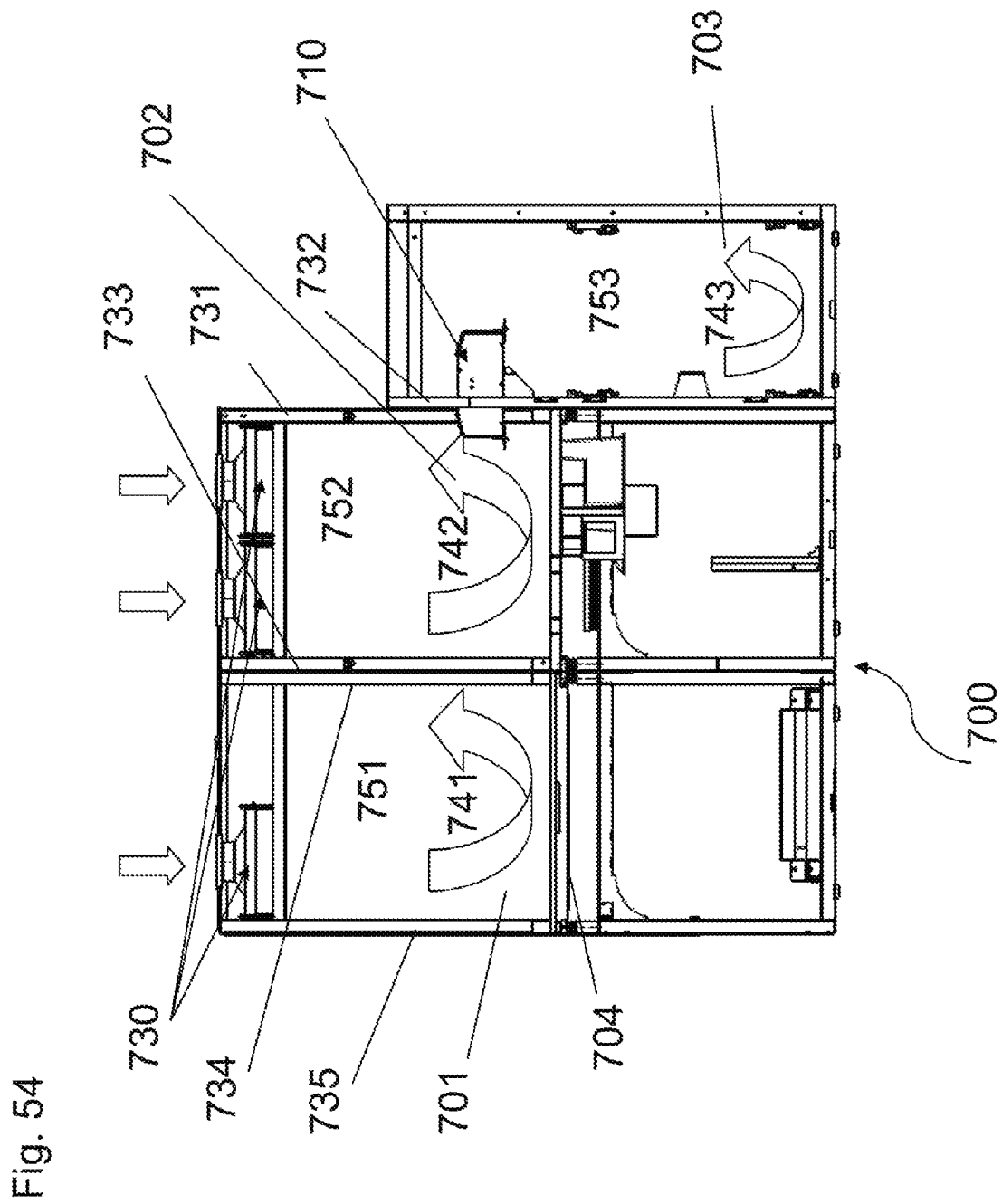
FIG. 54 shows a schematic front view of an analytical apparatus according to the invention.

FIG. 54 shows a preferred embodiment of an apparatus. The apparatus (700) comprises a first cell (702), a second cell (703) and a third cell (701). Preferred embodiments of the cells are a sample cell (701) for distributing samples to be analyzed, a process cell (702) for isolating and purifying an analyte, and an amplification/detection cell (703) for amplifying and detecting a nucleic acid analyte. The sample cell (701) and process cell (702) comprise filters (730), preferably HEPA filters, for passing air into the apparatus. Sample cell (701) has an air-flow (741) and an air pressure (751), and process cell (742) has an air flow (742) and an air pressure (752), and amplification cell (703) has an air flow (743) and an air pressure (753). Preferably, the air pressures (751) and (752) are essentially identical. Air pressure (752) is higher than air pressure (753), which prevents air from flowing from amplification cell (703) to process cell (702). Walls (731) to (734) are located between the three cells (701) to (703). An air lock (710) is located between process cell (702) and amplification cell (703).

Figure 55:
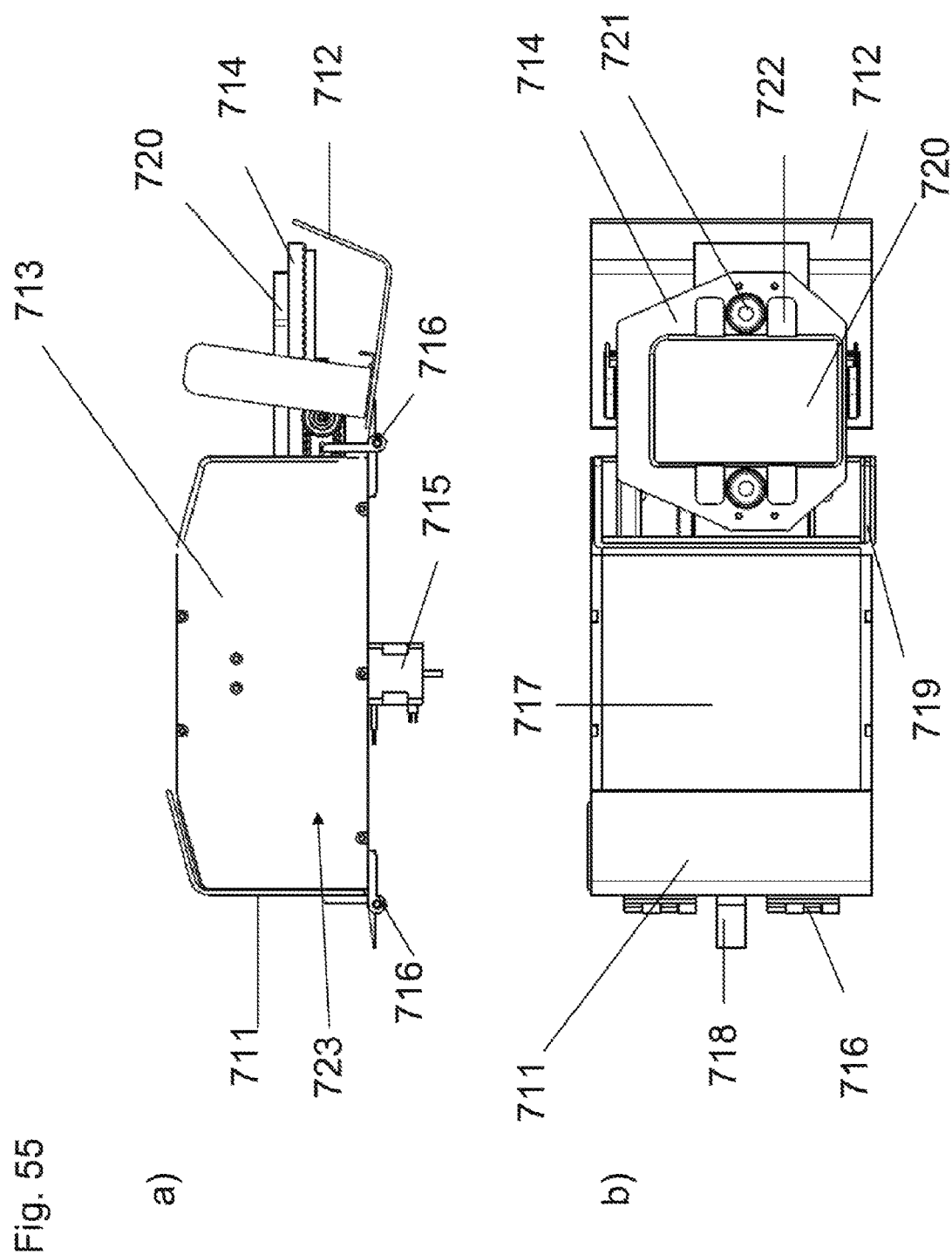
FIG. 55 shows a top view (a) and a side view (b) of the air-lock.

FIG. 55 shows a side view (a) and a top view (b) of the air lock (710). The air lock (710) has a main body (723) and side walls (713) and a door (711) on the side of the process cell (702) and a second door (712) on the side of the amplification cell (703). The doors (711), (712) are movably attached to the main body by hinges (716). Inside the air lock (710), a movable carriage (714) is mounted. The carriage (714) comprises a plate holder (720). On the carriage, at least one teach-bolt (721), preferably more than one teach-bolt (721) is mounted. The teach-bolt (721) serves as an orientation for the handler when the handler is in the process of engaging the plate on the plate holder (720) or when moving the plate onto the plate holder (720). The carriage also comprises notches (721) which provide space for the gripper fingers of the gripper. The air-lock (710) also comprises gaskets (719) for proper closing of the closing of the doors (711), (712). The main body (723) further comprises, on each end, a mechanical stopper (718) for the doors (711) and (712). There is also a motor (715) attached to the main body (723) for moving the carriage (714).

FIG. 56 shows a preferred apparatus. The apparatus comprises, on the front side, walls (761) and (762). The walls are movable to allow access to the cells (701), (702) for the handler system (704). Preferably, the walls (761, 762) are made of foil. They can be moved up and down. The apparatus further comprises outer side walls (735).

Preferred embodiments of apparatuses, methods and systems are those described below which additionally comprise the features hereinbefore described. Further preferred features of the apparatus are preferred embodiments described below.

Hardware Architecture

An analytical apparatus (400) for isolating and analyzing at least one analyte is also provided, comprising:

(i) at least one module (401) for receiving and dispensing a sample to be analyzed, (ii) at least one module (402) for isolating said analyte to be analyzed, (iii) at least one module (403) for analyzing said analyte, wherein said modules (i) to (iii) are arranged along an axis. In a preferred embodiment, said modules are arranged along an X-axis. In a second embodiment, said modules are arranged along a vertical axis. Said modules can also be arranged along an Y or a Z-axis. The axis may also be partly circular.

The apparatus further comprises at least one transport module (480) for transferring consumables (60, 70, 101, 301, 302), wherein said at least one transport module (480) is arranged parallel to said axis in front of modules (i) to (iii). The at least one transport module (480) preferably comprises a handler (500) as described hereinafter. The apparatus (400) comprises at least one consumable holder (600), wherein said at least one consumable holder (600) is arranged along said axis in front of said modules (i) to (iii). In a preferred embodiment, said consumable holder (600) is a stacker (600). Said stacker (600) preferably comprises recognition elements for recognizing consumables (60, 70, 101, 301, 302). Preferably, said stacker (600) is arranged below said transport module (480).

The terms "analytical apparatus" (400) and "analyzer" (400) and "analytical instrument" (400) are used interchangeably.

Further preferred embodiments of said stacker (600) and analytical apparatus (400) and analytical system (440) are described below.

The modules (401, 402, 403) of the analytical apparatus (400) are preferably fixed to neighboring modules (401, 402, 403). In one embodiment, the modules (401, 402, 403) are fixed to each other using fixing elements, preferably screws. In another embodiment, the modules (401, 402, 403) are fixedly mounted in frames, and the frames of neighboring modules are fixed to each other, preferably by fixing elements, more preferably by screws.

In one preferred embodiment of the apparatus hereinbefore described, said module (403) for analyzing said analyte comprises a thermal cycler. In a more preferred embodiment, the apparatus comprises at least two modules (403) for analyzing said analyte, wherein said at least two modules (403) for analyzing said analyte are mounted on two vertical levels. Other preferred embodiments of said module for analyzing said analyte comprise modules for detecting chemical reactions or modules for detecting binding of antibodies to antigens. Further preferred embodiments of said module for analyzing said analyte are described hereinafter.

The analytical apparatus (400) hereinbefore described, in a preferred embodiment, comprises more than two consumable holders (600). Preferably, at least one consumable holder is a consumable waste holder (650).

The analytical apparatus as described hereinbefore comprises, in a preferred embodiment, a module for preparing at least one reaction mixture for analyzing said at least one analyte, wherein said module is arranged between module (ii) and module (iii).

An analytical system (440) is also disclosed. An analytical system (440) comprises an analytical apparatus (400) as described herein. An analytical apparatus (400) comprises one or more modules or cells (401, 402, 403). Said modules or cells comprise stations for carrying out the processing and/or analysis of an analyte. Preferably, said apparatus and said system are automated. More preferably, consumables are loaded manually. An embodiment of the apparatus is shown schematically in FIG. 52.

The arrangement of all modules of the apparatus facilitates loading of consumables into the apparatus by the user. The apparatus and the individual modules are also more easily accessible for servicing than existing analytical apparatuses. The arrangement of the transport module along the same axis as the modules also allows an optimization of the footprint of the entire apparatus and system because the transport module is used for loading of consumables into the apparatus as well as for transfer of consumables between the different modules and the waste holder.

An automated method for isolating and analyzing at least one analyte is, furthermore, disclosed, comprising the steps of:

a) receiving a sample comprised in a sample container in a first module for receiving and distributing samples, b) transporting a first consumable from a consumable holder to said first module for receiving and distributing samples with a transport module, c) distributing said sample into receptacles of a first consumable for isolating an analyte comprised in said sample, d) transporting said first consumable for isolating an analyte comprised in said sample with said transport module from said first module for receiving and dispensing samples to a second module for isolating the analyte comprised in said sample, e) isolating said analyte in said second module for isolating the analyte, f) analyzing said analyte in a third module for analyzing an analyte.

The term "distributing" as used herein relates to the aspiration of sample from a sample container, and subsequent dispensing into receptacles for holding a liquid. Preferred embodiments of said container are described hereinafter and hereinbefore, with reference to the preferred embodiments of the analytical apparatus.

In a preferred embodiment of the method hereinbefore described, said analyte is transported by the transport module from said second module for isolating the analyte to said third module for analyzing an analyte.

In a further preferred embodiment of the automated method hereinbefore described, the isolated analyte is transferred from said first consumable for isolating an analyte comprised in said sample to a second consumable for analyzing said analyte. Preferred embodiments of said second consumable are described hereinafter.

The automated method further comprises a preferred embodiment wherein said second consumable for analyzing said analyte is transferred by the transfer module from the second module for isolating the analyte to the third module for analyzing an analyte.

More preferably, the transfer module comprises at least two transfer devices (500), wherein one transfer device transfers consumables from the consumable holder to module (i) or (ii), from module (i) to module (ii) and from module (ii) to an interface between module (ii) and module (iii), and from module (i), module (ii) or the interface to a waste consumable holder; and the second transfer device transfers consumables between the interface and module (iii). Preferably, the transfer module comprises two transfer devices.

In a preferred embodiment, said method additionally comprises, between steps e) and f), the step of preparing reaction mixtures for analyzing said at least one analyte.

Figure 52:
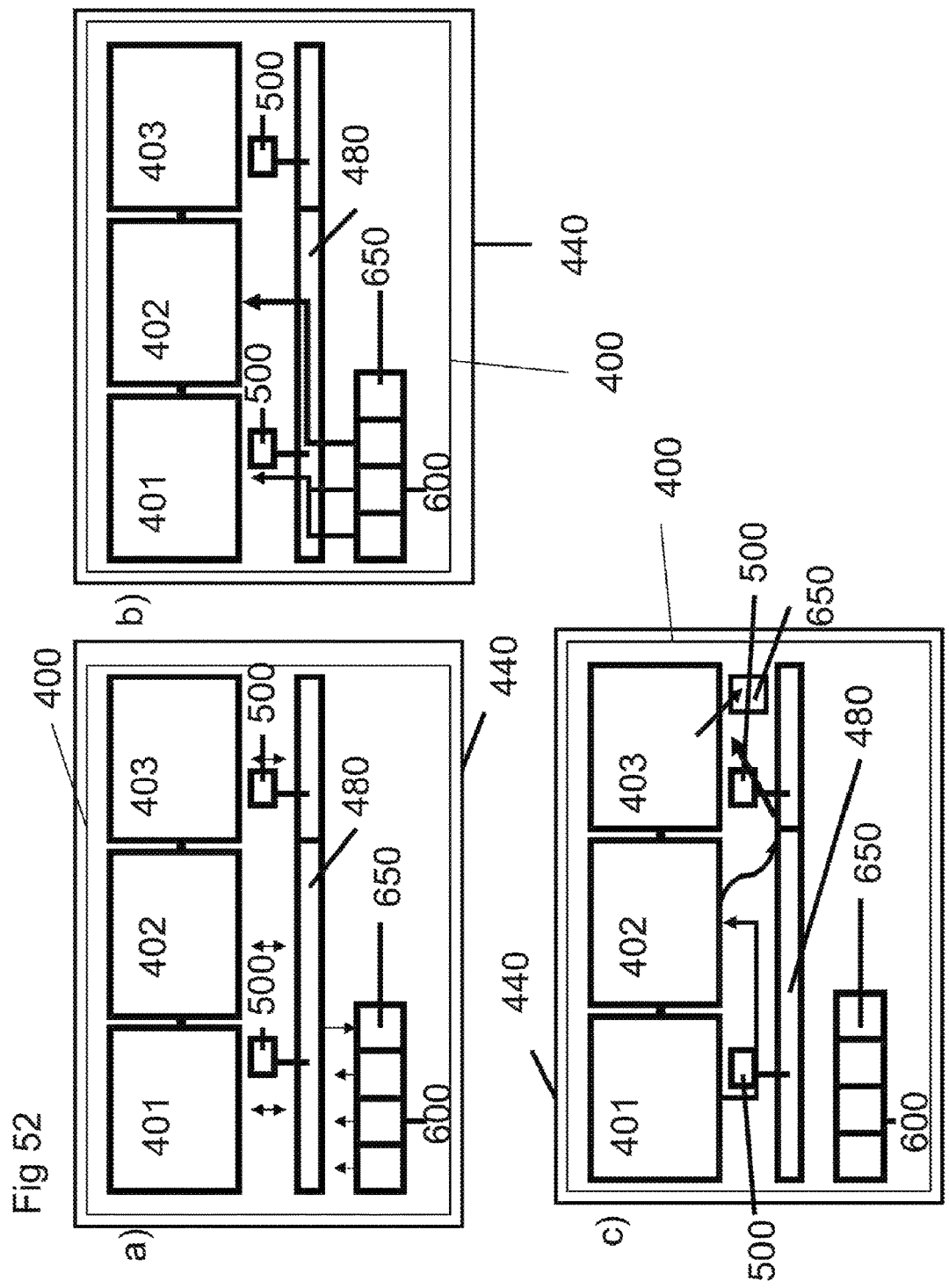
FIG. 52 shows a schematic drawing of hardware architecture with the workflows from consumable holders to different modules, and between different modules (shown by arrows); and from different modules back to the waste holder.

The flow of transported consumables is shown with arrows in FIGS. 52 (*a*) to (*c*).

Further preferred embodiments are described below.

Workflow Timing

A method and system of isolating and analyzing an analyte in an automated analyzer are also disclosed, comprising the steps of providing a liquid sample comprising said analyte to a processing vessel in a module of a first type; transferring said liquid sample comprising said analyte to a module of a second type; isolating and purifying said analyte in said processing vessel in said module of a second type; transferring said purified analyte to a module of a third type; analyzing said analyte in said module of a third type by reacting said analyte with reagents necessary to obtain a detectable signal. The timing for transfer and processing within any one module of one type is pre-defined, and said timing in any one module of one type is identical for any one analyte which is isolated and analyzed. Furthermore, the timing of any one type of module can be independent of the timing of any other type of module. Thus, the modules can work autonomously.

The advantage of the method and system is that the pre-defined timing of any one module one type allows for optimization of the overall workflow timing, and makes it possible to achieve an optimized high throughput for analytical tests.

The pre-defined timing of the modules makes it possible to start the analytical process, beginning with distribution of samples, only if, at the end of the workflow of one module, a subsequent type of module for the next step in the analytical process is available. Thus, for example, the isolation and purification of the analyte is only started if, at the end of the isolation and purification process, a module for analyzing the isolated and purified analyte is available.

Thus, in a preferred embodiment, said analyzer comprises at least two modules of a third type.

In a preferred embodiment of the method hereinbefore described an first analyte is isolated and analyzed in said automated analyzer, and a second analyte isolated and analyzed in said automated analyzer, wherein said first and second analyte are isolated and analyzed in parallel, wherein said first analyte is analyzed in one of said modules of a third type, and said second analyte is analyzed in a second one of said modules of a third type, and wherein the time for isolating and analyzing said first and second analyte are identical.

Thus, the timing of the analytical tests run in parallel can be kept identical such that any analyte is processed and analyzed in the analytical apparatus under identical conditions. This also makes it possible to use more than one module of one type in the automated analyzer while ensuring identical conditions for every test. The possibility to use multiple modules of one type makes it possible to adapt the throughput of the analytical apparatus to the needs of the user.

In a preferred embodiment, said analyte is a nucleic acid analyte. In other preferred embodiments, the analyte is an antibody, or an antigen, or a cell.

Preferably, said module of a third type is an amplification module.

In a preferred embodiment of the method hereinbefore described, said automated analyzer comprises at least two modules of a second type.

In a further preferred embodiment, said analyzer comprises at least four modules of a third type.

Preferably at least 48 samples comprising at least one analytes are isolated and purified in parallel. More preferably, said samples are isolated and purified in 96 well plates in parallel. Most preferably, the samples are analyzed in 96 well plates in at least one module of a third type.

In a preferred embodiment of the method hereinbefore described, at least 192 samples comprising at least one analyte are isolated and purified in parallel in at least two separate modules of a second type, and are analyzed in at least two separate modules of a third type. The time for processing within any one of the modules of a second type is identical, and the time for processing within any one of the modules of a third type is identical. Thus, it is possible to isolate and purify analytes in 48 well plates in at least two modules of a second type in parallel, and to then analyse the purified samples in at least four modules of a third type.

Preferred embodiments for modules of a first type are sample cells for distributing a sample comprising an analyte to a processing vessel. Sample cells and processing vessels are further described hereinafter.

Preferred embodiment for modules of a second type are cells for purifying and isolating an analyte comprising a separation station. Such cells are further described below.

Preferred embodiments of modules of a third type are analytical modules, more preferably cells for amplifying an analyte which is a target nucleic acid. Preferred embodiments of such cells include temperature controlled incubators, more preferably thermal cyclers.

Figure 53:
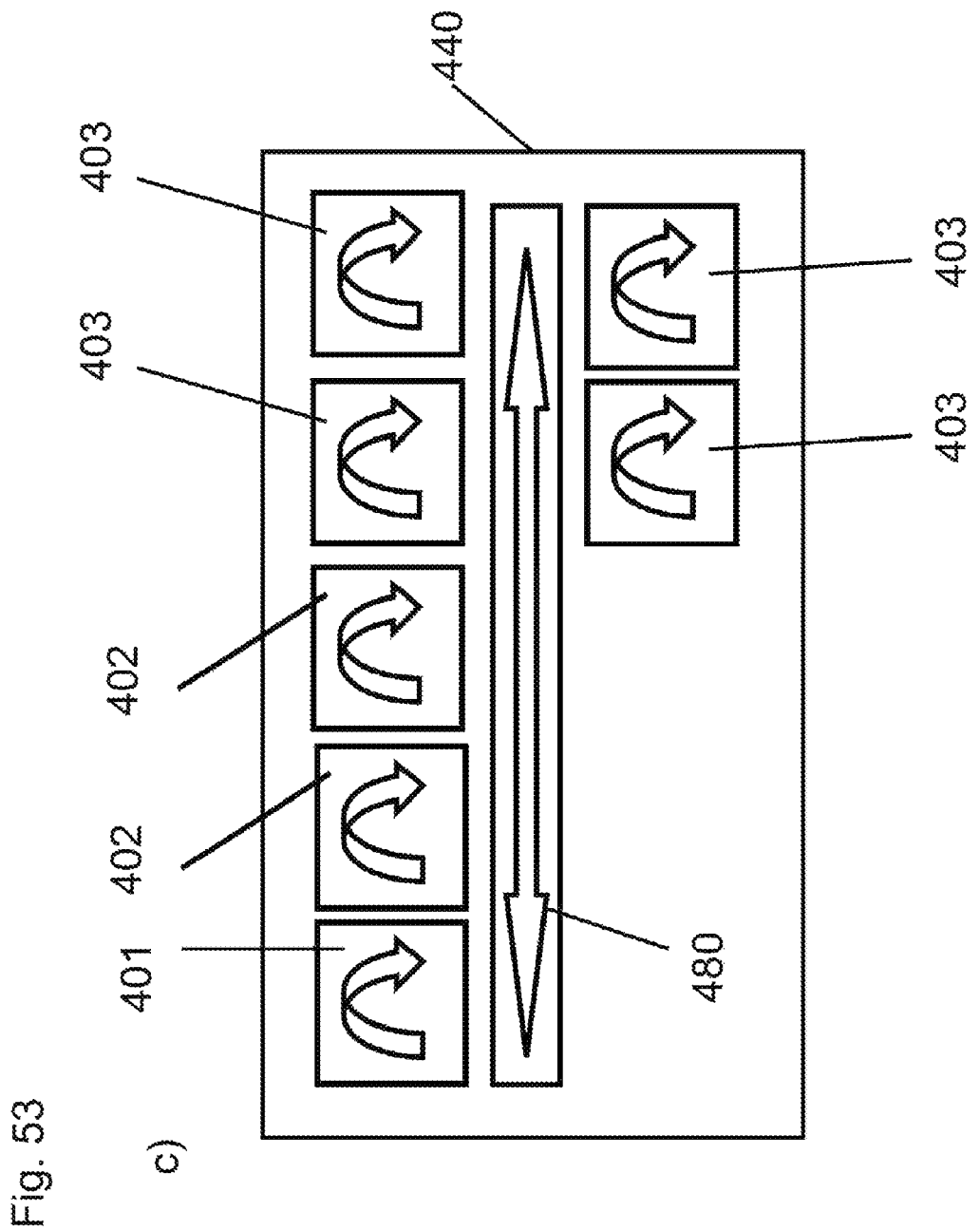
FIG. 53 shows a schematic view of systems with modules with predefined workflow timing and a transport module which is either linear (a) or circular (b)

Since the time required for analysis of a sample in a module of a third type, preferably an amplification and detection module, is longer, preferably twice as long as the isolation and purification of a sample carried out in a module of a second type, a maximum throughput can be obtained by using a setup as shown in FIG. 53 *c*) by using twice the amount of modules of a third type than modules of a second type.

The preferred workflow of any one module is described by the following method steps:
- Loading of all required consumables via pre-defined interfaces;
- Loading of samples via pre-defined interfaces;
- Initiation of a test when all samples to be analysed and all required consumables are loaded;
- Output of the result in the form of treated samples (e.g. isolated and purified samples) or of measured data or monitoring results;
- Output or disposal of used materials;
- Output or disposal of analyzed samples.

More preferably, said workflow additionally comprises, for the module of a second type, the loading of reagents.

The transferring in the transfer system is manual or automated. Preferably, the transfer is automated. The transfer system transfers consumables and certain reagents between modules and storage areas. Preferred embodiments of storage areas are described below. A further preferred storage area is a fridge.

The apparatus used in the method hereinbefore described preferably comprises a linear transfer module. In another embodiment, it preferably comprises a rotational transfer module.

The timing of the transfer system which connects the modules is not critical. This means that manual operations on the system during the process, such as loading with consumables, or loading of samples into any one of the modules, do not affect the workflow of the overall system. Also, pauses between two types of modules are, thus, possible without affecting the workflow in the critical processes (those in modules of a first type, of a second type and of a third type).

Preferably, in the method hereinbefore described, the time for isolating and purifying and analyzing any one analyte is identical to the time for isolating and purifying and analyzing any other analyte.

In a preferred embodiment, the process of providing and isolating and purifying at least one analyte is started conditional on the availability of a module of a third type when the process of isolating and purifying and preparing of reaction mixtures is terminated.

The method disclosed herein also makes it possible to generate systems comprising multiple analytical apparatuses with said modules, or to connect multiple systems while ensuring that the critical workflows remain constant and that any one analyte is isolated, purified and processed in the system under identical conditions. This improves precision, accuracy and reliability of the analytical tests performed in parallel. It is also possible, with the claimed method, to introduce pauses that are not critical for the analytical test when the process in a module of one type is finished, and before the workflow of the subsequent type of module is started. However, such pauses are not possible for time-critical steps.

The method and system hereinbefore described may additionally also comprise a module of a fourth type for preparing reactions for analysis in the module of a third type; and a module of a fifth type for detecting a reaction performed in said module of a third type. Preferably, analysis of an analyte comprises both reaction and detection in said module of a third type.

Further preferred embodiments of the method hereinbefore described are described below.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An method of isolating and analyzing a nucleic acid analyte in an automated analyzer, comprising the steps of
providing a liquid sample comprising said nucleic acid analyte to a processing vessel in a sample cell for distributing a sample comprising a nucleic acid analyte to a processing vessel;
transferring said liquid sample comprising said nucleic acid analyte to a cell for purifying and isolating a nucleic acid analyte comprising a separation station;
isolating said nucleic acid analyte in said processing vessel in said cell for purifying and isolating a nucleic acid analyte;
transferring said isolated nucleic acid analyte to an amplification module;
analyzing said nucleic acid analyte in said amplification module by reacting said nucleic acid analyte with reagents necessary to obtain a detectable signal;
wherein the timing for transfer and processing within said sample cell, said cell for purifying and isolating a nucleic acid analyte and said amplification module is pre-defined, and wherein said timing in said sample cell, said cell for purifying and isolating a nucleic acid analyte and said amplification module is identical for any nucleic acid analyte which is isolated and analyzed, and wherein the step of isolating said nucleic acid analyte in said cell for purifying and isolating a nucleic acid analyte is started only if at the end of the isolation step, the amplification module is available.

2. The method of claim 1, wherein said automated analyzer comprises at least two amplification modules.

3. The method of claim 1, wherein said automated analyzer comprises at least two cells for purifying and isolating a nucleic acid analyte comprising a separation station.

4. The method of any one of claim 1, wherein said analyzer comprises at least four amplification modules.

5. The method of claim 1, wherein at least 48 samples comprising at least two nucleic acid analytes are isolated in parallel.

6. The method of claim 5, wherein at least 192 samples comprising at least two nucleic acid analytes are isolated in parallel in two separate cells for purifying and isolating a nucleic acid analyte comprising a separation station, and are analyzed in four separate amplification modules, wherein the time for processing within any one of the cell for purifying and isolating a nucleic acid analyte is identical, and the time for processing within any one of the amplification modules is identical.

7. The method of claim 1, wherein said transferring step is automated.

8. The method of claim 1, wherein said analyzer comprises a linear transfer module.

9. The method of claim 1, wherein said analyzer comprises a rotational transfer module.

10. The method of claim 1, wherein the time for isolating and analyzing any one nucleic acid analyte is identical to the time for isolating and analyzing any other nucleic acid analyte.

* * * * *